(12) United States Patent
Yang et al.

(10) Patent No.: US 8,222,247 B2
(45) Date of Patent: Jul. 17, 2012

(54) MODULATORS OF GLUCOCORTICOID RECEPTOR, AP-1, AND/OR NF-KAPPABETA ACTIVITY AND USE THEREOF

(75) Inventors: Bingwei Vera Yang, Belle Mead, NJ (US); Lidia M. Doweyko, Long Valley, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 461 days.

(21) Appl. No.: 12/513,229

(22) PCT Filed: Oct. 31, 2007

(86) PCT No.: PCT/US2007/083090
§ 371 (c)(1),
(2), (4) Date: Jul. 30, 2009

(87) PCT Pub. No.: WO2008/057859
PCT Pub. Date: May 15, 2008

(65) Prior Publication Data
US 2010/0004219 A1 Jan. 7, 2010

Related U.S. Application Data

(60) Provisional application No. 60/855,952, filed on Nov. 1, 2006.

(51) Int. Cl.
*A61K 31/5377* (2006.01)
*C07D 265/30* (2006.01)
(52) U.S. Cl. .................... 514/231.5; 544/107
(58) Field of Classification Search .............. 514/231.5; 544/107
See application file for complete search history.

(56) References Cited

U.S. PATENT DOCUMENTS
2004/0082568 A1 4/2004 Yang

FOREIGN PATENT DOCUMENTS
| WO | WO 2004/103957 | 12/2004 |
|---|---|---|
| WO | WO 2005/037196 | 4/2005 |
| WO | WO 2005/072732 | 8/2005 |
| WO | WO 2007/073503 | 6/2007 |
| WO | WO2008/021926 | 2/2008 |
| WO | WO 2008/057855 | 5/2008 |
| WO | WO 2008/057856 | 5/2008 |
| WO | WO 2008/057857 | 5/2008 |
| WO | WO 2008/057862 | 5/2008 |

OTHER PUBLICATIONS

Baldwin, Jr., A.S., "The transcription factor NF-ηB and human disease", The Journal of Clinical Investigation, vol. 107, No. 1, pp. 3-6 (2001).
Burke, J.R., "Targeting 1κB kinase for the treatment of inflammatory and other disorders", Current Opinion in Drug Discovery & Development, vol. 6, No. 5, pp. 720-728 (2003).
Caldenhoven, E. et al., "Negative Cross-Talk between ReIA and the Glucocorticoid Receptor: A Possible Mechanism for the Antiinflammatory Action of Glucocorticoids", Molecular Endocrinology, vol. 9, No. 4, pp. 401-412 (1995).
Chillous, S.E. et al., "A Nonresolutive Approach to the Preparation of Configurationally Pure Difunctional Molecules", J. Org. Chem., vol. 47, No. 27, pp. 5418-5420 (1982).
Chakravarti, D. et al., "Role of CBP/P300 in nuclear receptor signalling", Nature, vol. 383, pp. 99-103 (1996).
Diamond, M.I. et al., "Transcription Factor Interactions: Selectors of Positive or Negative Regulation from a Single DNA Element", Science, vol. 249, pp. 1266-1272 (1990).
Firestein, G.S. et al., "Signal Transduction and Transcription Factors in Rheumatic Disease", Arthritis & Rheumatism, vol. 42, No. 4, pp. 609-621 (1999).
Girgis, N.S., "New 5-Hydroxy-pyrazoles for Pesticide Research", Egypt. J. Chem., vol. 24, No. 2, pp. 109-115 (1981).
Jonat, C. et al., "Antitumor Promotion and Antiinflammation: Down-Modulation of AP-1 (Fos/Jun) Activity by Glucocorticoid Hormone", Cell, vol. 62, pp. 1189-1204 (1990).
Kamei, Y. et al., "A CBP Integrator Complex Mediates Transcriptional Activation and AP-1 Inhibition by Nuclear Receptors", Cell, vol. 85, pp. 403-414 (1996).
Manning, A.M., et al., "Targeting JNK for Therapeutic Benefit: from Junk to Gold?", Nature, vol. 2, pp. 554-565 (2003).

(Continued)

*Primary Examiner* — Taofiq A Solola
(74) *Attorney, Agent, or Firm* — Burton Rodney; Laurelee A. Duncan

(57) ABSTRACT

Novel non-steroidal compounds are provided which are useful in treating diseases associated with modulation of the glucocorticoid receptor, AP-1, and/or NF-κB activity, including metabolic and inflammatory or immune associated diseases or disorders having the structure of formula I or an enantiomer, diastereomer, tautomer, or a pharmaceutically-acceptable salt, thereof, wherein: A is a 5-, 6-, or 7-membered heterocyclo or heteroaryl, each containing 1, 2, or 3 heteroatoms selected from N, O, and S and substituted with one to four groups, $R_1$, $R_2$, $R_3$, and/or $R_4$; provided that (i) A is not tetrazole or (ii) if A is thienyl or furanyl then Z M is selected from alkyl, cycloalkyl, aryl, heterocyclo, and heteroaryl; Z is selected from alkyl, CF3, OH, cycloalkyl, heterocyclo, aryl, heteroaryl, —C(=O)NR$_8$R$_9$, —C(=O)R$_8$, —C(NCN)NR$_8$R$_9$, —C(=O)OR$_8$, —SO$_2$R$_8$, and —SO$_2$NR$_8$R$_9$. Also provided are pharmaceutical compositions, combinations and methods of treating metabolic and inflammatory or immune associated diseases or disorders using said compounds.

(I)

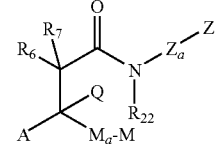

14 Claims, No Drawings

OTHER PUBLICATIONS

Miesfeld, R. et al., "Characterization of a steroid hormone receptor gene and mRNA in wild-type and mutant cells", Nature, vol. 312, pp. 779-781 (1984).

Pastour, P., "Influence of secondary bases on the condensations of aldehydes with active methylene groups; particular case of acetylacetanilide", Bulletin de la Société Chimique de France, pp. 297-298 (1955).

Peltz, G., "Transcription factors in immune-mediated disease", Current Opinion in Biotechnology, vol. 8, pp. 467-473 (1997).

Reichardt, H.M. et al., "DNA Binding of the Glucocorticoid Receptor is Not Essential for Survival", Cell, vol. 93, pp. 531-541 (1998).

Reichardt, H.M. et al., "Repression of inflammatory responses in the absence of DNA binding by the glucocorticoid receptor", The EMBO Journal, vol. 20, No. 24, pp. 7168-7173 (2001).

Weinberger, C. et al., "Domain structure of human glucocorticoid receptor and its relationship to the v-*erb*-A oncogene product", Nature, vol. 318, pp. 670-672 (1985).

Weinberger, C. et al., "Identification of Human Glucocorticoid Receptor Complementary DNA Clones by Epitope Selection", Science, vol. 228, pp. 740-742 (1985).

Yang-Yen, H.-F. et al., "Transcriptional Interference between c-Jun and the Glucocorticoid Receptor: Mutual Inhibition of DNA Binding Due to Direct Protein-Protein Interaction", Cell, vol. 62, pp. 1205-1215 (1990).

US 8,222,247 B2

MODULATORS OF GLUCOCORTICOID RECEPTOR, AP-1, AND/OR NF-KAPPABETA ACTIVITY AND USE THEREOF

This application claims the benefit of priority from U.S. provisional application Ser. No. 60/855,952 filed Nov. 1, 2006, which is incorporated herein by reference.

FIELD OF THE INVENTION

The present invention relates to new non-steroidal compounds which are effective modulators of the glucocorticoid receptor, AP-1, and/or NF-κB activity and thus are useful in treating diseases or disorders including metabolic and inflammatory or immune associated diseases or disorders. The present invention also provides compositions and combinations thereof and methods for using such compounds and compositions to treat these and related diseases or disorders.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A. S., *Journal of Clin. Investigation*, 107, 3 (2001); Firestein, G. S., and Manning, A. M., *Arthritis and Rheumatism*, 42, 609 (1999); and Peltz, G., *Curr. Opin. in Biotech.* 8, 467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/c-jun). Compounds which inhibit JNK have been shown to be efficacious in animal models of inflammatory disease. See Manning, A. M. and Davis, R. J., *Nature Rev. Drug Disc.*, V. 2, 554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK has been shown to be efficacious in animal models of inflammatory disease. See Burke, J. R., *Curr. Opin. Drug Discov. Devel.*, September; 6(5), 720-8, (2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger et al., *Science*, 228, 740-742 (1985); Weinberger et al., *Nature*, 318, 670-672 (1986) and for results in rats see Miesfeld, R., *Nature*, 312, 779-781 (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C. et al., *Cell*, 62, 1189 (1990); Yang-Yen, H. F. et al., *Cell*, 62, 1205 (1990); Diamond, M. I. et al., *Science* 249, 1266 (1990); and Caldenhoven, E. et al., *Mol. Endocrinol.*, 9, 401 (1995). Other mechanisms such as sequestration of co-activators by GR have also been proposed. See Kamei, Y. et al., *Cell*, 85, 403 (1996); and Chakravarti, D. et al., *Nature*, 383, 99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Reichardt, H. M. et al., *Cell*, 93, 531 (1998) and Reichardt, H. M., *EMBO J.*, 20, 7168 (2001).

Compounds that modulate AP-1 and NF-κB activity would be in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents, however their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

DESCRIPTION OF THE INVENTION

The present invention relates to new non-steroidal compounds which are effective modulators of the glucocorticoid receptor, AP-1, and/or NF-κB activity and thus are useful in treating diseases or disorders including metabolic and inflammatory or immune associated diseases or disorders. The present invention also provides compositions thereof and methods for using such compounds and compositions to treat these and related diseases or disorders.

In accordance with one aspect of the invention, compounds are provided having the structure of formula (I)

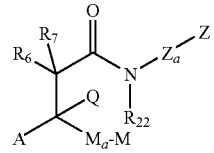

or an enantiomer, diastereomer, tautomer, or a pharmaceutically-acceptable salt, thereof, wherein:

A is a 5-, 6-, or 7-membered heterocyclo or heteroaryl, each containing 1, 2, or 3 heteroatoms selected from N, O, and S and substituted with one to four groups, $R_1$, $R_2$, $R_3$, and/or $R_4$, provided that (i) A is not tetrazole or (ii) if A is thienyl or furanyl then Z is selected from a group other than succinimido or thalimido;

M is selected from alkyl, cycloalkyl, aryl, heterocyclo, and heteroaryl;

$M_a$ is a linker between C and M and is selected from a bond and $C_1$-$C_3$alkylene;

Q is selected from
  (i) hydrogen, halogen, nitro, cyano, hydroxy, $C_{1-4}$alkyl, and substituted $C_{1-4}$ alkyl; or
  (ii) Q is combined with $R_6$ and with the carbon atoms to which they are attached to form a 3- to 6-membered cycloalkyl; or
  (iii) Q and M are combined with the carbon atom(s) to which they are attached to form a 3- to 7-membered ring containing 1-2 heteroatoms which are independently selected from the group consisting of O, S, $SO_2$, and N which ring may be optionally substituted with 0-2 $R_5$ groups or carbonyl;

Z is selected from alkyl, $CF_3$, OH, cycloalkyl, heterocyclo, aryl, heteroaryl, —C(=O)$NR_8R_9$, —C(=O)$R_8$, —C(NCN)$NR_8R_9$, —C(=O)$OR_8$, —$SO_2R_8$, and —$SO_2NR_8R_9$;

$Z_a$ is a linker between N and Z and is selected from a bond and $C_1$-$C_6$ alkylene;

$R_1$, $R_2$, $R_3$, and $R_4$ at each occurrence are independently selected from hydrogen, halogen, alkyl, substituted alkyl, alkenyl, substituted alkenyl, alkynyl, substituted alkynyl, nitro, cyano, —$OR_{10}$, —$SR_{10}$, —$NR_{10}R_{11}$, —C(=O)$R_{10}$, —$CO_2R_{10}$, —C(=O)$NR_{10}R_{11}$, —O—C(=O)$R_{10}$, —$NR_{10}$C(=O)$R_{11}$, —$NR_{10}$C(=O)$OR_{11}$, —$NR_{10}$C(S)$OR_{11}$, —S(=O)$_pR_{12}$, —$NR_{10}SO_2R_{12}$, —$SO_pNR_{10}R_{11}$, cycloalkyl, heterocyclo, aryl, and heteroaryl;

$R_5$ at each occurrence is independently selected from hydrogen, halogen, alkyl, substituted alkyl, alkenyl, substituted alkenyl, alkynyl, substituted alkynyl, nitro, cyano, —$OR_{13}$, —$NR_{13}R_{14}$, —C(=O)$R_{13}$, —$CO_2R_{13}$, —C(=O)$NR_{13}R_{14}$, —O—C(=O)$R_{13}$, —$NR_{13}$C(=O) $R_{14}$, —$NR_{13}$C(=O)$OR_{14}$, —$NR_{13}$C(S)$OR_{14}$, —S(=O)$_p$ $R_{15}$, —$NR_{13}SO_2R_{15}$, —$SO_2NR_{13}R_{14}$, cycloalkyl, heterocyclo, aryl, or heteroaryl;

$R_6$ is selected from alkyl, substituted alkyl, alkenyl, substituted alkenyl, alkynyl, substituted alkynyl, cyano, —C(=O)$R_{17}$, —$CO_2R_{17}$, —C(=O)$NR_{16}R_{17}$, cycloalkyl, heterocyclo, aryl, and heteroaryl, provided that heterocyclo or heteroaryl are attached through a carbon atom;

$R_7$ is selected from hydrogen, halogen, alkyl, substituted alkyl, alkenyl, substituted alkenyl, alkynyl, substituted alkynyl, nitro, cyano, —$OR_{19}$, —$NR_{19}R_{20}$, —C(=O)$R_{19}$, —$CO_2R_{19}$, —C(=O)$NR_{19}R_{20}$, —O—C(=O)$R_{19}$, —$NR_{19}$C(=O)$R_{20}$, —$NR_{19}$C(=O)$OR_{20}$, —$NR_{19}$C(=S) $OR_{20}$, —S(=O)$_pR_{21}$, —$NR_{19}SO_2R_{21}$, —$SO_2NR_{19}R_{20}$, cycloalkyl, heterocyclo, aryl, and heteroaryl;

or $R_6$ and $R_7$ are taken together with the carbon to which they are attached to form a cycloalkyl or heterocyclo group;

$R_8$, $R_9$, $R_{10}$, $R_{11}$, $R_{13}$, $R_{14}$, $R_{16}$, $R_{17}$, $R_{19}$ and $R_{20}$ at each occurrence are independently selected from:
  (i) hydrogen, alkyl, substituted alkyl, alkenyl, substituted alkenyl, alkynyl, substituted alkynyl, —$SO_p$alkyl, cycloalkyl, aryl, heteroaryl, and heterocyclo; or
  (ii) $R_8$ is taken together with $R_9$; and/or $R_{10}$ is taken together with $R_{11}$; and/or $R_{16}$ is taken together with $R_{17}$; and/or $R_{19}$ is taken together with $R_{20}$ to form a 4- to 7-membered heteroaryl or heterocyclo ring;

$R_{12}$, $R_{15}$, $R_{18}$, and $R_{21}$ are independently selected from alkyl, substituted alkyl, alkenyl, substituted alkenyl, alkynyl, substituted alkynyl, cycloalkyl, aryl, heteroaryl, or heterocyclo;

$R_{22}$ is selected from hydrogen, alkyl, substituted alkyl, C(=O)alkyl, $CO_2$(alkyl), $SO_2$alkyl, alkoxy, amino, substituted amino, aryl, heteroaryl, heterocyclo, and cycloalkyl; and p is 1 or 2.

It is preferred in compounds of formula (I) that A is selected from pyrrolyl, pyrazolyl, pyrazolinyl, imidazolyl, oxazolyl, isoxazolyl, oxadiazolyl, triazolyl, thiazolyl, thiadiazolyl, isothiazolyl, furanyl, thienyl, oxadiazolyl, pyridyl, pyrazinyl, pyrimidinyl, pyridazinyl, and triazolyl, each of which is optionally substituted by one to four groups, $R_1$, $R_2$, $R_3$, and/or $R_4$. Even more preferably, A is thienyl, thiazolyl, thiadiazolyl, furanyl, pyrrolyl, pyrazolyl, pyridyl or primidinyl, each group optionally substituted by one to four groups, $R_1$, $R_2$, $R_3$, and/or $R_4$.

It is also preferred that in the compounds of formula (I)

Q is hydrogen or alkyl;

M is alkyl, aryl, cycloalkyl, heteroaryl, arylalkyl, heterocyclo, alkylarylalkyl, alkylaryl, or haloaryl;

$R_6$ is selected from $C_{1-4}$alkyl, substituted $C_{1-4}$alkyl, cyano, and $C_{3-7}$cycloalkyl; and $R_7$ is selected from hydrogen, $C_{1-4}$alkyl, substituted $C_{1-4}$alkyl, nitro, —$NR_{19}R_{20}$, cyano, hydroxy, $C_{1-4}$alkoxy, and $C_{3-7}$cycloalkyl;

or $R_6$ and $R_7$ are taken together with the carbon to which they are attached to form a $C_{3-7}$cycloalkyl, group;

or Q and $R_6$ together with the carbon atoms to which they are attached are combined to form

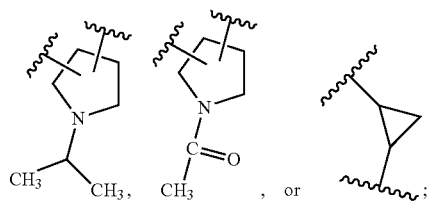

or Q and $M_a$-M together with the atom to which they are both attached are combined to form

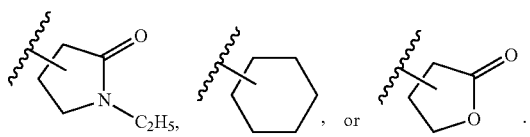

It is more preferred that in the compounds of formula (I)
$M_a$ is a bond;
M is selected from $C_{1-6}$alkyl and aryl (more preferably, M is an unsubstituted phenyl or phenyl substituted by 1-3 groups selected from halogen and/or a 6-membered heterocyclo having at least one heteroatom selected from N, S, and O); and
Q is hydrogen or $C_{1-6}$alkyl, (more preferably, Q is hydrogen).

It is also preferred in the compounds of formula (I) that
$Z_a$ is a bond;
Z is heteroaryl having 1, 2, or 3 heteroatoms selected from N, S and O, substituted with one, two or three groups, $R'''$, $R''$, and/or $R^o$;
$R'''$, $R''$, and/or $R^o$ are independently selected from (i) hydrogen, halogen, alkyl, substituted alkyl, alkenyl, substituted alkenyl, alkynyl, substituted alkynyl, nitro, cyano, $OR_{23}$, $NR_{23}R_{24}$, $C(=O)R_{23}$, $CO_2R_{23}$, $C(=O)NR_{23}R_{24}$, —O—C(=O)$R_{23}$, $NR_{23}C(=O)R_{24}$, $NR_{23}C(=O)OR_{24}$, $NR_{23}C(=S)OR_{24}$, $S(=O)_pR_{25}$, $NR_{23}SO_2R_{25}$, $SO_2NR_{23}R_{24}$, cycloalkyl, heterocyclo, aryl, and heteroaryl; or (ii) two of $R'''$, $R''$, and/or $R^o$ located on adjacent atoms together with the atoms to which they are attached may combine to form a cycloalkyl, aryl, heteroaryl, or heterocyclo ring;
$R_{23}$ and $R_{24}$ at each occurrence are independently selected from hydrogen, alkyl, substituted alkyl, C(=O)alkyl, $CO_2$(alkyl), $SO_2$alkyl, alkenyl, substituted alkenyl, alkynyl, substituted alkynyl, amino, aryl, heteroaryl, heterocyclo, and cycloalkyl;
$R_{25}$ is selected from alkyl, substituted alkyl, alkenyl, substituted alkenyl, alkynyl, substituted alkynyl, amino, substituted amino, heteroaryl, heterocyclo, cycloalkyl, and aryl.

In more preferred embodiments of compounds of formula (I),
$Z_a$ is a bond;
Z is selected from

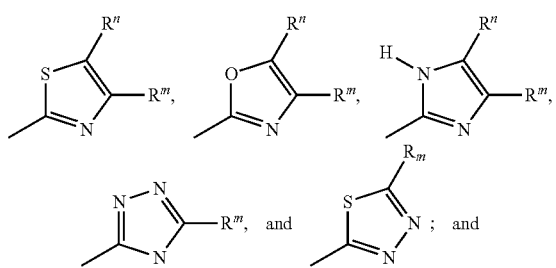

$R'''$ and $R''$ at each occurrence are independently selected from hydrogen, halogen, cycloalkyl, cyano, haloalkyl, thioalkyl, —$CO_2R_{23}$, —$NR_{23}R_{24}$, —$C(=O)R_{23}$, —C(O)N($R_{23}$)($R_{24}$), $OR_{23}$, $C_{1-4}$alkyl, substituted $C_{1-4}$alkyl, aryl, heteroaryl and heterocyclo;
or $R'''$ and $R''$ together with the atoms to which they are attached combine to form an optionally substituted fused 5- to 7-membered cycloalkyl, aryl, heteroaryl, or heterocyclo ring; and
$R_{23}$ and $R_{24}$ at each occurrence are independently selected from hydrogen, alkyl, substituted alkyl, C(=O)alkyl, $CO_2$(alkyl), $SO_2$alkyl, alkenyl, substituted alkenyl, alkynyl, substituted alkynyl, amino, aryl, heteroaryl, heterocyclo, and cycloalkyl.

In still more preferred embodiments of compounds of formula (I),
A is thienyl, thiazolyl, isothiazolyl, thiadiazolyl, furanyl, pyrrolyl, pyrazolyl, pyridyl, or pyrimidinyl, each group optionally substituted by 1 to 4 groups, $R_1$, $R_2$, $R_3$, and/or $R_4$;
$R_1$, $R_2$, $R_3$, and/or $R_4$ are independently selected from (i) hydrogen, halogen, $C_{1-4}$alkyl, CN, $C_{2-4}$alkenyl, $C_{2-4}$alkynyl, $CO_2R_{10}$, $SR_{10}$, $SO_2R_{12}$, $OR_{10}$, $SO_pNR_{10}R_{11}$, and $NR_{10}R_{11}$; and/or (ii) $C_{0-3}$alkylene substituted by an optionally substituted group selected from phenyl and a 5- to 7-membered heteroaryl;
$R_{10}$ and $R_{11}$ are, at each occurrence independently selected from (i) hydrogen, $C_{1-6}$alkyl, substituted $C_{1-6}$alkyl, and $SO_2(C_{1-4}$alkyl); and/or (ii) $C_{3-7}$cycloalkyl, heterocyclo, aryl, and heteroaryl, each group optionally substituted; and/or (iii) $R_{10}$ is taken together with $R_{11}$ and the nitrogen atom to which they are both attached to form a 4- to 6-membered heteroaryl or heterocyclo, each group optionally substituted; and
$R_{12}$ at each occurrence is selected from an optionally substituted group selected from $C_{1-6}$alkyl, $C_{3-7}$cycloalkyl, heterocyclo, aryl, and heteroaryl.

More preferably, $R_1$, $R_2$, $R_3$, and $R_4$ are independently selected from hydrogen, halogen, alkoxy, morpholinyl optionally substituted with OH, piperidinyl, —NH(CH$_2$)$_n$(phenyl optionally substituted with $C_{1-4}$alkyl), pyrrolidinyl, furyl, or phenyl optionally substituted by one to two groups selected from halogen, alkoxy, $C_{1-6}$alkyl, $CO_2R_{10}$, (e.g. COOH, C(O)O$C_{1-4}$alkyl), and C(O)N$R_{10}R_{11}$ (e.g. C(O)N($C_{1-4}$alkyl or $C_{3-6}$cycloalkyl)$_2$, C(O)NH($C_{1-4}$alkyl or $C_{3-6}$cycloalkyl), or C(O)(N-morpholinyl, N-piperidinyl, N-pyrrolidinyl, or N-aziridinyl, each group optionally substituted by halogen)); and n is 0, 1 or 2.

In other preferred embodiments of compounds of formula (I),
A is selected from:

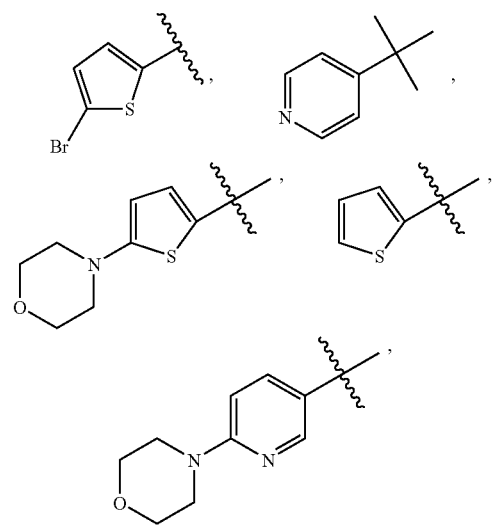

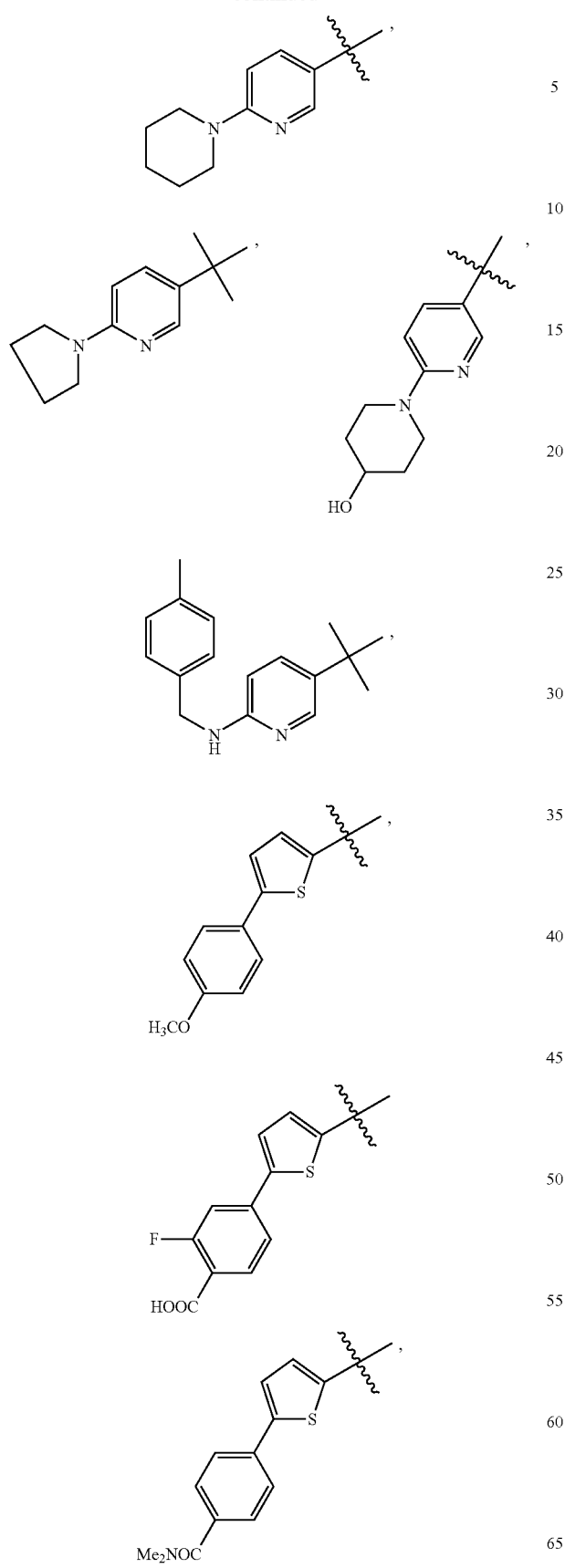
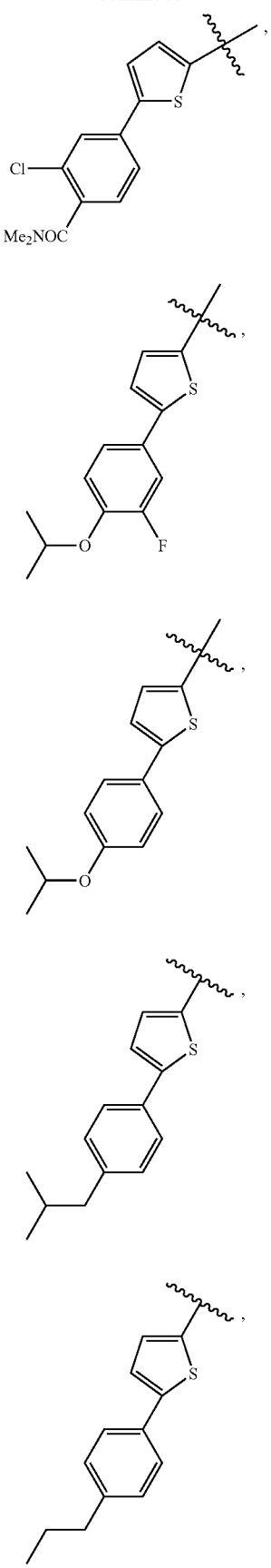

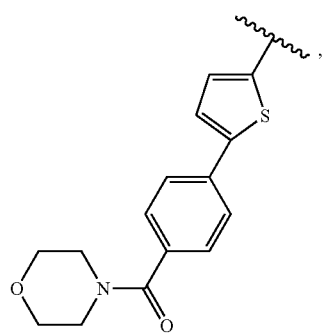
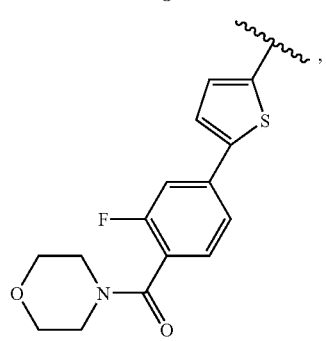
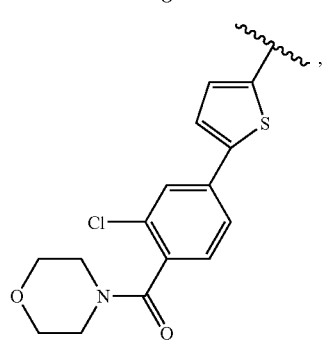
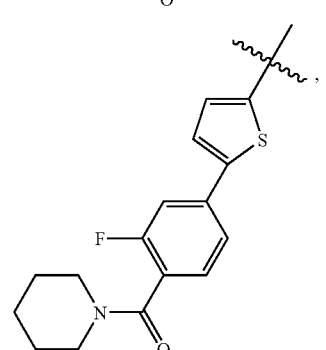
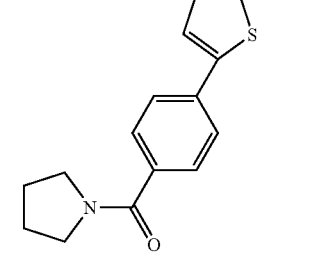
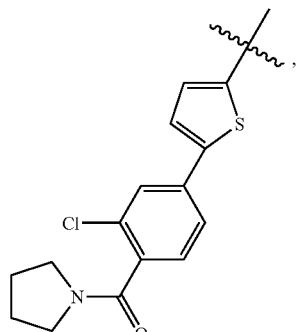
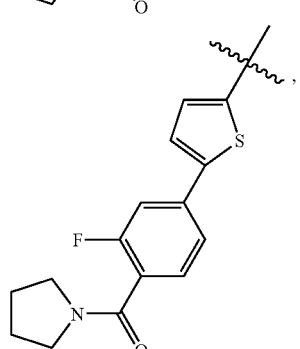
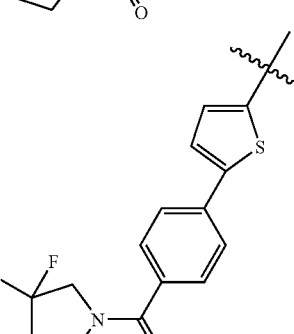
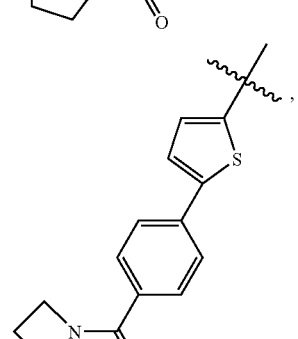
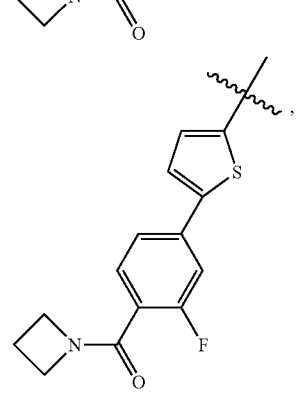

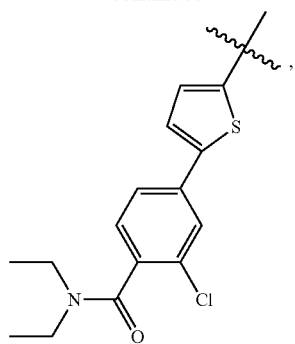
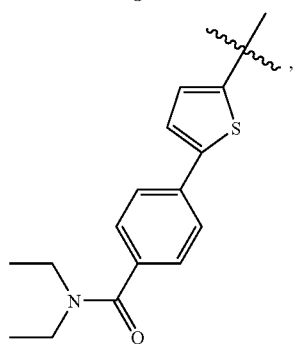
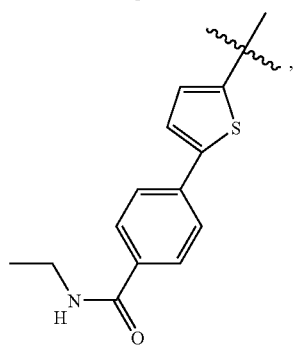
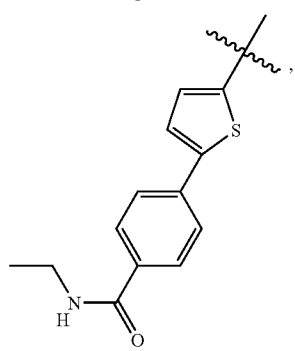
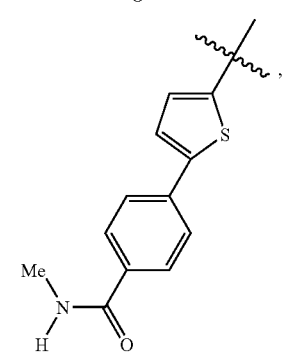
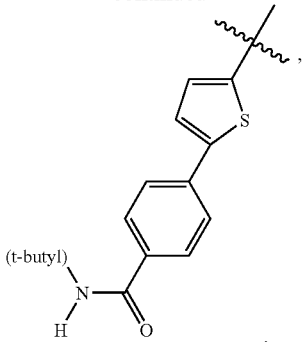
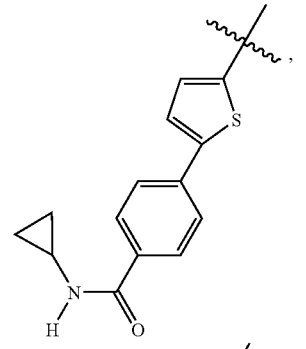
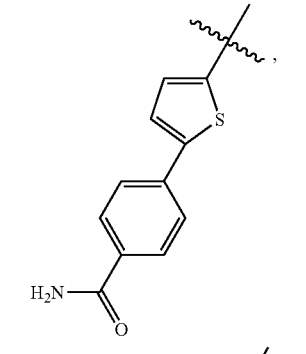
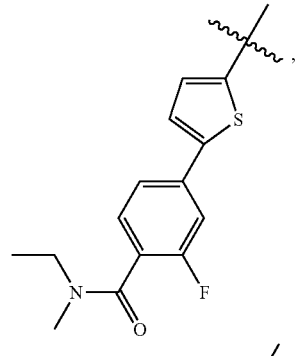
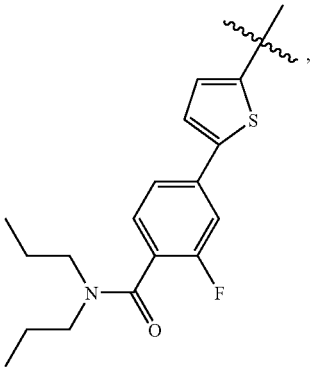

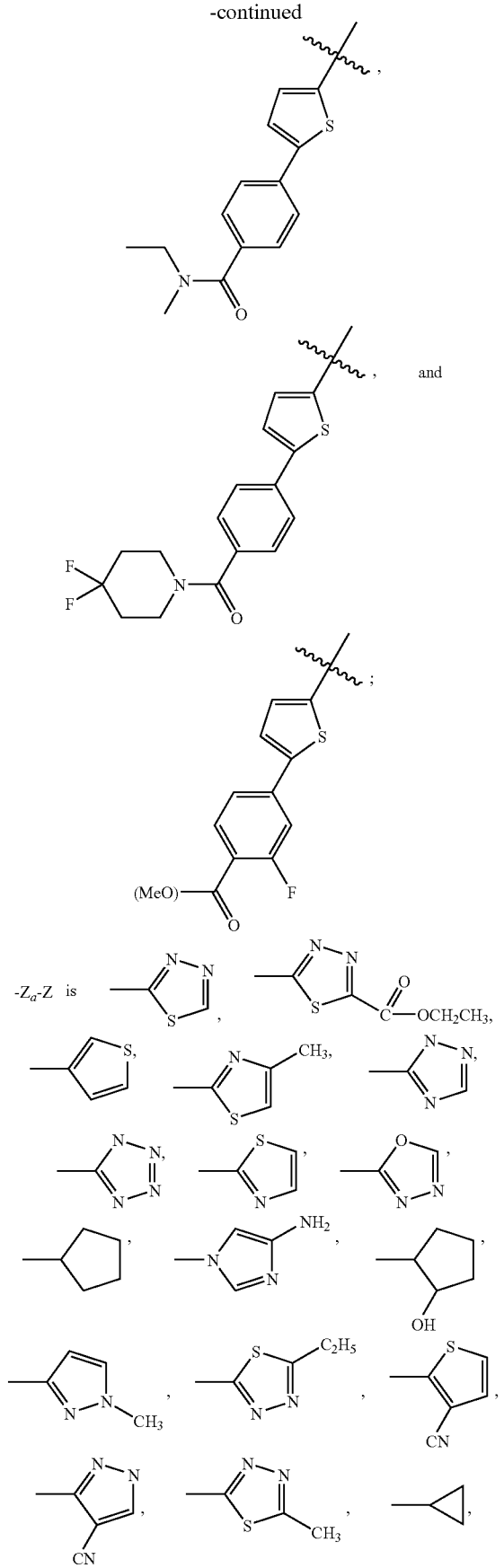
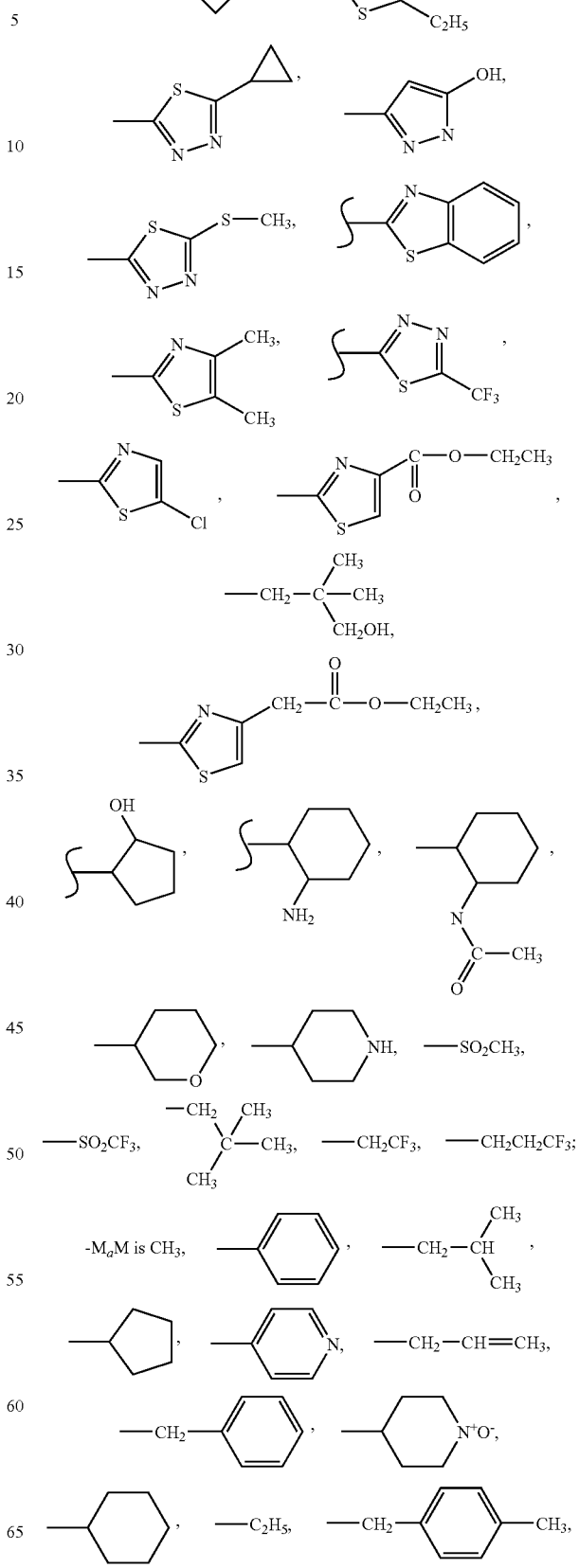

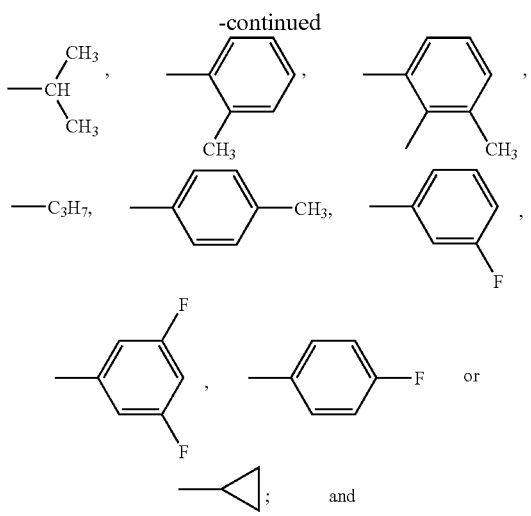

Q is H or CH₃;
or Q and R₆ together with the carbon atoms to which they are attached are combined to form

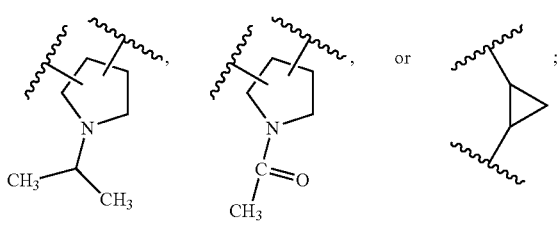

or Q and Mₐ-M together with the atom to which they are both attached are combined to form

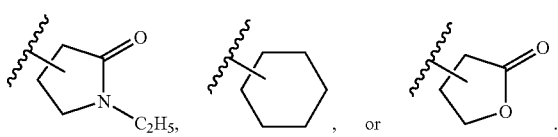

More preferred embodiments of compounds of formula (I) of the invention, have formula (Ia):

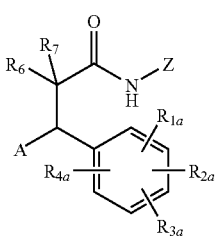

(Ia)

or an enantiomer, diastereomer, or a pharmaceutically-acceptable salt thereof, wherein:
A is thienyl, thiazolyl, isothiazolyl, thiadiazolyl, furanyl, pyrrolyl, pyrazolyl, pyridyl, or pyrimidinyl, each group optionally substituted by 1 to 4 groups, $R_1$, $R_2$, $R_3$, and/or $R_4$;

Z is selected from

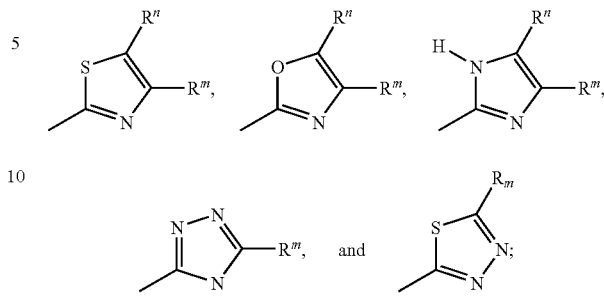

$R^m$ and $R^n$ at each occurrence are independently selected from (i) hydrogen, halogen, cycloalkyl, cyano, haloalkyl, thioalkyl, —CO₂R₂₃, —NR₂₃R₂₄, —C(=O)R₂₃, —C(O)N(R₂₃)(R₂₄), OR₂₃, $C_{1-4}$alkyl, substituted $C_{1-4}$alkyl, aryl, heteroaryl and heterocyclo; or (ii) $R^m$ and $R^n$ together with the atoms to which they are attached combine to form a fused 5- to 7-membered cycloalkyl, aryl, heteroaryl, or heterocyclo ring;

$R_1$, $R_2$, $R_3$, $R_4$, $R_{1a}$, $R_{2a}$, $R_{3a}$, and $R_{4a}$ are independently selected from (i) hydrogen, halogen, $C_{1-4}$alkyl, CN, $C_{2-4}$alkenyl, $C_{2-4}$alkynyl, SR₁₀, SO₂R₁₂, OR₁₀, $SO_p$NR₁₀R₁₁, and NR₁₀R₁₁; and/or (ii) $C_{0-3}$alkylene substituted by an optionally substituted group selected from phenyl and a 5- to 7-membered heterocyclo or heteroaryl;

$R_6$ is selected from $C_{1-4}$alkyl, $C_{1-4}$substituted alkyl, cyano, and $C_{3-7}$cycloalkyl;

$R_7$ is selected from hydrogen, $C_{1-4}$alkyl, $C_{1-4}$substituted alkyl, nitro, cyano, hydroxy, $C_{1-4}$alkoxy, and $C_{3-7}$cycloalkyl;

or $R_6$ and $R_7$ are taken together with the carbon to which they are attached to form a $C_{3-7}$cycloalkyl, group;

$R_{10}$ and $R_{11}$ at each occurrence are independently selected from (i) hydrogen, $C_{1-6}$alkyl, substituted $C_{1-6}$alkyl, and —SO₂($C_{1-4}$alkyl); and/or (ii) $C_{3-7}$cycloalkyl, heterocyclo, aryl, and heteroaryl, each is group optionally substituted; and/or (iii) $R_{10}$ is taken together with $R_{11}$ and the nitrogen atom to which they are both attached to form a 4- to 6-membered heteroaryl or heterocyclo, each group is optionally substituted;

$R_{12}$ at each occurrence is independently selected from an optionally substituted group selected from $C_{1-6}$alkyl, $C_{3-7}$cycloalkyl, heterocyclo, aryl, and heteroaryl; and $R_{23}$ and $R_{24}$ at each occurrence are independently selected from hydrogen, alkyl, substituted alkyl, C(=O)alkyl, CO₂(alkyl), SO₂alkyl, alkenyl, substituted alkenyl, alkynyl, substituted alkynyl, amino, aryl, heteroaryl, heterocyclo, and cycloalkyl.

Preferred compounds within the scope of formula (Ia) are those wherein A is thienyl or pyridyl optionally substituted by one to two groups selected from halogen, alkoxy, morpholinyl, piperidinyl, —NH(CH₂)ₙ(phenyl optionally substituted by $C_{1-4}$alkyl), pyrrolidinyl, furyl, and phenyl optionally substituted by one to two groups selected from halogen, alkoxy, $C_{1-6}$alkyl, CO₂R₁₀ or C(O)NR₁₀R₁₁; and n is 0, 1 or 2.

Other preferred compounds within the scope of formula (Ia) are those wherein A is selected from:
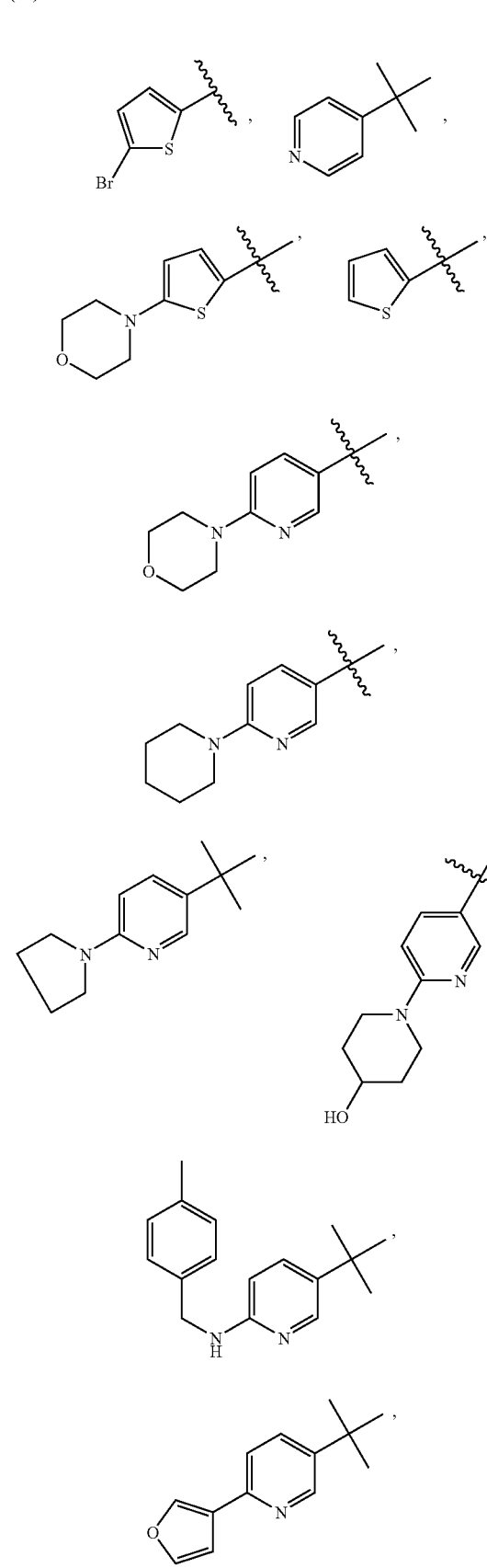
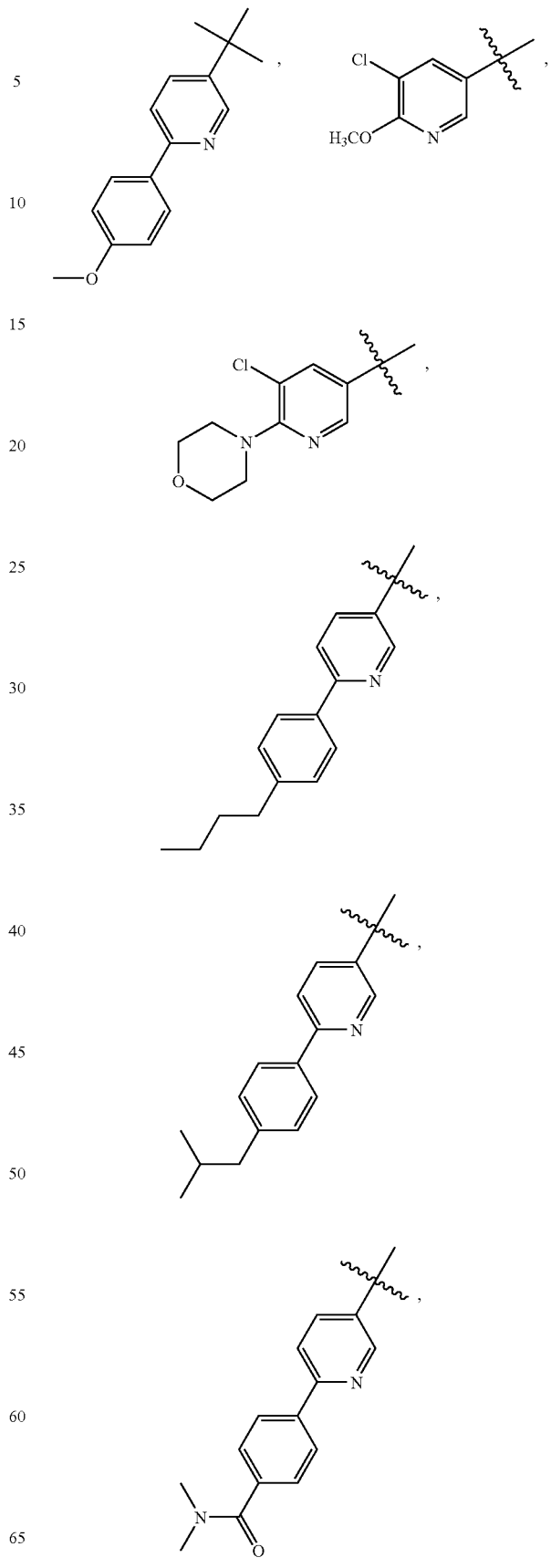

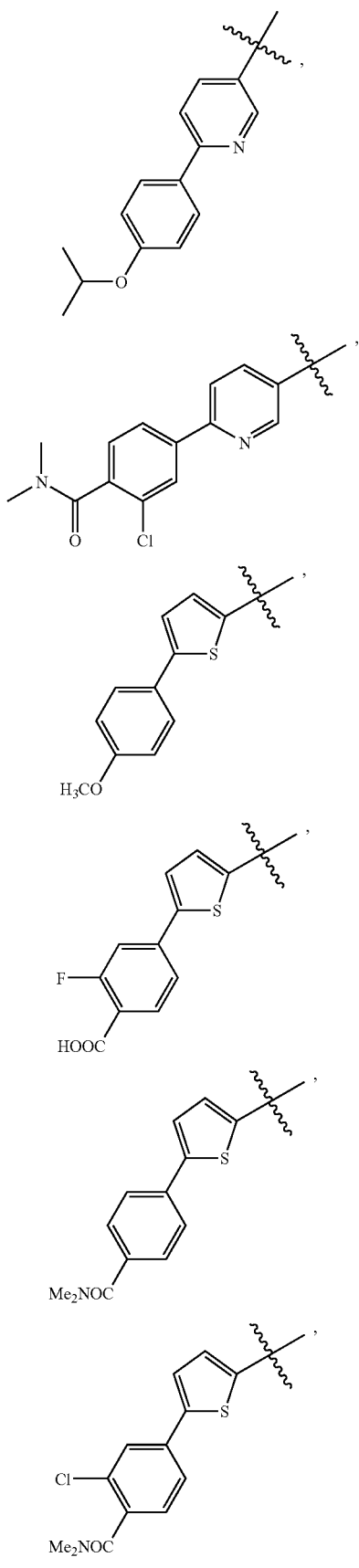
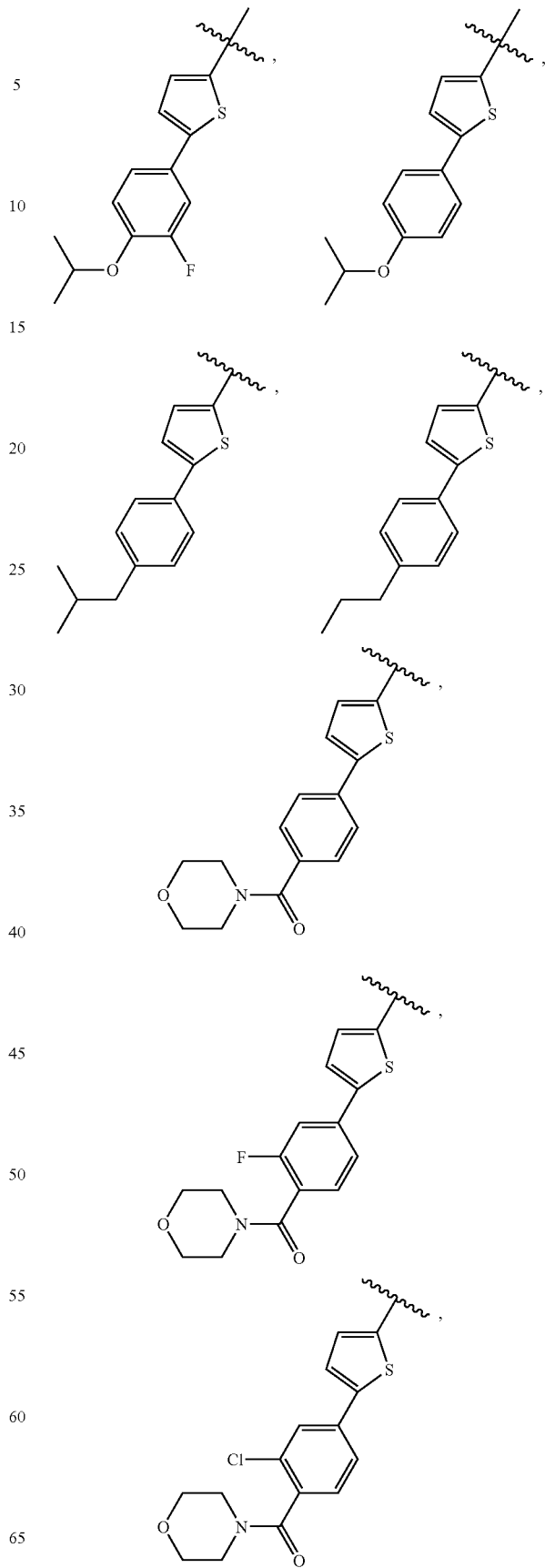

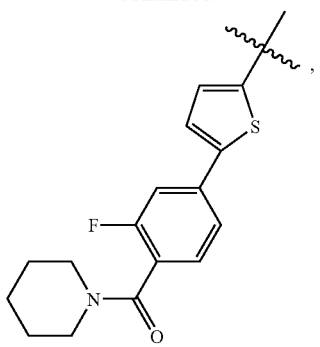
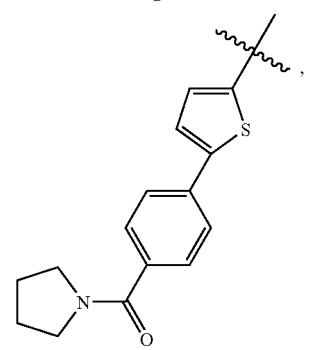
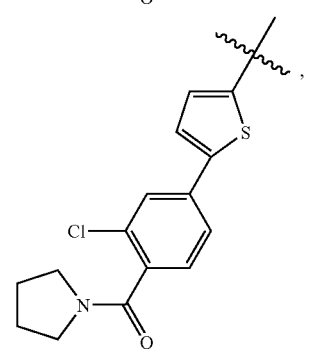
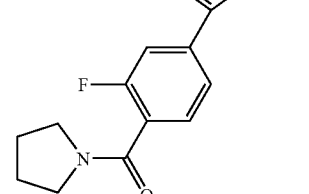
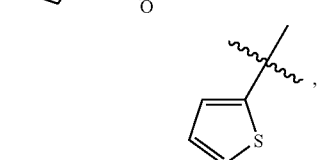
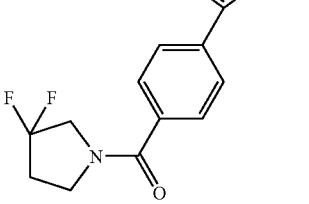
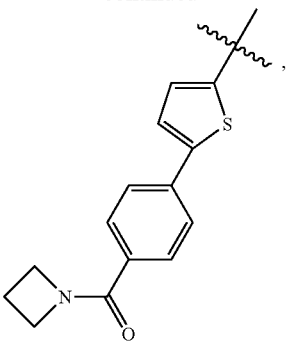
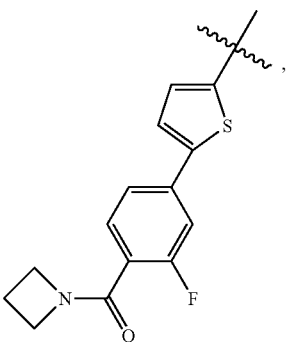
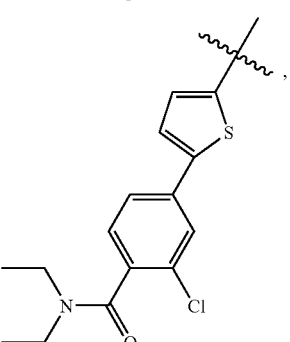
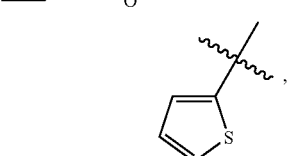
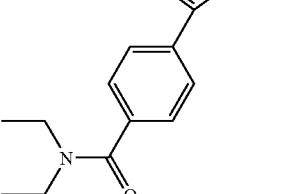
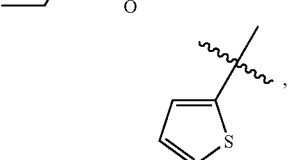
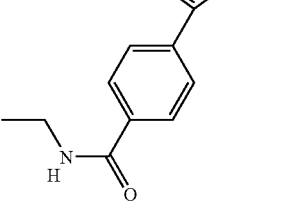

23
-continued
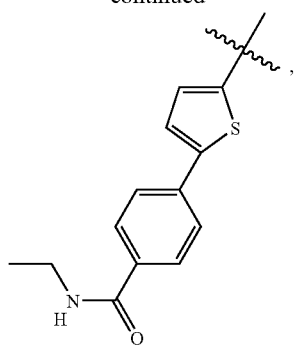
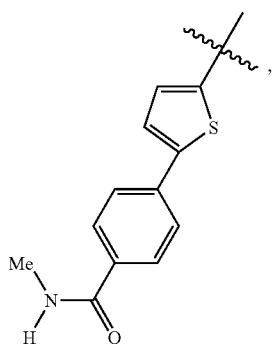
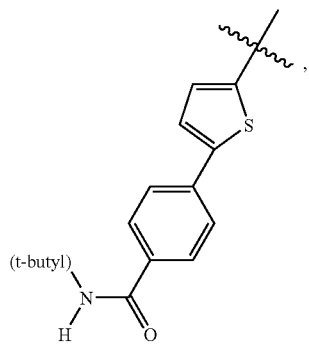
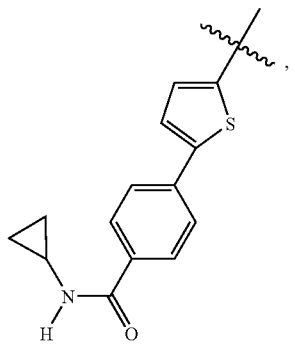
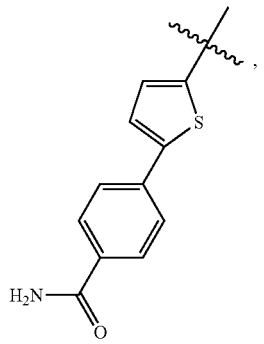
24
-continued
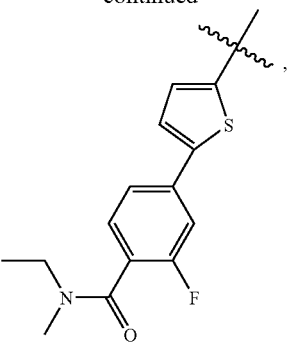
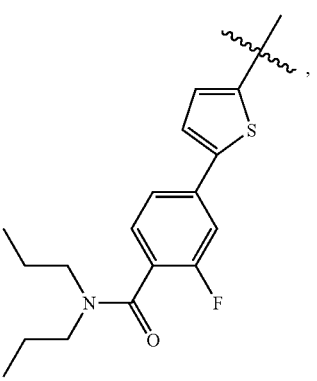
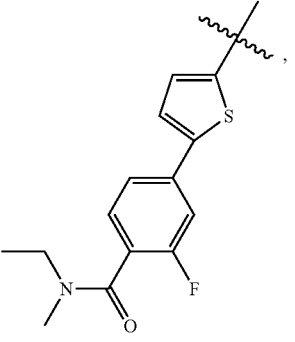
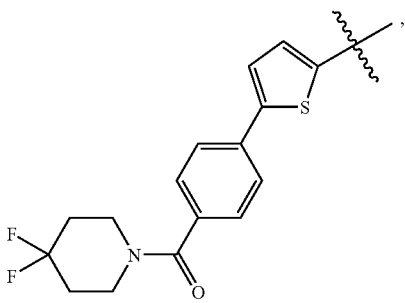, and
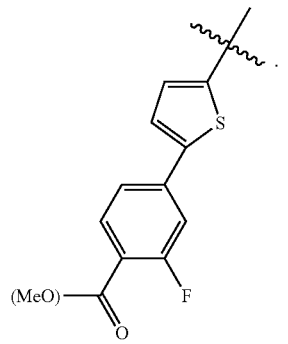

More preferred compounds within the scope of formula (Ia) are those wherein:
A has the formula

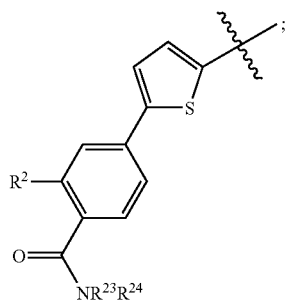

$R^2$ is hydrogen or halogen; and
$R^{23}$ and $R^{24}$ are selected independently from $C_{1-4}$alkyl; or
$R^{23}$ and $R^{24}$ taken together with the nitrogen atom to which they are attached combine to form an optionally substituted (preferred substitutents are halogen) 4 to 7-membered heterocyclo (more preferably morpholinyl).

Still other preferred compounds within the scope of formula (Ia) are those wherein $R_{1a}$, $R_{2a}$, $R_{3a}$, and $R_{4a}$ are selected from hydrogen, $C_{1-4}$alkyl, halogen, nitro, cyano, hydroxy, $C_{1-4}$alkoxy, morpholinyl, piperidinyl, piperazinyl, and pyrrolidinyl (more preferably $R_{3a}$, and $R_{4a}$ are both hydrogen; and $R_{1a}$ and $R_{2a}$ are independently hydrogen, methyl, fluoro, or morpholinyl).

Other preferred compounds within the scope of formula (Ia) are those wherein:
Z is selected from

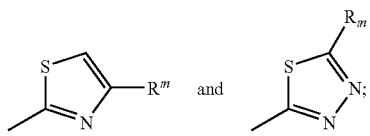

$R^m$ is hydrogen, $-CO_2R_{23}$, $-C(O)N(R_{23})(R_{24})$, or

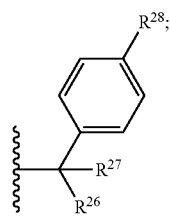

$R_{23}$ and $R_{24}$ at each occurrence are independently selected from hydrogen and $C_{1-4}$alkyl; or $R_{23}$ and $R_{24}$ together with the nitrogen atom to which they are attached form a 5- to 7-membered heterocyclo;
$R^{26}$ and $R^{27}$ are independently hydrogen, halogen, or hydroxy; or $R^{26}$ and $R^{27}$ combine to form =O; and
$R^{28}$ is $C_{1-4}$alkoxy; halogen, pyrimidinyl, isoxazolyl, pyrazolyl, or pyridinyl, each group optionally substituted by hydrogen, morpholinyl, $C_{1-4}$alkoxy, or $C_{1-4}$alkyl.

Other preferred compounds within the scope of formulae (I) and (Ia) are those $R_6$ is selected from $C_{1-4}$alkyl; and $R_7$ is selected from hydrogen and $C_{1-4}$alkyl (especially methyl).

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments. The present invention also provides a pharmaceutical composition comprising a compound of formula (I), or an enantiomer, diastereomer, or a pharmaceutically-acceptable salt, and a pharmaceutically acceptable carrier therefore.

Other embodiments of the present invention are a method of treating a disease or disorder comprising administering to a patient in need of treatment a therapeutically effective amount of a compound of formula (I), a compound of formula (I) for use in treating a disease or disorder, and use of a compound of formula (I) in the manufacture of a medicament for treating a disease or disorder, wherein the disease or disorder is selected from an endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease.

In still another embodiment, the present invention provides a method of treating endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease, a disease associated with the expression product of a gene whose transcription is stimulated or repressed by glucocorticoid receptors, or a disease associated with AP-1- and/or NFκB-induced transcription, or a disease associated with AP-1 and/or NFκB dependent gene expression, wherein the disease is associated with the expression of a gene under the regulatory control of AP-1 and/or NF-κB (particularly AP-1), including inflammatory and immune diseases and disorders as described hereinafter, which includes the step of administering a therapeutically effective amount of a compound of formula (I) of the invention to a patient.

Other embodiments of the present invention provide a method of treating a disease or disorder comprising administering to a patient in need of treatment a therapeutically effective amount of a compound of formula (I), a compound of formula (I) for use in treating a disease or disorder, and use of a compound of formula (I) in the manufacture of a medicament for treating a disease or disorder wherein the disease or disorder is selected from a metabolic disease or an inflammatory or immune disease comprising the administration to a patient in need of treatment, a therapeutically effective amount of a compound of formula (I).

A more preferred embodiment of the present invention provides a method of treating a disease or disorder comprising administering to a patient in need of treatment a therapeutically effective amount of a compound of formula (I), a compound of formula (I) for use in treating a disease or disorder, and use of a compound of formula (I) in the manufacture of a medicament for treating a disease or disorder wherein the disease or disorder is selected from a metabolic disease wherein the disease is a metabolic disease selected from Type I diabetes, Type II diabetes, juvenile diabetes, and obesity.

Other preferred embodiments of the present invention are a method of treating a disease or disorder comprising administering to a patient in need of treatment a therapeutically effective amount of a compound of formula (I), a compound of formula (I) for use in treating a disease or disorder, and use of a compound of formula (I) in the manufacture of a medicament for treating a disease or disorder, wherein the disease or disorder is an inflammatory or immune disease selected from transplant rejection of kidney, liver, heart, lung, pancreas, bone marrow, cornea, small bowel, skin allografts, skin homografts, heart valve xenograft, serum sickness, and graft vs. host disease, rheumatoid arthritis, psoriatic arthritis, multiple sclerosis, asthma, inflammatory bowel disease, Crohn's disease, ulcerative colitis, pyoderma gangrenum, systemic lupus erythematosis, myasthenia gravis, psoriasis, dermatitis, dermatomyositis, eczema, seborrhoea, pulmonary inflammation, eye uveitis, hepatitis, Graves' disease, Hashimoto's thyroiditis, autoimmune thyroiditis, Behcet's or Sjorgen's syndrome, pernicious or immunohaemolytic anaemia, atherosclerosis, Addison's disease, idiopathic adrenal insufficiency, autoimmune polyglandular disease, glomerulonephritis, scleroderma, morphea, lichen planus, vitiligo, alopecia greata, autoimmune alopecia, autoimmune hypopituitarism, Guillain-Barre syndrome, alveolitis, contact hypersensitivity, delayed-type hypersensitivity, contact dermatitis, uticaria, skin allergies, respiratory allergies, hayfever, gluten-sensitive enteropathy, osteoarthritis, acute pancreatis, chronic pancreatitis, acute respiratory distress syndrome, Sezary's syndrome, restenosis, stenosis, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetitformis, severe erythema multiforme, exfoliative dermatitis, seborrheic dermatitis, seasonal or perennial allergic rhinitis, bronchial asthma, atopic dermatitis, drug hypersensitivity reactions, allergic conjuncivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, sepsis, and chronic obstructive pulmonary disease.

Especially preferred embodiments are a method of treating a disease or disorder comprising administering to a patient in need of treatment a therapeutically effective amount of a compound of formula (I), a compound of formula (I) for use in treating a disease or disorder, and use of a compound of formula (I) in the manufacture of a medicament for treating a disease or disorder where the disease or disorder is selected from transplant rejection, rheumatoid arthritis, psoriatic arthritis, multiple sclerosis, asthma, inflammatory bowel disease, systemic lupus erythematosis, and psoriasis.

Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κB— (particularly AP-1-) induced transcription, or a method for treating a disease or disorder associated with AP-1 and/or NF-κB (particularly AP-1) dependent gene expression, wherein the disease is associated with the expression of a gene under the regulatory control of AP-1 and/or NF-κP (particularly AP-1), such as inflammatory and immune disorders, cancer and tumor disorders, such as solid tumors, lymphomas and leukemia, and fungal infections such as mycosis fungoides.

In still another embodiment, the present invention provides a pharmaceutical combination comprising one or more compounds of formula (I) and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

Even more preferred combinations are those wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, N,N-2344, L895645, YM-440, R-119702, AJ9677, repaglinide, nateglinide, KAD1129, AR-HO39242, GW-409544, KRP297, AC2993, LY315902, P32/98 and/or NVP-DPP-728A, wherein the anti-obesity agent is orlistat, ATL-962, AJ9677, L750355, CP331648, sibutramine, topiramate, axokine, dexamphetamine, phentermine, phenylpropanolamine, and/or mazindol, wherein the lipid lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427, wherein the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl)amino]-2, 2-dimethyl-7-oxo-1H-azepine-1-acetic acid (gemopatrilat) or CGS 30440;

an angiotensin II receptor antagonist which is irbesartan, losartan or valsartan;

amlodipine besylate, prazosin HCl, verapamil, nifedipine, nadolol, propranolol, carvedilol, or clonidine HCl, wherein the platelet aggregation inhibitor is aspirin, clopidogrel, ticlopidine, dipyridamole or ifetroban;

the immunosuppressant is a cyclosporin, mycophenolate, interferon-beta, deoxyspergolin, FK-506 or Ant.-IL-2;

the anti-cancer agent is azathiprine, 5-fluorouracel, cyclophosphamide, cisplatin, methotrexate, thiotepa, or carboplatin;

the anti-viral agent is abacavir, aciclovir, ganciclovir, zidanocin, or vidarabine; and the antiinflammatory drug is ibuprofen, celecoxib, rofecoxib, aspirin, naproxen, ketoprofen, diclofenac sodium, indomethacin, piroxicam, prednisone, dexamethasone, hydrocortisone, or triamcinolone diacetate.

The term "disease associated with GR transactivation," as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary andrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

The terms "glucocorticoid receptor" and "GR," as used herein, refer either to a member of the nuclear hormone receptor ("NHR") family of transcription factors which bind glucocorticoids and either stimulate or repress transcription, or to GR-beta.

These terms, as used herein, refer to glucocorticoid receptor from any source, including but not limited to: human glucocorticoid receptor as disclosed in Weinberger, et al., Science, 228:740-742 (1985), and in Weinberger, et al., Nature, 318:670-672 (1986); rat glucocorticoid receptor as disclosed in Miesfeld, R., Nature, 312:779-781 (1985); mouse glucocortoid receptor as disclosed in Danielson, M. et al., EMBO J., 5:2513; sheep glucocorticoid receptor as disclosed in Yang, K. et al., J. Mol. Endocrinol., 8:173-180 (1992); marmoset glucocortoid receptor as disclosed in Brandon, D. D. et al., J. Mol. Endocrinol. 7:89-96 (1991); and human GR-beta as disclosed in Hollenberg, S. M. et al., Nature, 318:635 (1985); Bamberger, C. M. et al., J. Clin Invest., 95:2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Graves' disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia greata, autoimmune alopecia, autoimmune hypopituatarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and artherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis.

Synthesis

The compounds of the present invention can be prepared according to procedures well known to one skilled in the art of organic synthesis. The compounds of the present invention can be synthesized using the methods described below together with synthetic methods known in the art of organic chemistry, or variations thereon, as appreciated by those skilled in the art.

The reactions presented in the Schemes below are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are performed under standard reaction conditions, which are readily recognized by one skilled in the art. One of skill in the art also understands that the reagents and reactions chosen must be compatible with the functionality present on various portions of the molecule.

In some circumstances, various steps in the synthesis may be performed in alternate sequential order to give the desired compound or compounds. Examples of compounds of the present invention prepared by methods described in the general schemes are given in the preparations and examples section set out hereinafter. Example compounds are typically prepared as racemic mixtures. Preparation of homochiral examples may be carried out according to techniques known to one skilled in the art. For example, homochiral compounds may be prepared by the separation of racemic products by chiral phase preparative HPLC. Alternatively, example compounds may be prepared by methods known to give enantiomerically enriched products. These include, but are not limited to, the incorporation of chiral auxiliary functionalities into racemic intermediates which serve to control the diaststereoselectivity of transformations, providing enantio-enriched products upon cleavage of the chiral auxiliary.

In following schemes, the various groups A, M, $M_a$, Z, $Z_a$ and $R_{22}$ correspond to those described above in for formula (I):

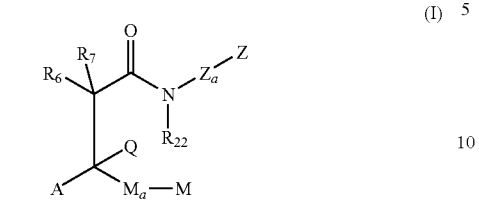
(I)

Scheme A

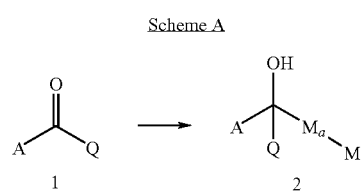

Compounds of formula 2 are constructed by the addition of an organometallic compound M-$M_a$-"metal" to the compound of formula 1 by one of the methods well known to those skilled in the art. The term "metal" is MgBr, MgCl or Li, wherein each metal prepared from the corresponding bromide or chloride. Alternatively, compounds of formula 2 can be constructed by the addition of an organometallic compound A-"metal" to a compound, $MM_aCOQ$, in a manner similar to that described above.

Scheme B

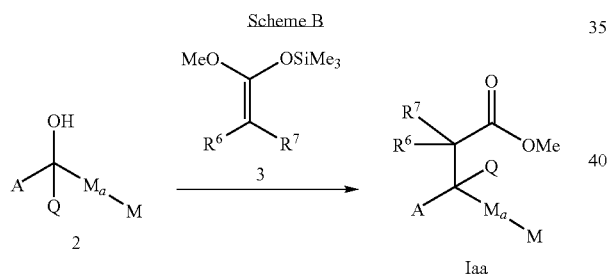

A compound of formula 2 can be reacted with a compound of formula 3 in the presence of a Lewis acid such as $TiCl_4$ or $SnCl_4$, in an appropriate solvent such as dichloromethane, 1,2-dichloroethan or THF, at temperatures ranging from −78° C. to room temperature, to form compound of formula (Iaa). The A group in (Ia) may also be further elaborated by methods well known to those of skill in the art.

Scheme C

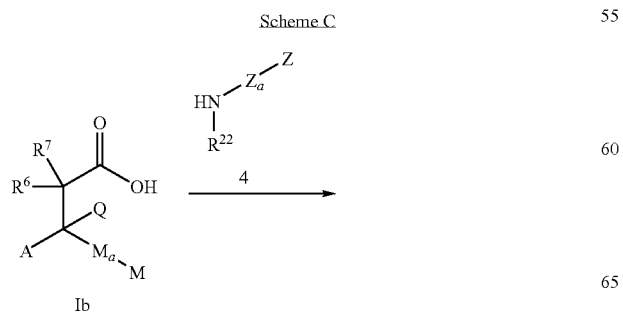

-continued

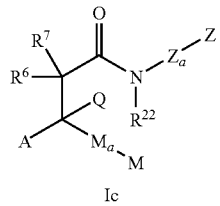

A compound of formula (Ib), prepared from compound of formula (Iaa) via basic hydrolysis, may be reacted with an amine of formula 4 by one of the many methods of amidation well known to those skilled in the art to provide compound of formula (Ic) of the invention. For example, a compound of formula (Ib) in a suitable solvent such as acetonitrile may be treated with 1-[3-(dimethylamino)propyl]-3-ethylcarbodiimide hydrochloride (EDC), 1-hydroxy-7-azabenzotriazole, triethylamine and amine 4 to form a compounds of formula (Ic). The A group in formula (Ic) may also be further elaborated by methods well known to those of skill in the art.

Scheme D

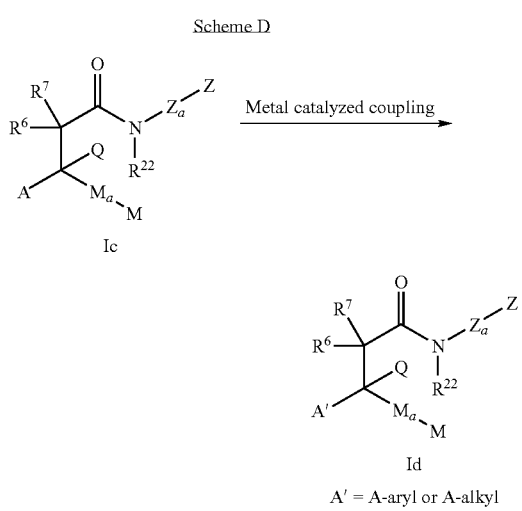

A' = A-aryl or A-alkyl

A compound of formula (Ic) that contains at least one halogen atom (I, Br and/or Cl) or a OTf (triflate) group located on the A group undegoes metal (such as palladium) catalyzed coupling reaction with an organometallic compound (such as an organoboron or organostannic compound) using one of the methods well known to those skilled in the art to provide a compound of formula (Id) where the A group is substituted by an aryl or alkyl group.

Scheme E

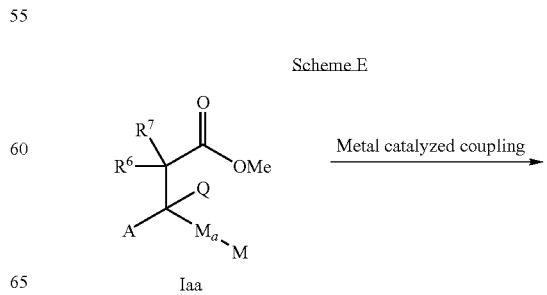

-continued

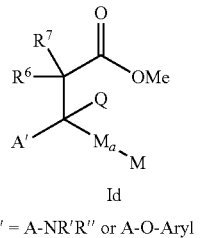

Id

A' = A-NR'R'' or A-O-Aryl

A compound of formula (Iaa) that contains at least one halogen atom (I, Br and Cl) or a OTf (triflate) group located on the A group can undergo a metal (such as palladium) catalyzed coupling reaction with an amine (NHR'R'') or Aryl-OH to provide a compound of formula (Id) where A group is connected with an NR'R'' or O-Aryl. See e.g., S. Buchwald, et al., *Acc. Chem. Res.* 31, pp. 805 (1998) and *J. Org. Chem.* 65, pp. 1158 (2000)

It should be understood that protecting groups may be utilized as appropriate throughout synthetic Schemes described above. Common protecting groups for amine-containing heterocycles are ureas, sulfonamides, carbamates, and alkyl groups (such as benzyl). The judicious use of protecting groups is known to one skilled in the art and is described in Greene and Wuts "Protecting Groups in Organic Synthesis 3rd Ed. ©1999.

DEFINITIONS

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 6 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$) hydroxyalkyl includes hydroxy, hydroxymethyl and hydroxyethyl.

The term "substituted alkyl" refers to an alkyl group as defined above having one, two, or three substituents selected from the group consisting of halo (e.g., trifluoromethyl), alkenyl, substituted alkenyl, alkynyl, nitro, cyano, oxo (=O), $OR_a$, $SR_a$, (=S), $-NR_aR_b$, $-N(alkyl)_3^+$, $-NR_aSO_2$, $-NR_aSO_2R_c$, $-SO_2R_c$, $-SO_2NR_aR_b$, $-SO_2NR_aC(=O)R_b$, $SO_3H$, $-PO(OH)_2$ $-OC(O)R_a$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, $CO_2H$, $CO_2(alkyl)$, $C_{3-7}$cycloalkyl, phenyl, benzyl, phenylethyl, napthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being selected from the group consisting of ($C_{1-6}$)alkyl, ($C_{2-6}$)alkenyl, hydroxy, halogen, cyano, nitro, =O (as valence allows), $CF_3$, $O(C_{1-6}$alkyl), $OCF_3$, C(=O)H, C(=O)($C_{1-6}$alkyl), $CO_2H$, $CO_2(C_{1-6}$alkyl), $NHCO_2(C_{1-6}$ alkyl), —S($C_{1-6}$alkyl), —$NH_2$, NH($C_{1-6}$alkyl), N($C_{1-6}$ alkyl)$_2$, N($CH_3$)$_3^+$, $SO_2(C_{1-6}$alkyl), C(=O)($C_{1-4}$alkylene) $NH_2$, C(=O)($C_{1-4}$alkylene)NH(alkyl), C(=O)($C_{1-4}$alkylene)N($C_{1-4}$alkyl)$_2$, $C_{3-7}$cycloalkyl, phenyl, benzyl, phenylethyl, phenyloxy, benzyloxy, napthyl, a four to seven membered heterocyclo or cycloalkyl, or a five to six membered heteroaryl. When a substituted alkyl is substituted with an aryl (including, for example, phenyl and napthyl), heterocyclo, cycloalkyl, or heteroaryl group, said ringed systems are as defined below and thus may have zero, one, two, or three substituents, also as defined below.

One skilled in the field will understand that, when the designation "$CO_2$" is used herein, this is intended to refer to the group

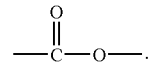

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl ($C_{0-4}$)alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., $\{-CH_2-\}_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substitutents as defined above for substituted alkyl groups.

The term "heteroalkylene" is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —SO$_2$—, —NH—, and —NHSO$_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—(CH$_2$)$_{1-5}$NH—CH$_2$—,   —O—(CH$_2$)$_{1-5}$S(=O)—

CH$_2$—, —NHSO$_2$—CH$_2$—, —CH$_2$—NH—, and so forth. Preferably, a heteroalkylene does not have two adjacent atoms simultaneously selected from —O— and —S—. When a subscript is used with the term heteroalkylene, e.g., as in C$_{2-3}$heteroalkylene, the subscript refers to the number of carbon atoms in the group in addition to heteroatoms. Thus, for example, a C$_{1-2}$heteroalkylene may include groups such as —NH—CH$_2$—, —CH$_2$—NH—CH$_2$—, —CH$_2$—CH$_2$—NH—, —S—CH$_2$—, —CH$_2$—S—CH$_2$—, —O—CH$_2$—NH—CH$_2$—, CH$_2$—O—CH$_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or A$_1$-Q-A$_2$-R$_h$, wherein A$_1$ is a bond, C$_{1-2}$alkylene, or C$_{2-3}$alkenylene; Q is a bond, —C(=O)—, —C(=O)NR$_d$—, —C(=S)NR$_d$—, —SO$_2$—, —SO$_2$NR$_d$—, —CO$_2$—, or —NR$_d$CO$_2$—; A$_2$ is a bond, C$_{1-3}$alkylene, C$_{2-3}$alkenylene, —C$_{1-4}$alkylene-NR$_d$—, —C$_{1-4}$alkylene-NR$_d$C(=O)—, —C$_{1-4}$alkylene-S—, —C$_{1-4}$alkylene-SO$_2$—, or —C$_{1-4}$alkylene-O—, wherein said A$_2$ alkylene groups are branched or straight chain and optionally substituted as defined herein for substituted alkylene; R$_h$ is hydrogen, alkyl, substituted alkyl, alkenyl, substituted alkenyl, aryl, heteroaryl, heterocyclo, or cycloalkyl; and R$_d$ is selected from hydrogen, alkyl, and substituted alkyl, as defined herein, provided, however, that for a substituted heteroalkylene R$_h$ is not hydrogen when A$_1$, Q and A$_2$ are each bonds. When R$_h$ is aryl, heteroaryl, cycloalkyl, or heterocyclo, these rings are, in turn, optionally substituted with one to three groups as defined below in the definitions for these terms.

The term "alkoxy" refers to an oxygen atom substituted by alkyl or substituted alkyl, as defined herein. For example, the term "alkoxy" or includes the group —O—C$_{1-6}$alkyl.

The term "alkylthio" refers to a sulfur atom that is substituted by an alkyl or substituted alkyl group as defined herein. For example, the term "thioalkyl" includes the group —S—C$_{1-6}$alkyl, and so forth.

The term "alkylamino" refers to an amino group substituted with an alkyl group or substituted alkyl group as defined above. For example, the term "alkylamino" includes the group —NR—C$_{1-12}$alkyl. (where R is preferably hydrogen but may include alkyl or substituted alkyl as defined above.)

When a subscript is used with reference to an alkoxy, thioalkyl or aminoalkyl, the subscript refers to the number of carbon atoms that the group may contain in addition to heteroatoms. Thus, for example, monovalent C$_{1-2}$-aminoalkyl includes the groups —CH$_2$—N(CH$_3$)$_2$, and —(CH$_2$)$_2$—NH$_2$. A lower aminoalkyl comprises an aminoalkyl having one to four carbon atoms. The term (C$_{1-4}$alkyl)$_{0-2}$amino includes the groups NH$_2$, —NH(C$_{1-4}$alkyl), and —N(C$_{1-4}$alkyl)$_2$. "Amino" refers to the group NH$_2$. A "substituted amino" refers to an amino group substituted as described above for the nitrogen atom of a heteroalkylene chain and includes, for example, the terms alkylamino and acylamino (—NR$_d$C(O)R$_e$).

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—C$_{1-12}$alkyl, whereas a bivalent alkoxy includes groups such as —O—C$_{1-12}$alkylene-.

It should be understood that the selections for all groups, including for examples, alkoxy, thioalkyl, and aminoalkyl, will be made by one skilled in the field to provide stable compounds. Thus, for example, in compounds of formula (I), when G is attached to a nitrogen atom (N*) of ring A and is selected from an alkoxy or alkylthio group, the alkoxy and alkylthio groups will have at least one carbon atom bonded directly to ring A (at N*), with the oxygen or sulfur atoms being at least one atom away from said nitrogen atom.

The term "carbonyl" refers to a bivalent carbonyl group —C(=O)—. When the term "carbonyl" is used together with another group, such as in "heterocyclocarbonyl", this conjunction defines with more specificity at least one of the substituents that the substituted carbonyl will contain. For example, "heterocyclocarbonyl" refers to a carbonyl group as defined above where at least one of the substituents is an heterocyclo, such as morpholinyl.

The term "acyl" refers to a carbonyl group linked to an organic radical, more particularly, the group C(=O)R$_e$. The group R$_e$ can be selected from alkyl, alkenyl, alkynyl, aminoalkyl, substituted alkyl (i.e. substituted alkylene), substituted alkenyl, substituted alkynyl, cycloalkyl, heterocyclo, aryl, or heteroaryl, as defined herein. When R$_e$ is aryl, heteroaryl, cycloalkyl, or heterocyclo, these rings are, in turn, optionally substituted with one to three groups as defined below in the definitions for these terms.

The term "alkoxycarbonyl" refers to a carboxy group

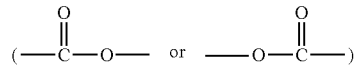

linked to an organic radical (CO$_2$R$_e$), as well as the bivalent groups —CO$_2$—, —CO$_2$R$_e$— which are linked to organic radicals in compounds of formula (I), wherein R$_e$ is as defined above for acyl. The organic radical to which the carboxy group is attached may be monovalent (e.g., —CO$_2$-alkyl or —OC(=O)alkyl), or bivalent (e.g., —CO$_2$-alkylene, —OC(=O)alkylene, etc.) Accordingly, in compounds of formula (I), when it is recited that G can be "alkoxycarbonyl," this is intended to encompass a selection for G of —CO$_2$— and also the groups —CO$_2$R$_e$— or —R$_e$CO$_2$—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "carboxamide", "carboxamidyl", or "carboxamido" refers to the group —NR$_d$C(=O)R$_e$, wherein the groups R$_d$ and R$_e$ are defined as recited above in the definitions for heteroalkyl, alkoxycarbonyl and acyl. For example, the group

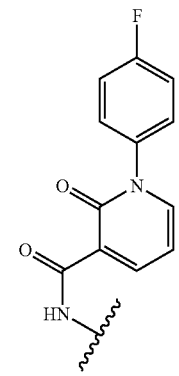

is a carboxamido group where R$_e$ is a substituted heterocyclo according to the definitions herein.

The term "amide", "amidyl", or "amido" refers to the group —C(=O)NR$_a$R$_b$, wherein the groups R$_a$ and R$_b$ are defined as recited above in the definition for substituted alkyl groups.

The term "urea" refers to the group —NR$_d$C(=O)NR$_a$R$_b$, wherein the groups R$_a$, R$_b$, and R$_d$ are defined as recited above in the definition for substituted alkyl groups. Additionally, the urea group may be bivalent, in which case one of the groups R$_a$ and R$_b$ will be a bond. Thus, in compounds of formula (I), when it is stated that G may be urea, it can mean that G is a group —NR$_d$(C(=O)NR$_a$— where appropriate.

The term "sulfonyl" refers to a sulphoxide group linked to an organic radical in compounds of formula (I), more particularly, the monovalent group —S(O)$_2$—R$_e$. Additionally, the sulfonyl group may be bivalent, in which case R$_e$ is a bond. Accordingly, in compounds of formula (I), when it is recited that G can be "sulfonyl," it can mean that G is a group —S(O) where appropriate. The group R$_e$ is selected from those recited above for acyl and alkoxycarbonyl groups, with the exception that R$_e$ is not hydrogen.

The terms "sulfonamide", "sulfonamidyl", or "sulfonamido" refers to the group —S(O)$_2$NR$_a$R$_b$, wherein R$_a$ and R$_b$ are as defined above for substituted alkyl groups.

The term "cycloalkyl" refers to fully saturated and partially unsaturated hydrocarbon rings (and therefore includes hydrocarbon rings also known as "cycloalkenyl rings") of 3 to 9, preferably 3 to 7 carbon atoms. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$, —SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$, R$_b$ and R$_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of (C$_{1-4}$)alkyl, (C$_{2-4}$)alkenyl, (C$_{2-4}$)alkynyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3^+$, SO$_2$(C$_{1-4}$alkyl), C(=O)(C$_{1-4}$alkylene)NH$_2$, C(=O)(C$_{1-4}$alkylene)NH(alkyl), C(=O)(C$_{1-4}$alkylene)N(C$_{1-4}$alkyl)$_2$ and/or phenyl optionally substituted with any of the preceeding groups. As valence allows, if said further ring is cycloalkyl or heterocyclo it is additionally optionally substituted with =O (oxo).

Accordingly, in compounds of formula (I), the term "cycloalkyl" includes cyclopropyl, cyclobutyl, cyclopentyl, cyclohexyl, cycloheptyl, bicyclooctyl, etc., as well as the following ring systems,

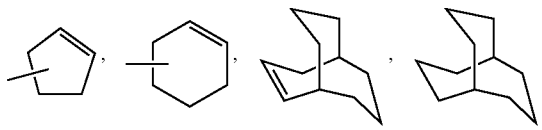

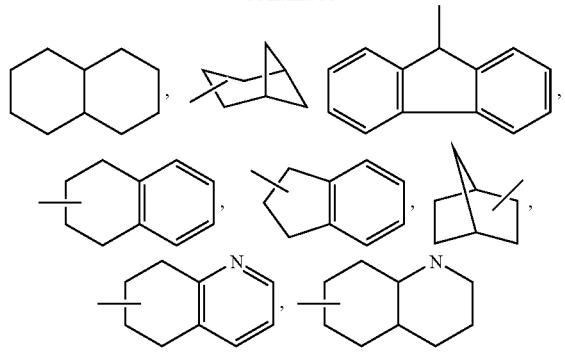

and the like, which optionally may be substituted at any available atoms of the ring(s). Preferred cycloalkyl groups include cyclopropyl, cyclopentyl, cyclohexyl, and

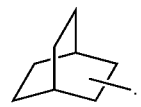

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

The term "aryl" refers to phenyl, biphenyl, fluorenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, OR$_a$, SR$_a$, (=S), SO$_3$H, —NR$_a$R$_b$, —N(alkyl)$_3^+$, —NR$_a$SO$_2$, —NR$_a$SO$_2$R$_c$, —SO$_2$R$_c$—SO$_2$NR$_a$R$_b$, SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, aryl, cycloalkyl, heterocyclo, and/or heteroaryl, wherein R$_a$, R$_b$ and R$_c$ are as defined above for substituted alkyl groups, and are also in turn optionally substituted as recited above. Additionally, two substituents attached to an aryl, particularly a phenyl group, may join to form a further ring such as a fused or spiro-ring, e.g. cyclopentyl or cyclohexyl, or fused heterocyclo or heteroaryl. When an aryl is substituted with a further ring (or has a second ring fused thereto), said ring in turn is optionally substituted with one to two of (C$_{1-4}$)alkyl, (C$_{2-4}$)alkenyl, (C$_{2-4}$)alkynyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3^+$, SO$_2$(C$_{1-4}$alkyl), C(=O)(C$_{1-4}$alkylene)NH$_2$, C(=O)(C$_{1-4}$alkylene)NH(alkyl), C(=O)(C$_{1-4}$alkylene)N(C$_{1-4}$alkyl)$_2$ and/or phenyl optionally substituted with any of the preceeding groups. As valence allows, if said further ring is cycloalkyl or heterocyclo it is additionally optionally substituted with =O (oxo).

Thus, examples of aryl groups include:

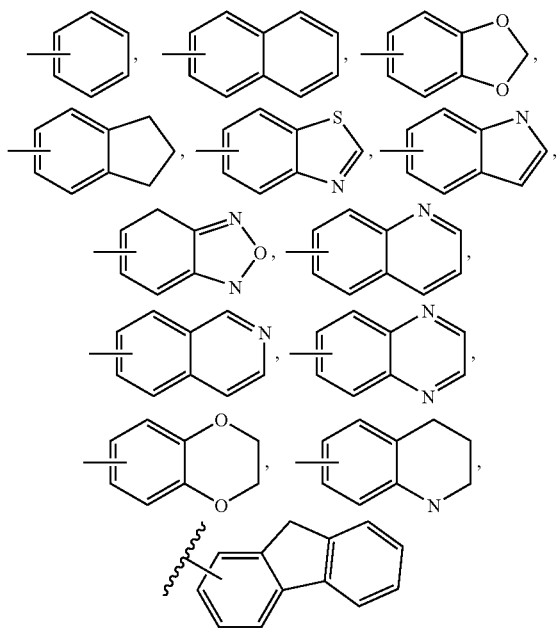

(fluorenyl) and the like, which optionally may be substituted at any available carbon or nitrogen atom. A preferred aryl group is optionally-substituted phenyl.

The terms "heterocycloalkyl", "heterocyclo" or "heterocyclic" may be used interchangeably and refer to substituted and unsubstituted non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$, —SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$, R$_b$ and R$_c$ are as defined above for substituted alkyl groups, and are also in turn optionally substituted as recited above. When a heterocyclo is substituted with a further ring, said ring in turn is optionally substituted with one to two of (C$_{1-4}$)alkyl, (C$_{2-4}$)alkenyl, (C$_{2-4}$)alkynyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3^+$, SO$_2$(C$_{1-4}$alkyl), C(=O)(C$_{1-4}$alkylene)NH$_2$, C(=O)(C$_{1-4}$alkylene)NH(alkyl), C(=O)(C$_{1-4}$alkylene)N(C$_{1-4}$alkyl)$_2$ and/or phenyl optionally substituted with any of the preceeding groups. As valence allows, if said further ring is cycloalkyl or heterocyclo it is additionally optionally substituted with =O (oxo).

Monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Heterocyclo groups in compounds of formula (I) include

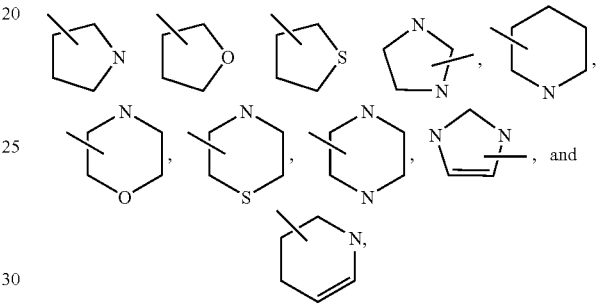

which optionally may be substituted.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$, —SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, aryl, cycloalkyl, heterocyclo, and/or heteroaryl, wherein R$_a$, R$_b$ and R$_c$ are as defined above for substituted alkyl groups, and are also in turn optionally substituted as recited above. When a heteroaryl is substituted with a further ring, said ring in turn is optionally substituted with one to two of (C$_{1-4}$)alkyl, (C$_{2-}$ 4)alkenyl, (C$_{2-4}$)alkynyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3^+$, SO$_2$(C$_{1-4}$ alkyl), C(=O)(C$_{1-4}$alkylene)NH$_2$, C(=O)(C$_{1-4}$alkylene)NH (alkyl), C(=O)(C$_{1-4}$alkylene)N(C$_{1-4}$alkyl)$_2$ and/or phenyl optionally substituted with any of the preceeding groups. As valence allows, if said further ring is cycloalkyl or heterocyclo it is additionally optionally substituted with =O (oxo).

Monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrolinyl, acridinyl, phenanthridinyl, xanthenyl and the like.

In compounds of formula (I), preferred heteroaryl groups include

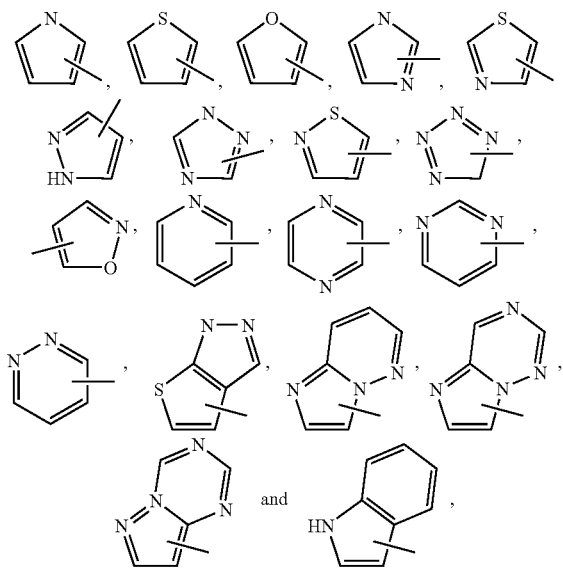

and the like, which optionally may be substituted at any available carbon or nitrogen atom. Aromatic rings may also be designated by an unbroken circle in the ring.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl,) unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

When the term "optionally substituted" is used herein to refer to a ring or group, the ring or group may be substituted or unsubstituted.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula (I) can form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Prodrugs and solvates (e.g. hydrates) of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) *Design of Prodrugs*, edited by H. Bundgaard, (Elsevier, 1985) and *Methods in Enzymology*, Vol. 112, pp. 309-396, edited by K. Widder, et al. (Academic Press, 1985);
b) *A Textbook of Drug Design and Development*, edited by Krosgaard-Larsen and H. Bundgaard, Chapter 5, "Design and Application of Prodrugs," by H. Bundgaard, pp. 113-191 (1991); and
c) H. Bundgaard, *Advanced Drug Delivery Reviews*, Vol. 8, pp. 1-38 (1992), each of which is incorporated herein by reference.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization.

Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, anti-obesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula I of the invention include cyclosporins, for example cyclosporin A, mycophenolate, interferon-beta, deoxyspergolin, FK-506 or Ant.-IL-2.

The anti-cancer agents which may be optionally employed in combination with compounds of formula I of the invention include azathiprine, 5-fluorouracil, cyclophosphamide, cisplatin, methotrexate, thiotepa, carboplatin, and the like.

The anti-viral agents which may be optionally employed in combination with compounds of formula I of the invention include abacavir, aciclovir, ganciclovir, zidanocin, vidarabine, and the like.

The anti-inflammatory agents which may be optionally employed in combination with compounds of formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g. CD40Ig and CD8gp39), inhibitors, such as nuclear translocation inhibitors, of NF-kappa B function, such as deoxyspergualin (DSG).

The anti-fungal agents which may be optionally employed in combination with compounds of formula I of the invention include fluconazole, miconazole, amphotericin B, and the like.

The antibiotics which may be optionally employed in combination with compounds of formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula I of the invention include methotrexate, leflunomide, FK506 (tacrolimus, Prograf).

The hypolipidemic agent or lipid-lowering agent or lipid modulating agents which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

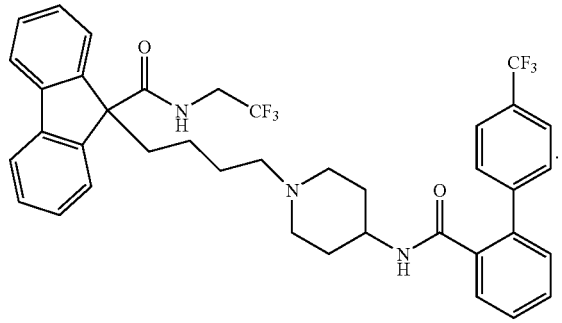

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., J. Med. Chem., Vol. 31, No. 10, pp. 1869-1871 (1988), including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, Vol. 2, pp. 1-40 (1996).

In addition, other squalene synthetase inhibitors suitable for use herein include the terpenoid pyrophosphates disclosed by P. Ortiz de Montellano et al., J. Med. Chem., 1977, 20, 243-249, the farnesyl diphosphate analog A and presqualene pyrophosphate (PSQ-PP) analogs as disclosed by Corey and Volante, J. Am. Chem. Soc., 98, 1291-1293 (1976), phosphinylphosphonates reported by McClard, R. W. et al., J. Am. Chem. Soc., 1987, 109, 5544 (1987), and cyclopropanes reported by Capson, T. L., PhD dissertation, Dept. Med. Chem. U. of Utah, Abstract, Table of Contents, pp. 16, 17, 40-43, 48-51, Summary (June, 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future, 24, 9-15 (1999), (Avasimibe); "The ACAT inhibitor, C1-1011 is effective in the prevention and regression of aortic fatty streak area in hamsters", Nicolosi et al., Atherosclerosis (Shannon, Irel). 137 (1), 77-85 (1998), "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. 6(1), 47-50 (1996); "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways 173-98 (1995), Publisher: CRC, Boca Raton, Fla.; "ACAT inhibitors: potential anti-atherosclerotic agents", Sliskovic et al, Curr. Med. Chem. 1(3), 204-25 1994); "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, *Chemtracts: Org. Chem.* 8(6), 359-62 (1995), or TS-962 (acetamide, N-[2,6-bis(1-methylethyl)phenyl]-2-(tetradecylthio)-) (Taisho Pharmaceutical Co. Ltd).

The hypolipidemic agent may be an upregulator of LD2 receptor activity such as MD-700 (1(3H)-isobenzofuranone, 3-(13-hydroxy-10-oxotetradecyl)-5,7-dimethoxy) (Taisho Pharmaceutical Co. Ltd) and LY295427 (cholestan-3-ol, 4-(2-propenyl)-, (3a, 4a, 5a)-) (Eli Lilly).

The hypolipidemic agent may be a cholesterol absorption inhibitor preferably Schering-Plough's ezetimibe (SCH58235) and SCH48461 as well as those disclosed in *Atherosclerosis* 115, 45-63 (1995) and *J. Med. Chem.* 41, 973 (1998).

The hypolipidemic agent may be an ileal $Na^+$/bile acid cotransporter inhibitor such as disclosed in *Drugs of the Future*, 24, 425-430 (1999).

The lipid-modulating agent may be a cholesteryl ester transfer protein (CETP) inhibitor such as Pfizer's CP 529,414 (torcetrapib) (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physicians' Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physicians' Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", *Brit. J. Pharmacology* 120, 1199-1206 (1997), and Cornicelli et al, "15-Lipoxygenase and its Inhibition: A Novel Therapeutic Target for Vascular Disease", *Current Pharmaceutical Design*, 5, 11-20 (1999).

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1, 2, 3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904, 769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Wellcome's GL-262570 (farglitazar), englitazone (CP-68722, Pfizer) or darglitazone (CP-86325, Pfizer, isaglitazone (MIT/J&J), JTT-501 (reglitazar) (JPNT/P&U), L-895645 (Merck), R-119702 (rivoglitazone) (Sankyo/WL), N,N-2344 (balaglitazone) (Dr. Reddy/NN), or YM-440 ((Z)-1,4-bis-4-[(3,5-dioxo-1,2,4-oxadiazolidin-2-yl-methyl)]-phenoxybut-2-ene) (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1 (1-36) amide, GLP-1 (7-36) amide, GLP-1 (7-37) (as disclosed in U.S. Pat. No. 5,614,492 to Habener, the disclosure of which is incorporated herein by reference), as well as AC2993 (exenatide) (Amylin) and LY-315902 (8-37-glucagon-like peptide I (human), N-[3-(1H-imidazol-4-yl)-1-oxopropyl]-26-L-arginine-34-[N6-(1-oxooctyl)-L-lysine]-) (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physicians' Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physicians' Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-HO39242 (tesaglitazar) (Astra/Zeneca), GW-409544 (Glaxo-Wellcome), KRP297 (benzamide, 5-[(2,4-dioxo-5-thiazolidinyl)methyl]-2-methoxy-N-[[4-(trifluoromethyl)phenyl]methyl]—(Kyorin Merck) as well as those disclosed by Murakami et al, "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", *Diabetes* 47, 1841-1847 (1998).

The antidiabetic agent may be an SGLT2 inhibitor such as disclosed in U.S. application Ser. No. 09/679,027, filed Oct. 4, 2000, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000, employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), saxagliptin (preferred), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, *Biochemistry,* 38(36), 11597-11603, (1999), TSL-225 (tryptophyl-1,2,3,4-tetrahydro-isoquinoline-3-carboxylic acid (disclosed by Yamada et al, *Bioorg. & Med. Chem. Lett.* 8 1537-1540 (1998), 2-cyanopyrrolidides and 4-cyanopyrrolidides as disclosed by Ashworth et al, *Bioorg. & Med. Chem. Lett.*, Vol. 6, No. 22, pp 1163-1166 and 2745-2748 (1996) employing dosages as set out in the above references.

The meglitinide which may optionally be employed in combination with the compound of formula I of the invention may be repaglinide, nateglinide (Novartis) or KAD1229 (mitiglinide) (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (rafabegron) (Takeda/Dainippon), L750355 (benezenesulfonamide, N-[4-[2-[[(2S)-3-[(6-amino-3-pyridinyl)oxy]-2-hydroxypropyl]amino]ethyl]phenyl]-4-(1-methylethyl)-) (Merck), or CP331684 (4-[2-[[2-(6-aminopyridin-3-yl)-2(R)-hydroxyethyl]amino]ethoxy]phenyl]acetic acid) (Pfizer) or other known beta 3 agonists as disclosed in U.S. Pat. Nos. 5,541,204, 5,770,615, 5,491,134, 5,776,983 and 5,488,064, with AJ9677, L750,355 (benzenesulfonamide, N-[4-[2-[[(2S)-3-[(6-amino-3-pyridinyl)oxy]-2-hydroxypropyl]amino]ethyl]phenyl]-4-(1-methylethyl)-) and CP331684 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), WO00/039077 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in *Clin. Exp. Pharmacol. Physiol.* 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and *Jap. J. Pharmacol.* 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and *Curr. Ther. Res.* 40:74 (1986); Ru 44570 (Hoechst) disclosed in *Arzneimittelforschung* 34:1254 (1985), cilazapril (Hoffman-LaRoche) disclosed in *J. Cardiovasc. Pharmacol.* 9:39 (1987); R 31-2201 (Hoffman-LaRoche) disclosed in *FEBS Lett.* 165:201 (1984); lisinopril (Merck), indalapril (delapril) disclosed in U.S. Pat. No. 4,385,051; indolapril (Schering) disclosed in *J. Cardiovasc. Pharmacol.* 5:643, 655 (1983), spirapril (Schering) disclosed in *Acta. Pharmacol. Toxicol.* 59 (Supp. 5):173 (1986); perindopril (Servier) disclosed in *Eur. J. Clin. Pharmacol.* 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1, 2,3,4-tetrahydro-6,7-dimethoxy-3-isoquinolinecarboxylic acid HCl) disclosed in *Pharmacologist* 26:243, 266 (1984), WY-44221 (Wyeth) disclosed in *J. Med. Chem.* 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366, 973, 5,225,401, 4,722,810, 5,223,516, 4,749,688, U.S. Pat. No. 5,552,397, U.S. Pat. No. 5,504,080, U.S. Pat. No. 5,612, 359, U.S. Pat. No. 5,525,723, European Patent Application 0599444, 0481522, 0599444, 0595610, European Patent Application 0534363A2, 534396 and 534492, and European Patent Application 0629627A2.

Preferred are those NEP/ACE inhibitors and dosages thereof which are designated as preferred in the above patents/applications which U.S. patents are incorporated herein by reference; most preferred are omapatrilat ([S—(R*,R*)]-hexahydro-6-[(2-mercapto-1-oxo-3-phenylpropyl)amino]-2, 2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physicians' Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®).

Dosages employed for the above drugs will be as set out in the Physicians' Desk Reference.

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$- and $\gamma$-cyclodextrin, or chemically modified derivatives such as hydroxyalkylcyclodextrins, including 2- and 3-hydroxypropyl-$\beta$-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 0.5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of formula I of the invention are glucocorticoid receptor modulators as shown either by their ability to bind glucocorticoid receptors in GR binding assays, or by their ability to inhibit AP-1 activity as indicated in cellular transrespressional assays, and cause none to minimal transactivation as indicated in cellular transscriptional assays.

Compounds of the invention, including the compounds described in the examples hereof, have been tested in at least one of the assay(s) described below and have glucocorticoid receptor (GR)/Dexamethasone (Dex) inhibition activity (>25% at 10 µM) and/or AP-1 inhibition activity ($EC_{50}$ less than 15 µM).

Identical and/or similar assays are described in U.S. application Ser. No. 10/621,807, filed Jul. 17, 2003 which is incorporated in its entirety herein by reference.

GR Binding Assays

Glucocorticoid Receptor Binding Assay (I)[a]

In order to assess the affinity of test compounds for the human glucocorticoid receptor, a commercially available kit was used (Glucocorticoid Receptor Competitor Assay Kit, Invitrogen Part #2893). Briefly, purified human recombinant full-length glucocorticoid receptor (2 nM) was mixed with fluorescently labeled glucocorticoid (1 nM Fluormone GS Red) in the presence or absence of test compound. After two hour incubation at room temperature in the dark, the fluorescence polarization (FP) of the samples was measured. The FP of a mixture of receptor, fluorescent probe (i.e. Fluormone GS Red) and 5 µM dexamethasone represented background fluorescence or 100% inhibition, whereas, the FP of the mixture without dexamethasone (but in the presence of vehicle) was taken to be 100% binding. The percentage inhibition of test compounds were then compared to the sample with 5 µM dexamethasone and expressed as % relative binding activity with dexamethasone being 100% and no inhibition is 0%. Test compounds were analyzed in the concentration range from 8.5E-05 µM to 5 µM.

Glucocorticoid Receptor Binding Assay (II)[b]

In order to measure the binding of compounds on the glucocorticoid receptor a commercially available kit was used (Glucocorticoid receptor competitor assay kit, PanVera Co., Madison, Wis., P2816). Briefly, a cell lysate containing recombinantly expressed human full-length glucocorticoid receptor was mixed with a fluorescently labeled glucocorticoid (1 nM Fluormone GS1) in the presence or absence of test compound. After one hour at room temperature, the fluorescence polarization (FP) of the samples were measured. The FP of a mixture of receptor, fluorescent probe (i.e. Fluormone GS1) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition is 0%. Test molecules were analyzed in the concentration range from 2.4 nM to 40 microMolar.

Site I binding assays for any NHR (Nuclear Hormone Receptor) are conducted similarly to the above. An appropriate cell lysate or purified NHR is used as the source of the NHR. The fluorescent probe and unlabeled competitor are appropriate for the specific NHR, i.e. are ligands for the specific NHR.

Cellular Transrepressional Assay

To measure the ability of test molecules to inhibit AP-1 induced transcriptional activity we utilized an A549 cell which was stably transfected with a plasmid containing 7×AP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 µM. EC50s were determined by using standard curve fitting methods such as Excel fit (Microsoft Co.). An EC50 is the test molecule concentration at which there is a 50% repression of the maximal inhibition of transcription, i.e. a 50% reduction of AP-1 activity.

Other reporters and cell lines also may be used in a cellular transrepressional assay. A similar assay is performed in which NF-κB activity is measured. A plasmid containing NF-κB DNA binding sites is used, such as pNF-kB-Luc, (Stratagene, LaJolla Calif.), and PMA or another stimulus, such as TNF-α or lipopolysaccharide, is used to activate the NF-κB pathway. NF-κB assays similar to that described in Yamamoto K., et al., *J. Biol. Chem.*, December 29; 270(52):31315-20 (1995) may be used.

The cellular transrepressional assays described above may be used to measure transrepression by any NHR. One of skill in the art will understand that assays may require the addition of components, such as a stimulus (eg. PMA, lipopolysaccharide, TNF-α, etc) which will induce transcription mediated by AP-1 or NF-κB.

Additionally, AR mediated transrepression may be measured by the assay described in Palvimo J J, et al. *J. Biol. Chem.*, September 27; 271(39):24151-6 (1996), and PR mediated transrepression may be measured by the assay described in Kalkhoven E., et al. *J. Biol. Chem.*, March 15; 271(11):6217-24 (1996).

Examples of compounds of the present invention prepared by methods described in the general schemes are given in the preparations and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diaststereoselectivity of transformations, providing enantio-enriched products upon cleavage of the chiral auxiliary.

ABBREVIATIONS

The following abbreviations are employed in the following Preparations and Examples:
Ph=phenyl
Bn=benzyl
t-Bu=tertiary butyl
Me=methyl
Et=ethyl
ACN=acetonitrile
TMS=trimethylsilyl
$TMSN_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
$Et_2O$=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane
HMPA=hexamethyl phosphoric triamide
HOAc or AcOH=acetic acid
TFA=trifluoroacetic acid
TFAA=trifluoroacetic anhydride
i-$Pr_2$NEt=diisopropylethylamine
$Et_3$N=triethylamine
NMM=N-methyl morpholine
DMAP=4-dimethylaminopyridine
$NaBH_4$=sodium borohydride
$NaBH(OAc)_3$=sodium triacetoxyborohydride
DIBALH=diisobutyl aluminum hydride
LAH or $LiAlH_4$=lithium aluminum hydride
n-BuLi=n-butyllithium
LDA=lithium diisopropylamide
Pd/C=palladium on carbon
$PtO_2$=platinum oxide
KOH=potassium hydroxide
NaOH=sodium hydroxide
LiOH=lithium hydroxide
$K_2CO_3$=potassium carbonate
$NaHCO_3$=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.$H_2O$=1-hydroxybenzotriazole hydrate
HOAT=1-Hydroxy-7-azabenzotriazole
BOP reagent=benzotriazol-1-yloxy-tris (dimethylamino) phosphonium hexafluorophosphate
$NaN(TMS)_2$=sodium hexamethyldisilazide or sodium bis(trimethylsilyl)amide
$Ph_3P$=triphenylphosphine
$Pd(OAc)_2$=Palladium acetate
$(Ph_3P)_4Pd°$=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
$N_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
rt or RT=room temperature
sat or sat'd=saturated
aq.=aqueous
TLC=thin layer chromatography
HPLC=high performance liquid chromatography
Reverse phase HPLC=reverse phase high performance liquid chromatography, using a YMC ODS S5 column and a binary solvent A/solvent B eluents
Solvent A=10% MeOH-90% $H_2O$-0.1% TFA
Solvent B=90% MeOH-10% $H_2O$-0.1% TFA; or
Solvent A=$H_2O$ containing 0.1% TFA
Solvent B=ACN containing 0.1% TFA
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet mp=melting point

EXAMPLES

The following Examples illustrate embodiments of the inventive compounds and starting materials, and are not intended to limit the scope of the claims.

Preparations

The preparations set out below are for the synthesis of reagents that were not obtained from commercial sources and were employed for the preparation of compounds of formula I of the invention. All chiral compounds in the tables and schemes are racemic unless specified otherwise.

Reverse-phase preparative high performance liquid chromatography ("HPLC") was performed with Shimadzu 8A liquid chromatographs using YMC S5 ODS columns (20× 100, 20×250 or 30×250 millimeter ("mm")). Gradient elution was performed with methanol ("MeOH")/water mixtures in the presence of 0.1% trifluoroacetic acid ("TFA").

Analytical HPLC Methods

Analytical HPLC was performed on Shimadzu SCL10A liquid chromatographs using the following methods: Unless otherwise designated, Method D conditions were used to generated data for compounds appearing throughout the Preparations and Examples.

Method A: Column: YMC Combiscreen ODS-A, 4.6×50 mm, Mobile phase: 10-90% aq CH3OH/0.2% $H_3PO_4$, 4.0 min. gradient with 1.0 min. hold, Flow rate: 4 ml/min, 220 nm detection wavelength.

Method B: Column: XETRRA C-18 4.6×50 mm, Mobile Phase: 10-90% aq CH3OH/0.2% $H_3PO_4$, 4.0 min. gradient with 1 min. hold, Flow rate: 4.0 mL/min. 220 nm detection wavelength.

Method C: Column: Phenomenex Synergi C-18 4.6×50 mm, Mobile phase: 10-90% aq CH3OH/0.2% H3PO4, 4.0 min. gradient with 1 min. hold, Flow rate: 4.0 mL/min, 220 nm detection wavelength.

Method D: Column: Shimadzu VP-ODS; C-18 Ballistic 4.6×50 mm, Mobile phase: 10-90% aq CH3OH/0.2% H3PO4, 4.0 min. gradient with 1 min. hold, Flow rate: 4.0 mL/min, 220 nm detection wavelength.

Preparations

The preparations set out below are for the synthesis of reagents that were not obtained from commercial sources and were employed for the preparation of compounds of formula I of the invention. All chemical structures in the tables and schemes are racemic unless specified otherwise.

PREPARATION 1

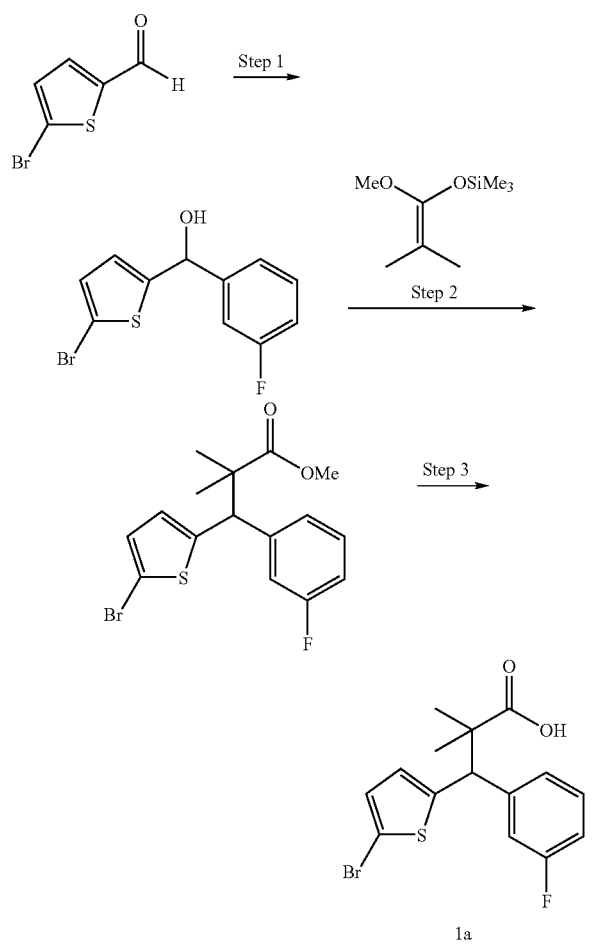

Step 1

To a solution of 3-fluorophenyl)magnesium bromide (1M in THF, 6.8 ml. 6.8 mmol) at 0° C. was added a solution of 5-bromo-thiophene-2-carbaldehyde (650 mg, 3.4 mmol) in THF (10 ml) dropwise. After being stirred at 0° C. for 10 minutes and room temperature for 3 hours, the reaction mixture was poured onto an iced aqueous $NH_4Cl$. The solution was extracted with ethyl acetate. The organic layer was washed with brine, dried over $MgSO_4$ and concentrated to give (5-bromo-thiophen-2-yl)-(3-fluoro-phenyl)-methanol as a viscous liquid (1.19 g, quantitative yield). LC/MS (m/z) 271, 273 [(M–OH)$^+$]; HPLC (Column: Method D—unless otherwise designated, Method D HPLC conditions have been used for analysis of exemplified compounds) Rt: 3.176 min.

Step 2

To a solution of (5-bromo-thiophen-2-yl)-(3-fluoro-phenyl)-methanol (3.40 mmol) and (1-methoxy-2-methyl-propenyloxy)-trimethyl-silane (3.45 ml, 17 mmol) in dichloromethane (10 ml) at 0° C. was added a solution of titanium tetrachloride in dichloromethane (1M solution, 7.4 ml, 7.4 mmol) slowly. After being stirred at 0° C. for 10 minutes and room temperature for 3 hours, the reaction mixture was poured onto an iced aqueous $K_2CO_3$. The solution was extracted with dichloromethane. The organic layer was washed, dried ($MgSO_4$) and concentrated to give 3-(5-bromo-thiophen-2-yl)-3-(3-fluoro-phenyl)-2,2-dimethyl-propionic acid methyl ester as a viscous yellow oil (1.104 g, 87.5% yield). LC/MS (m/z) 393.13 [(M+23)$^+$]; HPLC Rt: 3.883 min.

Step 3

To a solution of 3-(5-bromo-thiophen-2-yl)-3-(3-fluoro-phenyl)-2,2-dimethyl-propionic acid methyl ester (419 mg, 1.128 mmol) in MeOH (4 ml) and DMSO (2 ml) was added a 40% aqueous solution of potassium hydroxide (4 ml). The reaction mixture was heated at 75° C. for 6 hours. After removal of methanol, the solution was adjusted to pH 2 and was extracted with ethyl ether. The ether layer was washed, dried and evaporated to give 3-(5-bromo-thiophen-2-yl)-3-(3-fluoro-phenyl)-2,2-dimethyl-propionic acid (1a) as a white glass (346.2 mg, 86% yield). $^1$H NMR (400 MHz, CDCl$_3$): δ 1.06 (s, 3H), 1.15 (s, 3H), 3.21 (s, 1H), 6.75 (d, 1H, J=3.8 Hz), 6.82 (d, 1H, J=3.8 Hz), 6.87 (td, 1H, J=8.1, 2.6 Hz), 7.02 (m, 1H), 7.10 (br d, J=8.1 Hz), 7.20 (m, 1H). HPLC Rt: 3.695 min.

According to the procedure described above, the acid of formula (1b) was prepared from 5-bromo-thiophene-2-carbaldehyde and phenylmagnesium bromide.

| Preparation | Structure |
|---|---|
| 1b | ![structure] |

PREPARATION 2

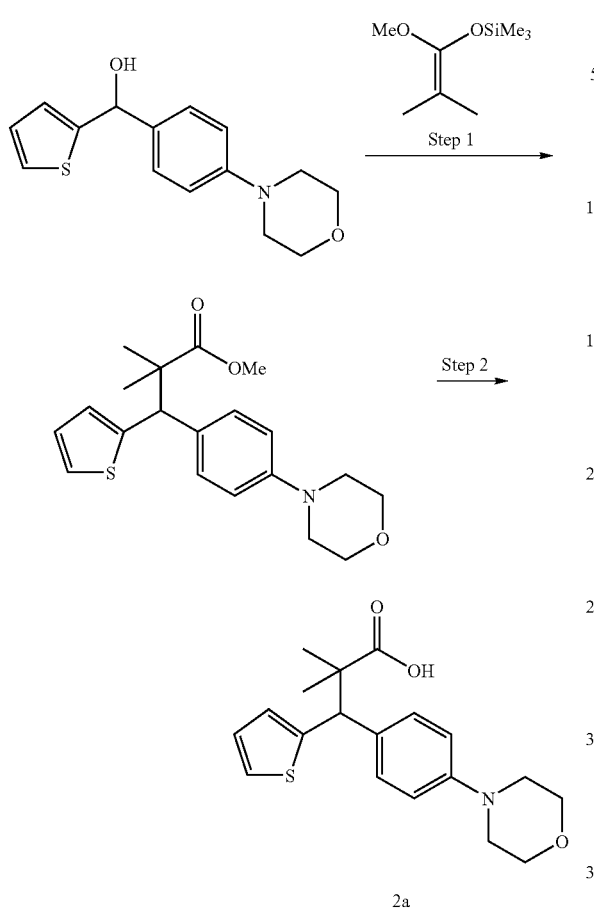

2a

| Preparation | Structure |
|---|---|
| 2b | 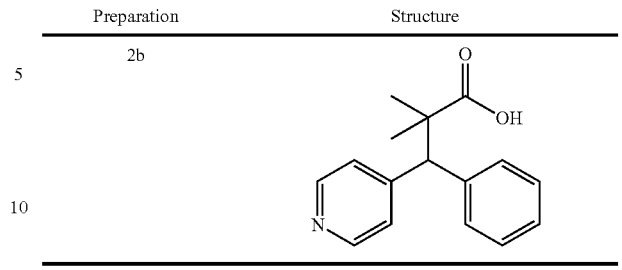 |

PREPARATION 3

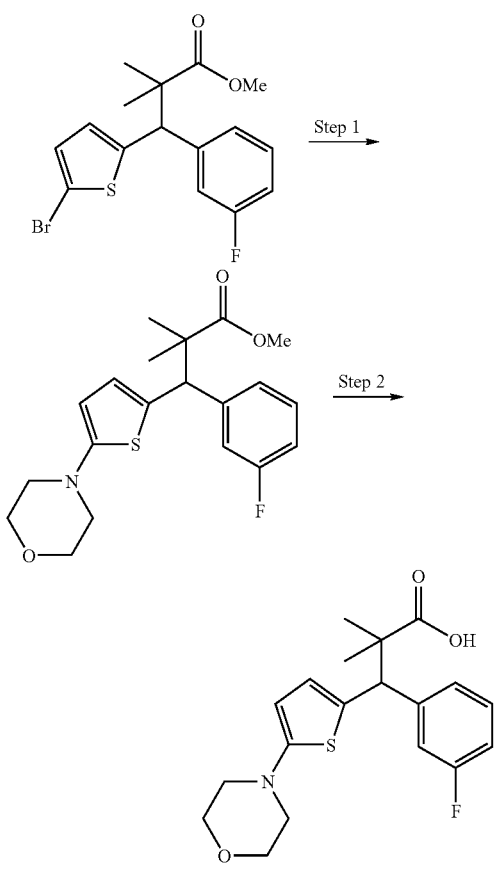

3

Step 1

In a similar manner to Preparation 1, Step 2, the reaction of (4-morpholinophenyl)-(thiophen-2-yl)methanol (675 mg, 2.45 mmol), prepared from 4-morpholinobenzaldehyde and thiophen-2-ylmagnesium bromide, and (1-methoxy-2-methylprop-1-enyloxy)trimethylsilane (2.48 ml, 12.3 mmol) in the presence of titanium tetrachloride (1M in DCM, 5.40 ml. 5.40 mmol) afforded methyl 2,2-dimethyl-3-(4-morpholinophenyl)-3-(thiophen-2-yl)propanoate (725 mg, 82.5% yield).). $^1$H NMR (400 MHz, CDCl$_3$): δ 1.15 (s, 3H), 1.20 (s, 3H), 3.06 (m, 4H), 3.51 (s, 3H), 3.78 (m, 4H), 4.59 (s, 1H), 6.76 (d, 1H, J=8.5 Hz), 6.83 (m, 1H), 6.87 (m, 1H), 7.06 (m, 1H), 7.20 (d, 1H, J=8.5 Hz). HPLC Rt: 3.181 min.

Step 2

In a similar manner to Preparation 1, Step 3, the basic hydrolysis of methyl 2,2-dimethyl-3-(4-morpholinophenyl)-3-(thiophen-2-yl)propanoate (530 mg, 1.47 mmol) afforded 2,2-dimethyl-3-(4-morpholinophenyl)-3-(thiophen-2-yl) propanoic acid (2a) (469 mg, 92.5% yield). $^1$H NMR (400 MHz, CDCl$_3$): δ 1.17 (s, 3H), 1.24 (s, 3H), 3.06 (m, 4H), 3.77 (m, 4H), 4.62 (s, 1H), 6.77 (d, 1H, J=8.7 Hz), 6.91 (m, 1H), 6.87 (d, 1H, J=3.16 Hz), 7.07 (m, 1H), 7.22 (d, 1H, J=8.7 Hz). /MS (m/z) 346.35 [(M+H)$^+$]; HPLC Rt: 2.863 min.

According to the procedure described above, the acid of formula (2b) was prepared from phenyl-pyridin-4-yl-methanone.

Step 1

A mixture of methyl 3-(5-bromothiophen-2-yl)-3-(3-fluorophenyl)-2,2-dimethyl-propanoate, product of Preparation 1, Step 2, (367 mg, 0.988 mmol), morpholine (0.572 mL), palladium acetate (44 mg, 0.20 mmol), 2-(di-tert-butylphosphino)-biphenyl (118 mg, 0.40 mmol), and sodium tert-butoxide (228 mg, 2.37 mmol) in toluene (5 ml) was heated at 80° C. for 2 h. The reaction mixture was cooled to room temperature, the solid was removed by filtration, and the filtrate was concentrated in vacuo. The crude product was purified by silica gel flash chromatography using 20% ethyl acetate in hexanes to give methyl 3-(3-fluorophenyl)-2,2-dimethyl-3-(5-morpholinothiophen-2-yl)propanoate as an oil (120 mg, 32.2%). LC/MS (m/z) 378.33 [(M+H)$^+$]; HPLC Rt: 3.548 min.

Step 2

In a similar manner to Preparation 1, Step 3, the basic hydrolysis of methyl 3-(3-fluorophenyl)-2,2-dimethyl-3-(5-morpholinothiophen-2-yl)propanoate (120 mg, 0.318 mmol) afforded 3-(3-fluorophenyl)-2,2-dimethyl-3-(5-morpholinothiophen-2-yl) propanoic acid (4) (110 mg, 95.3% yield).). LC/MS (m/z) 364.31 [(M+H)+]; HPLC Rt: 3.323 min.

PREPARATION 4

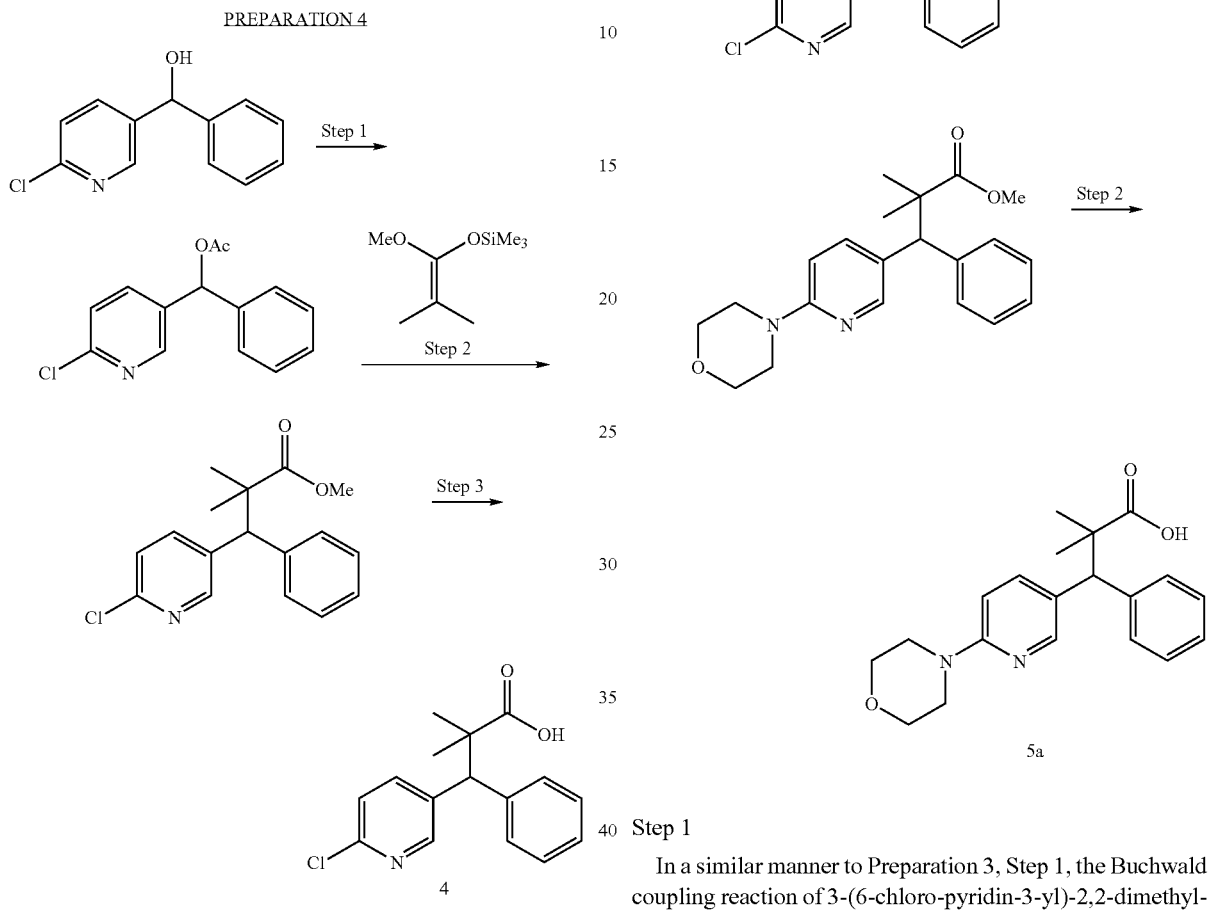

Step 1

To a solution of (6-chloro-pyridin-3-yl)-phenyl-methanol (2 g, 9.10 mmol) in dichloromethane (25 ml) were added acetic anhydride (3.5 ml, 36.4 mmol) and DMAP (1.10 g, 9.10 mmol). The reaction mixture was stirred for 16 hours, and then was washed with water, dried and concentrated to give acetic acid (6-chloro-pyridin-3-yl)-phenyl-methyl ester as a viscous liquid. LC/MS (m/z) 262.12 [(M+H)+]; HPLC Rt: 3.011 min.

Step 2

In a similar manner to Preparation 1, Step 2, the reaction of the product of Step 1 (1 g, 3.82 mmol) and (1-methoxy-2-methylprop-1-enyloxy)trimethylsilane (5.5 ml, 26.7 mmol) in the presence of titanium tetrachloride (1M in DCM, 8.40 ml. 8.40 mmol) afforded 3-(6-chloro-pyridin-3-yl)-2,2-dimethyl-3-phenyl-propionic acid methyl ester as a light yellow oil (1.1 g, 81% yield). LC/MS (m/z) 304.16 [(M+H)+]; HPLC Rt: 3.401 min

Step 3

In a similar manner to Preparation 1, Step 3, the basic hydrolysis of the product of Step 2 (1 g, 3.29 mmol) afforded 3-(6-chloro-pyridin-3-yl)-2,2-dimethyl-3-phenyl-propionic acid (4) (947 mg, 99% yield). LC/MS (m/z) 290.16 [(M+H)+]; HPLC Rt: 3.018 min.

Step 1

In a similar manner to Preparation 3, Step 1, the Buchwald coupling reaction of 3-(6-chloro-pyridin-3-yl)-2,2-dimethyl-3-phenyl-propionic acid methyl ester (product of Preparation 4, Step 2, 255 mg, 0.85 mmol) with morpholine (3 ml) afforded 2,2-dimethyl-3-(6-morpholin-4-yl-pyridin-3-yl)-3-phenyl-propionic acid methyl ester as an off-white amorphous solid. (208 mg, 69% yield). LC/MS (m/z) 355.17 [(M+H)+]; HPLC Rt: 2.13 min.

Step 2

In a similar manner to Preparation 1, Step 3, the basic hydrolysis of the product of Step 1 (80 mg, 0.226 mmol) afforded 2,2-dimethyl-3-(6-morpholin-4-yl-pyridin-3-yl)-3-phenyl-propionic acid (5a) (76 mg, 99% yield).). LC/MS (m/z) 341.17 [(M+H)+]; HPLC Rt: 1.898 min.

Alternatively, the acid (5a) can be prepared by heating 3-(6-chloro-pyridin-3-yl)-2,2-dimethyl-3-phenyl-propionic acid (acid of Preparation 4a, 110 mg) in morpholine (1 ml) at 200° C. for 3 hours (71% yield).

According to the procedures described in Steps 1 and 2, the acids of formula (5b) to (5e) were prepared from the reaction of 3-(6-chloro-pyridin-3-yl)-2,2-dimethyl-3-phenyl-propionic acid methyl ester and corresponding secondary amines, followed by basic hydrolysis.

| Preparation | Structure |
|---|---|
| 5b | (structure: 2-methyl-3-phenyl-3-(6-piperidin-1-yl-pyridin-3-yl)propanoic acid) |
| 5c | (structure: 2-methyl-3-phenyl-3-(6-pyrrolidin-1-yl-pyridin-3-yl)propanoic acid) |
| 5d | (structure: 2-methyl-3-phenyl-3-{6-[(4-methylbenzyl)amino]pyridin-3-yl}propanoic acid) |
| 5e | (structure: 3-{6-[4-hydroxypiperidin-1-yl]pyridin-3-yl}-2-methyl-3-phenylpropanoic acid) |

Preparation 6

The acid of preparation (1b) was resolved into its corresponding enantiomers, acid of formula (6a) and (6b) using chiral supercritical fluid chromatography (SFC) with the following conditions.

Chiral-SFS Prep. Conditions: Chiralpak AD (0.46×25 cm, 10 μm); BPR Pressure 100 bars; Temperature: 35° C.; Mobil Phase: CO$_2$/MeOH (73/27); Flow rate: 70 mL/min; UV Detection: 220 nm.

Analytical HPLC (Column: Chiralpak®-AD, 4.6×250 mm 10 μm, Mobile phase: CO$_2$/MeOH (85/85), Flowrate: 2 mL/min, Detection UV 220 nM) Retention times: Enantiomer A (6a): 6.66 min (ee>99.9%); Enantiomer B (6b): 12.13 min (ee>99.9%)

In general, if the absolute stereochemistry of the two enantiomers are not yet defined. Isomer A designates the first eluting enantiomer, and Isomer B the second eluting enantiomer.

| Preparation | Structure | HPLC Rt: minute | MS [m/z (M + H)] |
|---|---|---|---|
| 6a | (Enantiomer A, 5-bromothiophene derivative) | 3.895 | 337, 339 |
| 6b | (Enantiomer B, 5-bromothiophene derivative) | 3.898 | 337, 339 |

Preparation 7

In a similar manner to Preparation 6, the acid of preparation (1a) was resolved into its enantiomers, acids of formula (7a) and (7b), using chiral supercritical fluid chromatography (SFC).

Analytical HPLC (Column: Chiralpak®-AD, 4.6×250 mm 10 μm, Mobile phase: CO2/MeOH (80/20), BPR Pressure 100 bar, Flowrate: 2.4 mL/min, Detection: 220 nm) Retention times: (S)-enantiomer (7a): 2.59 min (ee>99.9%); (R)-enantiomer (7b): 4.58 min (ee>99.5%).

| Preparation | Structure | HPLC Rt: minute | MS m/z [M − 1] |
|---|---|---|---|
| 7a | 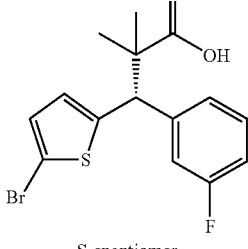<br>S-enantiomer | 3.900 | 355, 357 |
| 7b | 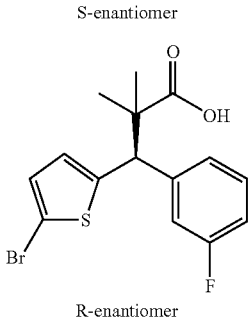<br>R-enantiomer | 3.896 | 355, 357 |

PREPARATION 8

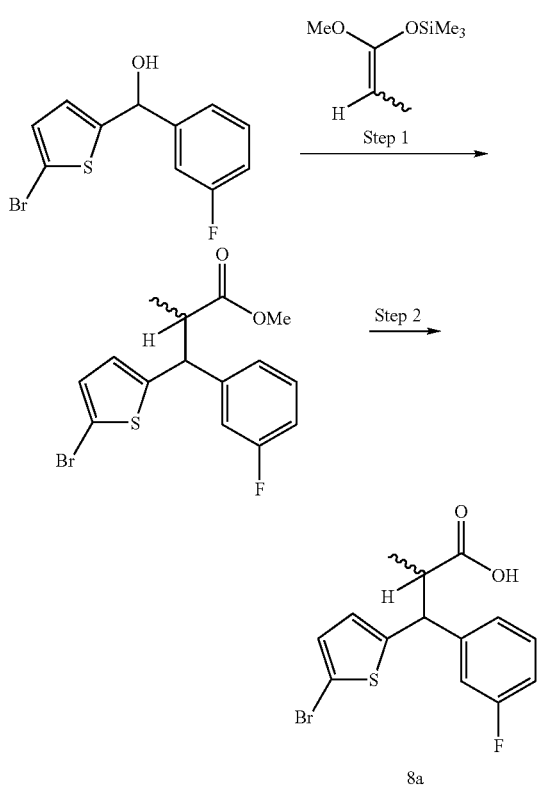

Step 1

To a solution of (5-bromo-thiophen-2-yl)-(3-fluoro-phenyl)-methanol (2 g, 6.96 mmol) and (1-methoxy-2-methyl-propenyloxy)-trimethyl-silane (2.23 g, 13.92 mmol) in dichloromethane (20 ml) at 0° C. was added a solution of titanium tetrachloride in dichloromethane (1M solution, 7.7 ml, 7.66 mmol) slowly. After being stirred at 0° C. for 10 minutes and room temperature overnight, the reaction mixture was poured into an iced aqueous solution of $K_2CO_3$. The solution was extracted with dichloromethane. The organic layer was washed, dried (MgSO$_4$) and concentrated to give the crude product. The crude product was purified by silica gel flash chromatography using 10% ethyl acetate in hexanes to give methyl 3-(5-bromothiophen-2-yl)-3-(3-fluorophenyl)-2-methyl-propanoate as a viscous yellow oil (1.74 g, 70% yield). HPLC Rt: 3.97 min.

Step 2

To a solution of the product from Step 1,3-(5-bromothiophen-2-yl)-3-(3-fluorophenyl)-2-methyl-propanoate (600 mg, 1.68 mmol) in MeOH (10 ml) and DMSO (4 ml) was added a 40% aqueous solution of potassium hydroxide (10 ml). The reaction mixture was heated at 75° C. for 1.5 hours. After removal of methanol, the solution was adjusted to pH 2 and was extracted with ethyl ether. The ether layer was washed, dried and evaporated to give the crude product. The crude product was purified by silica gel flash chromatography using 20-30% ethyl acetate in hexanes to give 3-(5-bromothiophen-2-yl)-3-(3-fluorophenyl)-2-methylpropanoic acid (8a) as a 1:1 diastereomeric mixture, pale yellow solid (570 mg, 99% yield). $^1$H NMR (400 MHz, MeOD) δ ppm 7.24-7.39 (1H, m) 7.10-7.19 (1H, m) 7.03-7.10 (1H, m) 6.86-7.01 (2H, m) 6.79-6.85 (1H, m) 4.29 (0.5H, d, J=2.77 Hz), 4.29 (0.5H, d, J=2.77 Hz), 4.31 (0.5H, d, J=2.77 Hz), 3.12-3.24 (1H, m) 1.20-1.22 (3H, 2 singlets), 1.03-1.05 (3H, 2 singlets). MS ESI (m/z) 341, 343 [M–1]; HPLC Rt: 3.765 min.

According to the procedure described above, the acid of formula (8b) was prepared from (5-bromothiophen-2-yl)(phenyl)methanol.

| Preparation | Structure |
|---|---|
| 8b | structure |

Preparation 9

The acid of Preparation (8a) was resolved into its corresponding four stereoisomers of formula (9a), (9b), (9c), and (9d) using chiral supercritical fluid chromatography (SFC) with the following conditions. The separations were carried out in two steps.

Step 1: Isolation of the Third Eluting Isomer and the Fourth Eluting Isomer

Chiral-SFS Prep. Conditions: Column: Chiralpak AD-H (0.46×25 cm, 5 μm); BPR Pressure 100 bars; Temperature: 35° C.; Mobil Phase: CO2/(IPA/MeOH=50/50)=90/10; Flow rate: 120 mL/min; UV Detection: 252 nm. Under these conditions, the first eluting isomer and the second eluting isomer are not separable, which will be isolated using second SFC conditions.

Analytical HPLC conditions: Column: Chiralpak AD-H (0.46×25 cm, 5 μm), Mobile phase: CO2/(IPA/MeOH=50/50)=90/10, Temperature: 35° C., Flowrate: 3 mL/min, Detection: UV (252 nm). Retention times: Third eluting isomer (9c), 7.41 (ee>99.9%) min; Fourth eluting isomer (9d), 7.50 min (ee>99.5%).

The first peak to elute under the preparative (SFC) conditions described above also eluted first under the aforementioned analytical chiral LC conditions. So do the corresponding second, third and fourth peaks.

Step 2: Isolation of the First Eluting Isomer and the Second Eluting Isomer

Chiral-SFS Prep. Conditions: Column: Chiralcel OJ-H (0.46×25 cm, 5 μm), Mobil Phase: CO2/MeOH=88:12, BPR pressure: 100 bars; Temperature: 35° C.; Flowrate: 70 mL/min, Detection: UV (252 nm).

Analytical HPLC conditions, Column: Chiralcel OJ-H (0.46×25 cm, 5 μm), Mobile phase: CO2/MeOH=95:5, Temperature: 35° C., Flow rate: 3 mL/min, Detection: UV (252 nm). Retention Time (min): First eluting isomer (9a), 6.79 (>99% ee); Second eluting isomer (9b), 8.21 (>99% ee).

A sample of the third-eluting isomer (9c) co-crystallized with (+)-β-methyl phenethyl amine in acetonitrile. An X-ray crystal structure determination of the crystalline material thus obtained proved (9c) to be of (2R,3S) configuration. A sample of the fourth-eluting isomer (9c) co-crystallized with (+)-β-methyl phenethylamine in acetonitrile. An X-ray crystal structure determination of the crystalline material thus obtained proved (9d) to be of (2R,3R) configuration. The configuration of (9a), the antipode of (9d), thus was assigned as (2S,3S) and the configuration of (9b), the antipode of (9c), as (2R,3S).

| Preparation | Structure | HPLC Rt: minute | MS m/z [M − 1] |
|---|---|---|---|
| 9a | Isomer 1 (2S, 3S) | 3.731 | 341 |
| 9b | Isomer 2 (2S, 3R) | 3.681 | 341 |
| 9c | Isomer 3 (2R, 3S) | 3.691 | 341 |
| 9d | Isomer 4 (2R, 3R) | 3.736 | 341 |

Preparation 10

In a similar manner to Preparation 9, the acid of preparation (8b) was resolved into its corresponding 4 stereoisomers, acids of formula (10a, 10b, 10c) and (10d) using chiral supercritical fluid chromatography (SFC) in two steps.

Analytical HPLC (Chiralcel OJ-H (0.46×25 cm, 5 μm), Mobile phase: CO2/(IPA:MeOH/1:1)=85:15, Flowrate: 2 mL/min, Detection: UV 252 nm) Retention times: Third eluting isomer (10c) 6.60 min (ee>99.9%); Fourth eluting isomer (10d): 8.62 min (ee>99.9%).

Analytical HPLC (Column: Chiralpak®-AD, Mobile phase: CO2/(IPA:CH3CN/1:1)=88:12, Flowrate: 3 mL/min, Detection: UV 249 nm) Retention times: First eluting isomer (10a) 5.79 min (ee>99.9%); Second eluting isomer (10b): 8.29 min (ee>99.9%). The absolute stereochemistry of the first and the fourth eluting isomers have been determined as (2S,3S) and (2R,3R) respectively. The absolute stereochemistry of the second and the third eluting isomers have not yet been determined.

| Preparation | Structure | HPLC Rt: minute | MS m/z [M − 1] |
|---|---|---|---|
| 10a | Isomer 1 (2S, 3S) | 3.698 | 323, 325 |
| 10b | Isomer 2 (chiral) | 3.651 | 323, 325 |
| 10c | Isomer 3 (chiral) | 3.658 | 323, 325 |
| 10d | Isomer 4 (2R, 3R) | 3.696 | 323, 325 |

EXAMPLES

Example 1

3-(5-Bromo-2-thienyl)-3-(3-fluorophenyl)-2,2-dimethyl-N-1,3,4-thiadiazol-2-ylpropanamide

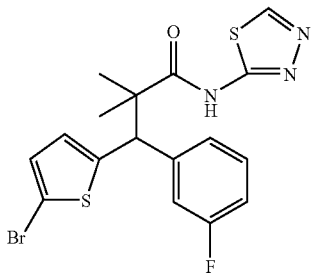

To a solution of the acid of Preparation 1a (150 mg, 0.42 mmol) in CH3CN (5 mL) were added 1-[3-(dimethylamino)propyl]-3-ethylcarbodiimide hydrochloride (EDC) (120 mg, 0.63 mmol) and 1-hydroxy-7-benzotriazole (HOBt) (84 mg, 0.63 mmol). After stirring for 5 minutes, to the solution were added 4-(4-methyl-naphthalen-1-yl)-thiazol-2-ylamine (126 mg, 1.26 mmol) and diisopropylethyl amine (0.22 ml, 1.26 mmol). The reaction was heated at 75° C. for 12 hours. The reaction mixture was filtered, concentrated and purified by silica gel flash chromatography using 25% ethyl acetate in hexanes to give the title compound of Example 1 as a white solid (129 mg, 69.6% yield).). $^1$H NMR (400 MHz, CDCl$_3$): δ 1.24 (s, 3H), 1.31 (s, 3H), 4.79 (s, 1H), 6.75 (d, 1H, J=4.1 Hz), 6.81 (d, 1H, J=4.1 Hz), 6.89 (m, 1H), 7.11 (m, 1H), 7.22 (m, 1H), 8.91 (s, 1H). LC/MS (m/z) 440.16, 442.16 [(M+H)$^+$]; HPLC Rt: 3.58 min.

Examples 2 to 19

In a similar manner to Example 1, Examples 2 to 19 were prepared via the amidation reactions of acids of Preparations (1) to (3) and (5) with the appropriate amines. (Compounds are racemic unless noted)

| Example No. | Name | Structure | HPLC Rt: Min. | MS [m/z (M + H)] |
|---|---|---|---|---|
| 2 | 3-(5-bromo-2-thienyl)-3-(3-fluorophenyl)-2,2-dimethyl-N-1,3-thiazol-2-ylpropanamide | 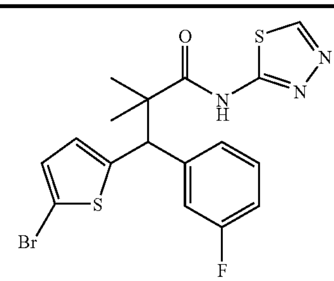 | 4.400 | 441.1, 439.1 |
| 3 | -(5-bromo-2-thienyl)-2,2-dimethyl-3-phenyl-N-1,3,4-thiadiazol-2-ylpropanamide | 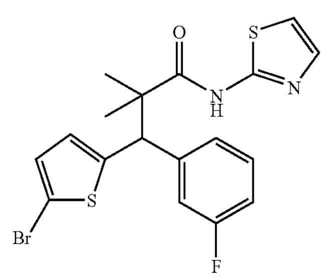 | 3.768 | 423.1 424.1 |
| 4 | 3-(5-bromo-2-thienyl)-2,2-dimethyl-3-phenyl-N-1,3-thiazol-2-ylpropanamide | 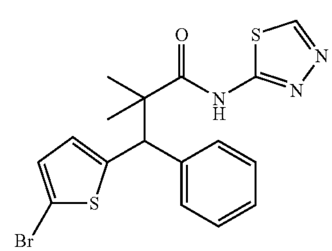 | 3.901 | 423.1 421.1 |

-continued

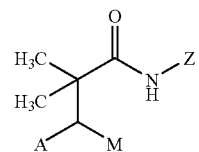

| Example No. | Name | Structure | HPLC Rt: Min. | MS [m/z (M + H)] |
|---|---|---|---|---|
| 5 | 2,2-dimethyl-3-phenyl-3-(4-pyridinyl)-N-(4-(4-(4-pyridinyl)benzyl)-1,3-thiazol-2-yl)propanamide | 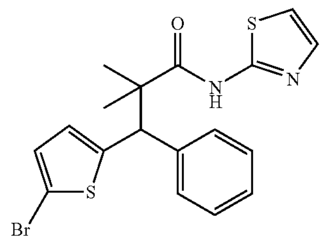 | 2.075 | 505.3 |
| 6 | 2,2-dimethyl-3-phenyl-3-(4-pyridinyl)-N-1,3,4-thiadiazol-2-ylpropanamide | 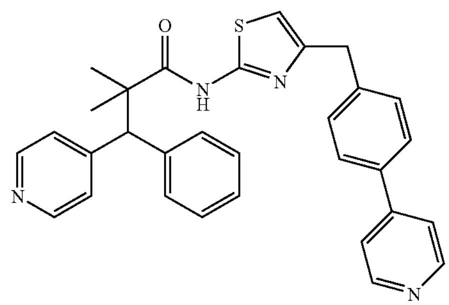 | 1.560 | 339.2 |
| 7 | 2,2-dimethyl-3-phenyl-3-(4-pyridinyl)-N-1,3-thiazol-2-ylpropanamide | 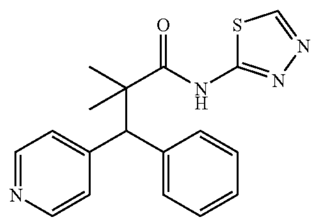 | 1.810 | 338.3 |
| 8 | 2-((2,2-dimethyl-3-phenyl-3-(4-pyridinyl)propanoyl)amino)-N,N-dimethyl-1,3-thiazole-4-carboxamide | 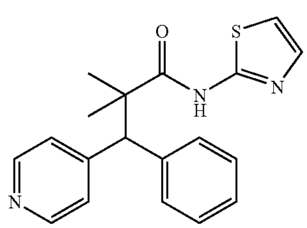 | 2.015 | 409.3 |
| 9 | 3-(3-fluorophenyl)-2,2-dimethyl-3-(5-(4-morpholinyl)-2-thienyl)-N-1,3,4-thiadiazol-2-ylpropanamide | 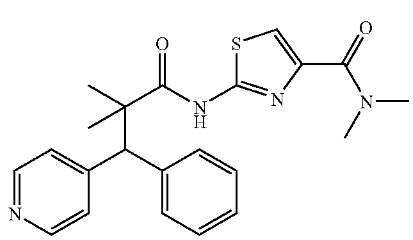 | 3.236 | 447.3 |

-continued
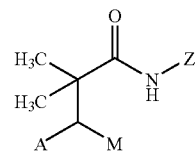
| Example No. | Name | Structure | HPLC Rt: Min. | MS [m/z (M + H)] |
|---|---|---|---|---|
| 10 | 3-(3-fluorophenyl)-2,2-dimethyl-3-(5-(4-morpholinyl)-2-thienyl)-N-1,3-thiazol-2-ylpropanamide | 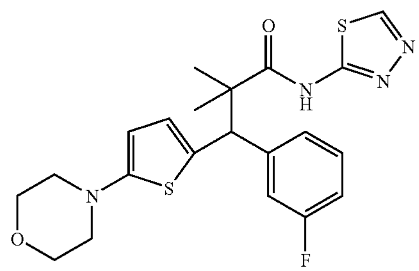 | 3.375 | 446.3 |
| 11 | 2,2-dimethyl-3-(4-(4-morpholinyl)phenyl)-N-1,3,4-thiadiazol-2-yl-3-(2-thienyl)propanamide | 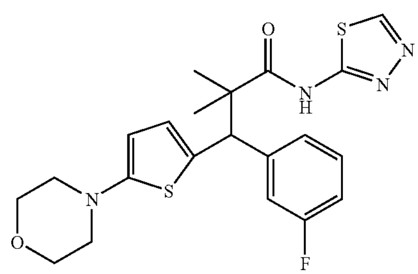 | 2.828 | 429.4 |
| 12 | 2,2-dimethyl-3-(4-(4-morpholinyl)phenyl)-N-1,3-thiazol-2-yl-3-(2-thienyl)propanamide | 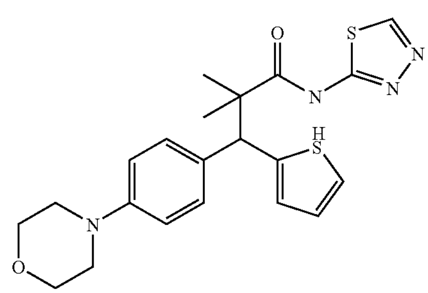 | 3.001 | 428.4 |
| 13 | 2,2-dimethyl-3-(6-(4-morpholinyl)-3-pyridinyl)-3-phenyl-N-1,3,4-thiadiazol-2-ylpropanamide | 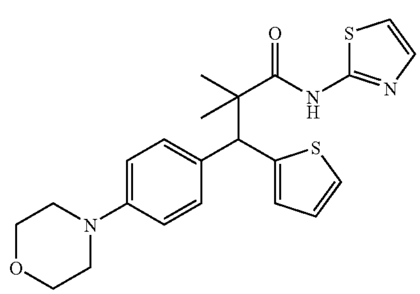 | 1.972 | 424.2 |

-continued
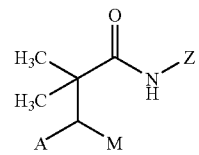
| Example No. | Name | Structure | HPLC Rt: Min. | MS [m/z (M + H)] |
|---|---|---|---|---|
| 14 | 2,2-dimethyl-3-(6-(4-morpholinyl)-3-pyridinyl)-3-phenyl-N-1,3-thiazol-2-ylpropanamide | 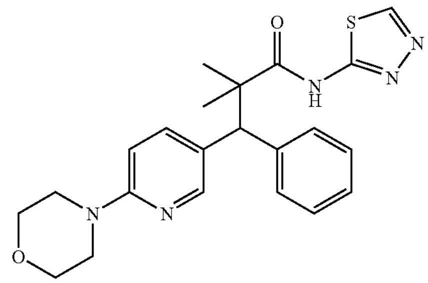 | 2.215 | 423.3 |
| 15 | 2,2-dimethyl-3-phenyl-3-(6-(1-piperidinyl)-3-pyridinyl)-N-1,3,4-thiadiazol-2-ylpropanamide | 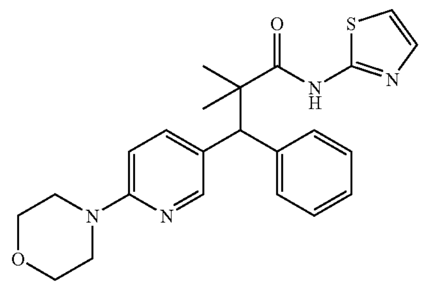 | 2.200 | 422.2 |
| 16 | 2,2-dimethyl-3-phenyl-3-(6-(1-pyrrolidinyl)-3-pyridinyl)-N-1,3,4-thiadiazol-2-ylpropanamide | 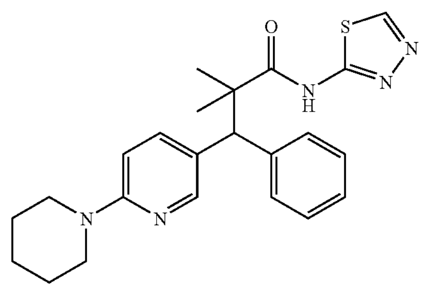 | 2.085 | 408.2 |
| 17 | 3-(6-(4-hydroxy-1-piperidinyl)-3-pyridinyl)-2,2-dimethyl-3-phenyl-N-1,3,4-thiadiazol-2-ylpropanamide | 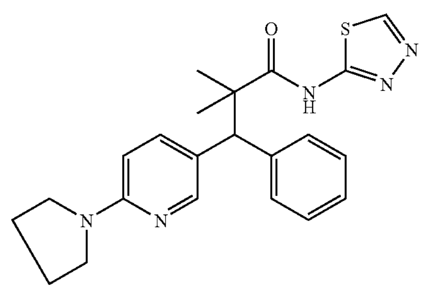 | 1.950 | 438.3 |

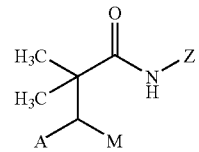

| Example No. | Name | Structure | HPLC Rt: Min. | MS [m/z (M + H)] |
|---|---|---|---|---|
| 18 | 2,2-dimethyl-3-(6-((4-methylbenzyl)amino)-3-pyridinyl)-3-phenyl-N-1,3-thiazol-2-ylpropanamide | 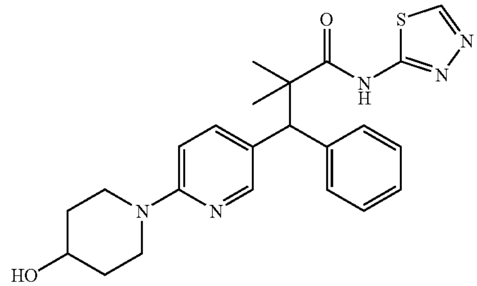 | 2.766 | 457.3 |
| 19 | 3-(5-bromo-2-thienyl)-3-(3,5-difluorophenyl)-2,2-dimethyl-N-1,3,4-thiadiazol-2-ylpropanamide | 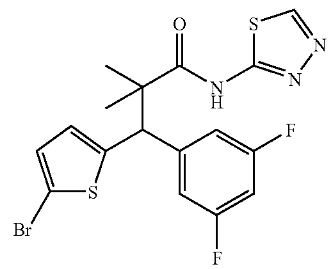 | 3.930 | 458.93 |

Examples 20 to 21

2,2-Dimethyl-3-(6-(4-morpholinyl)-3-pyridinyl)-3-phenyl-N-1,3-thiazol-2-ylpropanamide The title compound of Example 13 (42 mg) was resolved into its corresponding enantiomers by chiral preparative HPLC with the following conditions, Column: Chiralpak®-AD, 30×250 mm, Mobile phase: 60% (1:1 MeOH/EtOH)/40% hexane, Temperature: ambient, Flowrate: 20 mL/min, Detection: UV (254 nm). Retention times for the fast eluting enantiomer Example 19 (17 mg), 22 min, slow eluting enantiomer Example 20 (15 mg), 30 min. Analytical HPLC conditions, Column: Chiralpak®-AD, 4.6×250 mm, Mobile phase: 60% (1:1 MeOH/EtOH)/40% hexane, Temperature: ambient, Flowrate: 1 mL/min, Detection: UV (250 & 220 nm). Retention times: Enantiomer A, 9.14 (ee>99.9%) min; Enantiomer B, 12.48 min (ee>99.9%).

Examples 22 to 23

2,2-Dimethyl-3-(6-(4-morpholinyl)-3-pyridinyl)-3-phenyl-N-1,3,4-thiadiazol-2-ylpropanamide In a similar manner to Example 13, the title compound of Example 14 (53 mg) was resolved into its corresponding enantiomers, Enantiomer A, (18 mg) and Enantiomer B (14 mg), by chiral preparative HPLC. Analytical HPLC (Column: Chiralpak®-AD, 4.6×250 mm, Mobile phase: 60% (1:1 MeOH/EtOH)/40% hexane, Flowrate: 1 mL/min) Retention times: Enantiomer A: 5.64 min (ee>99.9%); Enantiomer B: 7.71 min (ee>99.9%)

| Example No. | Structure | MS [m/z (M + H)] | HPLC Rt: minute |
|---|---|---|---|
| 20 | Enantiomer A | 2.210 | 423.3 |
| 21 | Enantiomer B | 2.222 | 423.3 |

| Example No. | Structure | MS [m/z (M + H)] | HPLC Rt: minute |
|---|---|---|---|
| 22 | Enantiomer A | 1.972 | 424.16 |
| 23 | Enantiomer B | 1.970 | 424.16 |

Example 24

3-(6-(4-Methoxyphenyl)-3-pyridinyl)-2,2-dimethyl-3-phenyl-N-1,3,4-thiadiazol-2-ylpropanamide

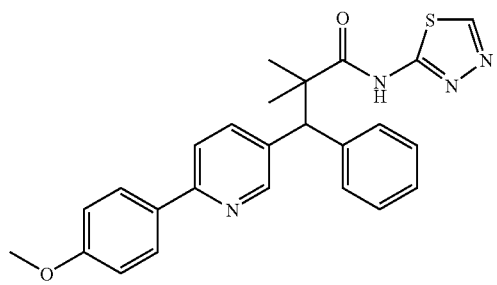

Step 1

A solution of 3-(6-chloro-pyridin-3-yl)-2,2-dimethyl-3-phenyl-propionic acid (Preparation 4, 100 mg, 0.345 mmol), 1-[3-(dimethylamino)propyl]-3-ethylcarbodiimide hydrochloride (EDC) (132 mg, 0.69 mmol) and 1-hydroxy-7-benzotriazole (HOBt) (93 mg, 0.69 mmol), 1,3,4-thiadiazol-2-amine (103 mg, 1.04 mmol) and diisopropylethyl amine (0.21 ml, 1.21 mmol) in CH3CN (1 mL) was heated at 75° C. for 12 hours. The reaction mixture was filtered, concentrated and purified by silica gel flash chromatography using 50% ethyl acetate in hexanes to give 3-(6-chloro-pyridin-3-yl)-2,2-dimethyl-3-phenyl-N-[1,3,4]thiadiazol-2-yl-propionamide as a white solid. (102 mg, 79.3% yield).). $^1$H NMR (400 MHz, CDCl$_3$): δ 1.31 (s, 3H), 1.32 (s, 3H), 4.57 (s, 1H), 7.15 (m, 1H), 7.20 (m, 2H), 7.28 (m, 3H), 7.85 (m, 1H), 8.26 (br s, 1H), 8.90 (s, 1H). LC/MS (m/z) 373.19 [(M+H)$^+$]; HPLC Rt: 2.913 min.

Step 2

An Emry™ process vial was charged with 3-(6-chloro-pyridin-3-yl)-2,2-dimethyl-3-phenyl-N-[1,3,4]thiadiazol-2-yl-propionamide (30 mg, 0.080 mmol) and 4-methoxy-phenylboronic acid (37 mg, 0.241 mmol), tetrakis(triphenylphosphine)palladium(0) (10 mg, 0.008 mmol), 0.080 mL of 2M K$_2$CO$_3$, and 1 mL of DMF. The reaction mixture was degassed by bubbling nitrogen through for 15 min, then sealed and exposed to microwave irradiation for 30 min at 150° C. The reaction mixture was cooled, filtered, and diluted with ethyl acetate. The organic solution was washed, dried and concentrated. The crude product was purified by silica gel flash chromatography using 50% ethyl acetate in hexanes to give the title compound of Example 24 as a white solid (18 mg, 51%). $^1$H NMR (400 MHz, CDCl$_3$): δ 1.46 (s, 3H), 1.47 (s, 3H), 3.85 (s, 3H), 4.72 (s, 1H), 7.02 (d, 2H, J=8.8 Hz), 7.25 (m, 1H), 7.32 (t, 2H, J=7.2 Hz), 7.45 (d, 2H, J=7.2), 7.73 (d, 1H, J=8.6 Hz), 7.86 (d, 2H, J=8.8 Hz), 7.97 (m, 1H), 8.56 (m, 1H), 9.00 (s, 1H). LC/MS (m/z) 445.24 [(M+H)$^+$]; HPLC Rt: 2.700 min.

Examples 25 to 26

In a similar manner to Example 24, Examples 25 to 26 were prepared via the Suzuki coupling reaction of the corresponding aryl boronic acids and 3-(6-chloro-pyridin-3-yl)-2,2-dimethyl-3-phenyl-N-thiazol-2-yl-propionamide, which was prepared from the acid of Preparation (4) and thiazol-2-ylamine in a manner similar to Example 24—Step 1. (Compounds are Racemic Unless Noted)

| Example No. | Name | Structure | MS [m/z (M + H)] | HPLC Rt: minute |
|---|---|---|---|---|
| 25 | 3-(6-(3-furyl)-3-pyridinyl)-2,2-dimethyl-3-phenyl-N-1,3-thiazol-2-ylpropanamide | 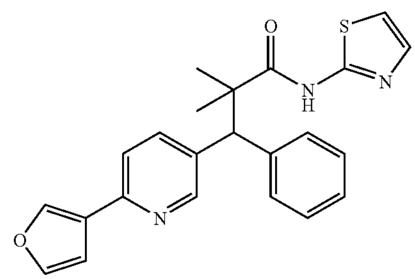 | 2.700 | 404.3 |
| 26 | 3-(6-(4-methoxyphenyl)-3-pyridinyl)-2,2-dimethyl-3-phenyl-N-1,3-thiazol-2-ylpropanamide | 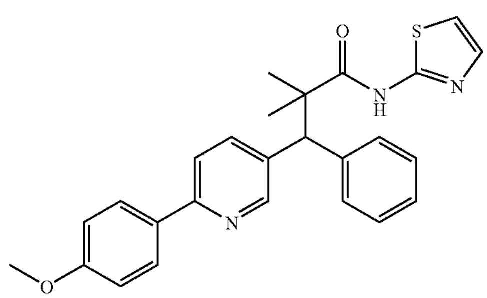 | 2.836 | 444.2 |

Examples 27 to 28

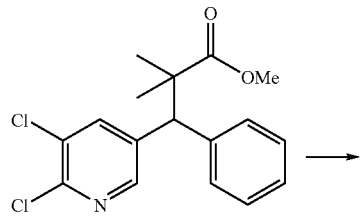

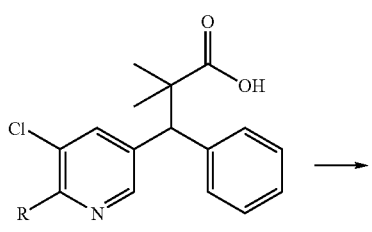

R = Cl/R = OMe 1:2

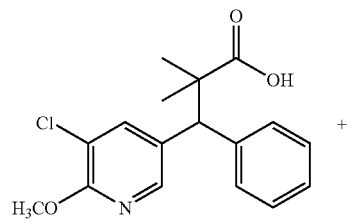

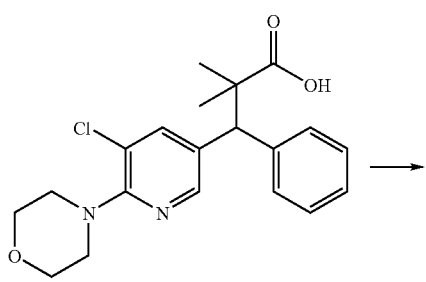

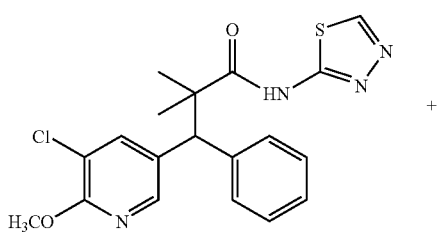

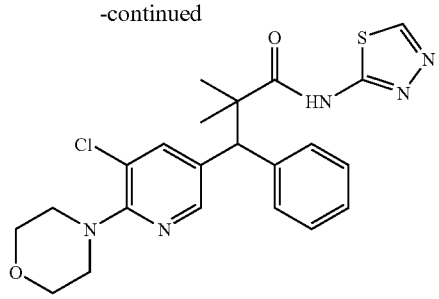

Example 27

3-(5-chloro-6-methoxy-3-pyridinyl)-2,2-dimethyl-3-phenyl-N-1,3,4-thiadiazol-2-ylpropanamide

Example 28

3-(5-chloro-6-(4-morpholinyl)-3-pyridinyl)-2,2-dimethyl-3-phenyl-N-1,3,4-thiadiazol-2-ylpropanamide 3-(5,6-Dichloro-pyridin-3-yl)-2,2-dimethyl-3-phenyl-propionic acid methyl ester (1.07 g, 3.17 mmol), prepared from acetic acid (5,6-dichloro-pyridin-3-yl)-phenyl-methyl ester according to the procedure described in Preparation 4, Step 2, was hydrolyzed in a similar manner to Preparation 1, Step 3, to produce a mixture of two acids (978 mg), 3-(5,6-dichloro-pyridin-3-yl)-2,2-dimethyl-3-phenyl-propionic acid and 3-(5-chloro-6-methoxy-pyridin-3-yl)-2,2-dimethyl-3-phenyl-propionic acid at a ratio of 1:2.

A portion of the mixed acids (200 mg) was dissolved in morpholine (1 ml) and heated at 140° C. for 4 hours. After being cooled, the reaction mixture was taken into ethyl ether and water. The solution was adjusted to pH 2 with 1N HCl. The organic layer was washed, dried, and concentrated to give a white amorphous solid (196 mg) as a mixture of 3-(5-chloro-6-methoxy-pyridin-3-yl)-2,2-dimethyl-3-phenyl-propionic acid and 3-(5-chloro-6-morpholin-4-yl-pyridin-3-yl)-2,2-dimethyl-3-phenyl-propionic acid. LC/MS (m/z) 320 [(M+H)$^+$] and 375 [(M+H)$^+$]; HPLC Rt: 3.701 min.

A mixture of the above two acids was reacted with [1,3,4]thiadiazol-2-ylamine according to the procedure described for Example 1. The crude product mixtures were purified via preparative HPLC to afford the title compounds of Examples 27 and 28.

Example 27 (19.4 mg), LC/MS (m/z) 403.07 [(M+H)$^+$]; HPLC Rt: 3.610 min.

Example 28 (20.4 mg), LC/MS (m/z) 458.12 [(M+H)$^+$]; HPLC Rt: 3.54 min.

Examples 29 to 33

In a similar manner to Example 24—Step 2, Examples 29 to 33 were prepared via the Suzuki coupling reaction of the corresponding aryl boronic acids and the title compound of Example 24—Step 1, 3-(6-chloro-pyridin-3-yl)-2,2-dimethyl-3-phenyl-N-[1,3,4]thiadiazol-2-yl-propionamide. (Compounds are racemic unless noted)

| Example No. | Name | Structure | MS [m/z (M + H)] | HPLC Rt: minute |
|---|---|---|---|---|
| 29 | 3-(6-(3-fluoro-4-isopropoxyphenyl)-3-pyridinyl)-2,2-dimethyl-3-phenyl-N-1,3,4-thiadiazol-2-ylpropanamide | 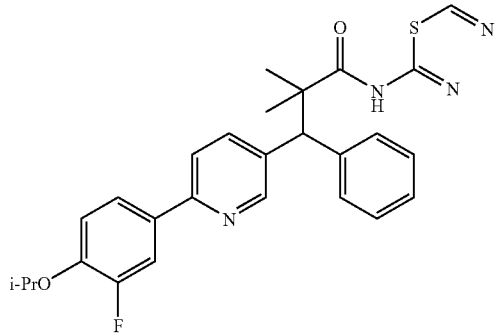 | 3.393 | 491.4 |
| 30 | 2,2-dimethyl-3-phenyl-3-(6-(4-propylphenyl)-3-pyridinyl)-N-1,3,4-thiadiazol-2-ylpropanamide | 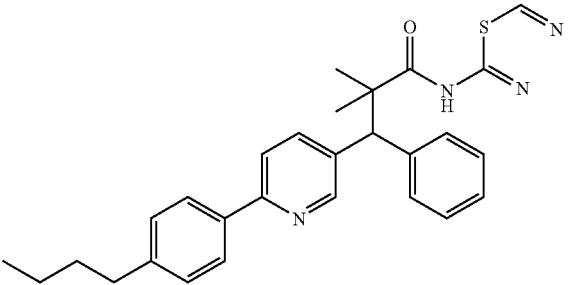 | 3.745 | 457.4 |
| 31 | 3-(6-(4-isobutylphenyl)-3-pyridinyl)-2,2-dimethyl-3-phenyl-N-1,3,4-thiadiazol-2-ylpropanamide | 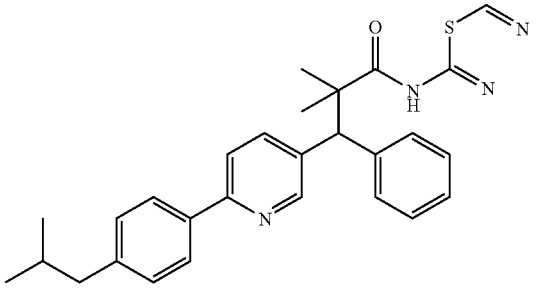 | 3.898 | 471.4 |
| 32 | 4-(5-(2,2-dimethyl-3-oxo-1-phenyl-3-(1,3,4-thiadiazol-2-ylamino)propyl)-2-pyridinyl)-N,N-dimethylbenzamide | 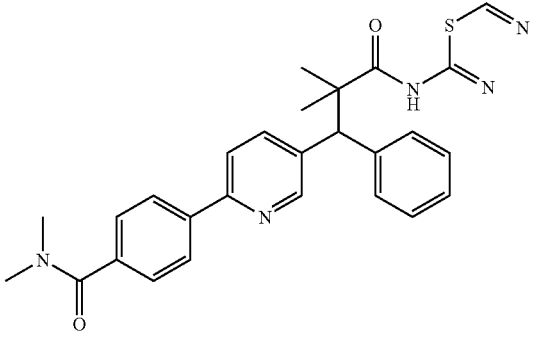 | 2.946 | 486.2 |
| 33 | 3-(6-(4-isopropoxyphenyl)-3-pyridinyl)-2,2-dimethyl-3-phenyl-N-1,3,4-thiadiazol-2-ylpropanamide | 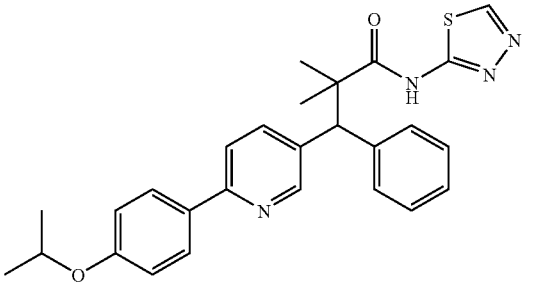 | 3.308 | 473.4 |

Example 34

(1S,2S,5R)-2-Amino-5-((7-anilino [1,3]thiazolo[5,4-b]pyridin-5-yl)amino)cyclohexanol

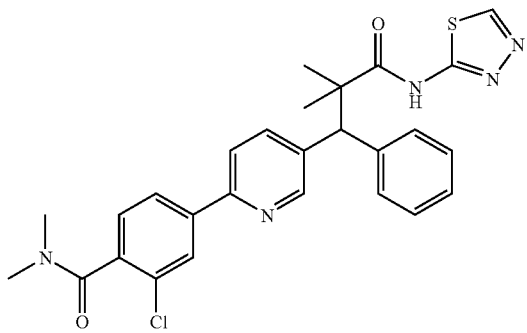

A scintillation vial was charged with 3-(6-chloro-pyridin-3-yl)-2,2-dimethyl-3-phenyl-N-[1,3,4]thiadiazol-2-yl-propionamide (30 mg, 0.068 mmol), 3-chloro-4-(dimethyl carbamoyl)phenylboronic acid (31 mg, 0.136 mmol), 0.136 mL (0.272 mmol) of 2M $K_2CO_3$, and 1 mL of DMF. The solution was degassed with nitrogen for 15 min. To this solution was added tetrakis (triphenyl phosphine)palladium(0) (10 mg, 0.008 mmol). The reaction mixture was degassed for additional 5 min, then sealed and heated in a heating block (OptiChem Digital Hotplate Stirrer) at 100° C. for 70 min. The reaction mixture was cooled, filtered, and diluted with ethyl acetate. The organic solution was washed, dried and concentrated. The crude product was purified by prep. HPLC to give the title compound of Example 34 as a white solid (17 mg, 48% yield). $^1$H NMR (400 MHz, MeOD): δ 8.97 (1H, s), 8.64 (1H, d, J=2.03 Hz), 8.09 (1H, s), 8.02 (1H, dd, J=8.39, 2.29 Hz), 7.96 (1H, br d, J=8.14 Hz), 7.85 (1H, br d, J=8.14 Hz), 7.37-7.50 (3H, m), 7.30 (2H, t, J=7.63 Hz), 7.22 (1H, m), 4.73 (1H, s), 3.12 (3H, s), 2.90 (3H, s), 1.46 (3H, s), 1.43 (3H, s). LC/MS (m/z) 520.6, 522.6 [(M+H)$^+$]; HPLC Rt: 3.365 min.

Examples 35 to 41

In a similar manner to Example 24—Step 2, Examples 35-41 were prepared via the Suzuki coupling reaction of the title compound of Example 1 and the corresponding aryl boronic acids. (Compounds are racemic unless noted)

| Example No. | Name | Structure | MS [m/z (M + H)] | HPLC Rt: minute |
|---|---|---|---|---|
| 35 | 3-(3-fluorophenyl)-3-(5-(4-methoxyphenyl)-2-thienyl)-2,2-dimethyl-N-1,3,4-thiadiazol-2-ylpropanamide | 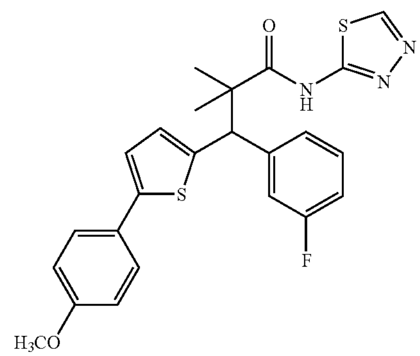 | 468.15 | 4.006 |
| 36 | 4-(5-(1-(3-fluorophenyl)-2,2-dimethyl-3-oxo-3-(1,3,4-thiadiazol-2-ylamino)propyl)-2-thienyl)-N,N-dimethylbenzamide | 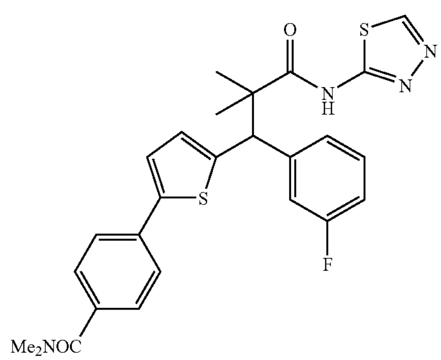 | 509.24 | 3.533 |

-continued

| Example No. | Name | Structure | MS [m/z (M + H)] | HPLC Rt: minute |
|---|---|---|---|---|
| 37 | 3-(5-(3-fluoro-4-isopropoxyphenyl)-2-thienyl)-3-(3-fluorophenyl)-2,2-dimethyl-N-1,3,4-thiadiazol-2-ylpropanamide | 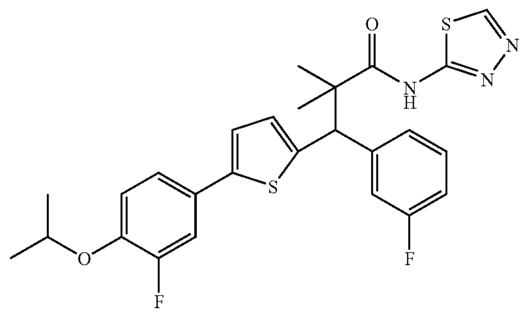 | 514.4 | 4.16 |
| 38 | 3-(3-fluorophenyl)-3-(5-(4-isopropoxyphenyl)-2-thienyl)-2,2-dimethyl-N-1,3,4-thiadiazol-2-ylpropanamide | 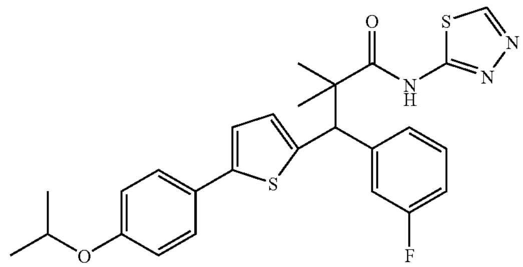 | 496.4 | 4.168 |
| 39 | 3-(3-fluorophenyl)-3-(5-(4-isobutylphenyl)-2-thienyl)-2,2-dimethyl-N-1,3,4-thiadiazol-2-ylpropanamide | 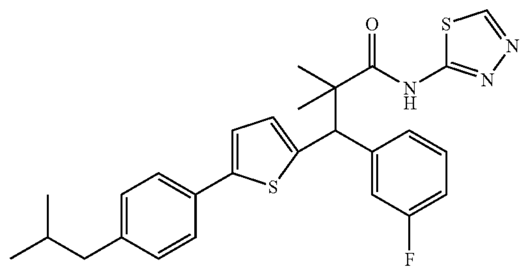 | 494.4 | 4.465 |
| 40 | -(3-fluorophenyl)-2,2-dimethyl-3-(5-(4-propylphenyl)-2-thienyl)-N-1,3,4-thiadiazol-2-ylpropanamide | 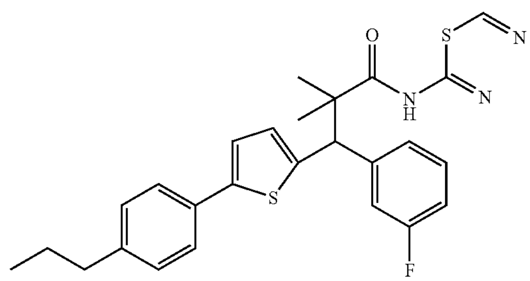 | 480.4 | 4.375 |
| 41 | 3-(3-fluorophenyl)-2,2-dimethyl-3-(5-(4-(1-pyrrolidinylcarbonyl)phenyl)-2-thienyl)-N-1,3,4-thiadiazol-2-ylpropanamide | 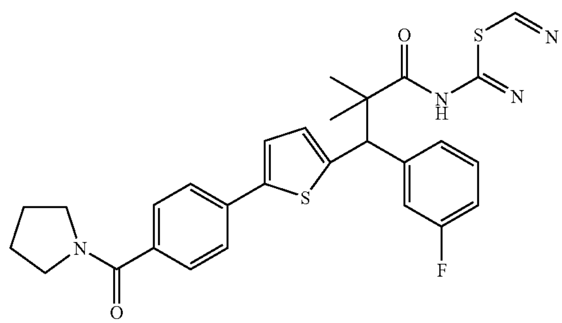 | 535.2 | 3.741 |

Example 42

4-(5-(1-(3-Fluorophenyl)-2,2-dimethyl-3-oxo-3-(1,3-thiazol-2-ylamino)propyl)-2-thienyl)-N,N-dimethylbenzamide

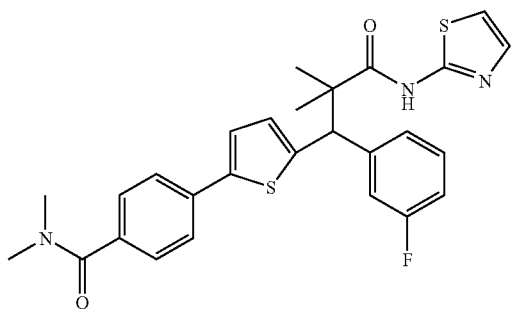

In a similar manner to Example 24—Step 2, the Suzuki coupling reaction of the title compound of Example 2 and 4-(dimethylcarbamoyl)phenylboronic acid afforded the title compound of Example 42. LC/MS (m/z) 508.4 [(M+H)$^+$]; HPLC Rt: 3.633 min.

Example 43

2-Chloro-4-(5-(2,2-dimethyl-3-oxo-1-phenyl-3-(1,3,4-thiadiazol-2-ylamino)propyl)-2-thienyl)-N,N-dimethylbenzamide

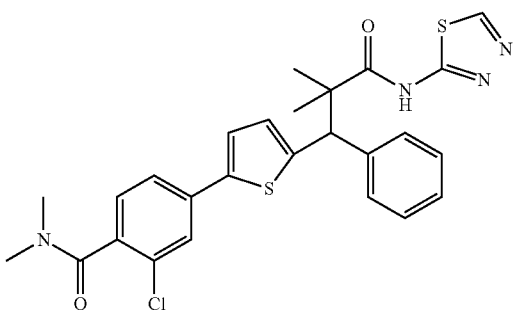

A scintillation vial was charged with the title compound of Example 3 (30 mg, 0.071 mmol), 3-chloro-4-(dimethyl carbamoyl)phenylboronic acid (33 mg, 0.143 mmol), 0.140 mL (0.85 mmol) of 2M K$_2$CO$_3$, and 1 mL of DMF. The solution was degassed with nitrogen for 15 min. To this solution was added tetrakis (triphenyl phosphine)palladium(0) (8.1 mg, 0.007 mmol). The reaction mixture was degassed for additional 5 min, then sealed and heated in a heating block (OptiChem Digital Hotplate Stirrer) at 100° C. for 30 min. The reaction mixture was cooled, filtered, and diluted with ethyl acetate. The organic solution was washed, dried and concentrated. The crude product was purified by prep. HPLC to give the title compound of Example 43 as a white solid (20.2 mg, 54% yield). $^1$H NMR (400 MHz, MeOD) δ 9.00 (1H, s), 7.65 (1H, d, J=2.03 Hz), 7.56 (1H, d, J=9.66 Hz), 7.46 (2H, d, J=7.12 Hz), 7.22-7.35 (5H, m), 7.06 (1H, d, J=4.07 Hz), 4.95 (1H, s), 3.10 (3H, s), 2.89 (3H, s), 1.46 (3H, s), 1.37 (3H, s). LC/MS (m/z) 525.11 [(M+H)$^+$]; HPLC Rt: 3.73 min.

Examples 44 to 53

In a similar manner to Example 41, Examples 44 to 53 were prepared via the Suzuki coupling reaction of the title compound of Example 3 and the corresponding aryl boronic acids. (Compounds are racemic unless noted)

| Example No. | Name | Structure | MS [m/z (M + H)] | HPLC Rt: minute |
|---|---|---|---|---|
| 44 | 4-(5-(2,2-dimethyl-3-oxo-1-phenyl-3-(1,3,4-thiadiazol-2-ylamino)propyl)-2-thienyl)-N,N-dimethylbenzamide | 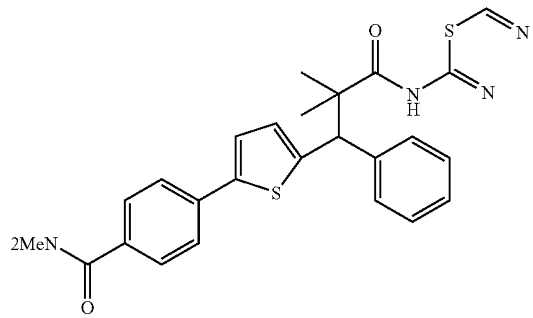 | 491.2 | 3.503 |

| Example No. | Name | Structure | MS [m/z (M + H)] | HPLC Rt: minute |
|---|---|---|---|---|
| 45 | 2,2-dimethyl-3-(5-(4-(4-morpholinylcarbonyl)phenyl)-2-thienyl)-3-phenyl-N-1,3,4-thiadiazol-2-ylpropanamide | 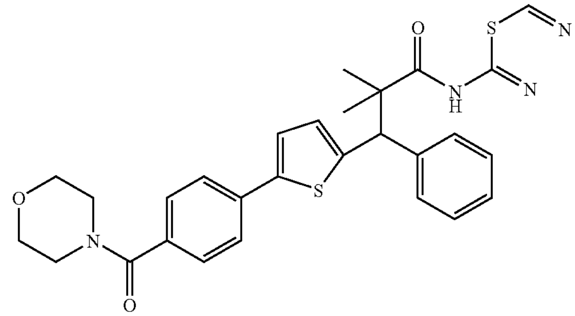 | 533.12 | 3.560 |
| 46 | 2,2-dimethyl-3-phenyl-3-(5-(4-(1-piperidinylcarbonyl)phenyl)-2-thienyl)-N-1,3,4-thiadiazol-2-ylpropanamide | 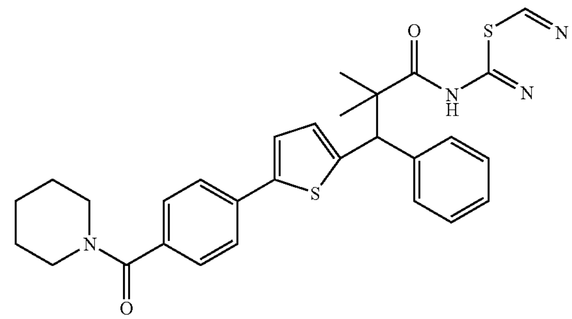 | 531.13 | 3.90 |
| 47 | 2,2-dimethyl-3-phenyl-3-(5-(4-(1-pyrrolidinylcarbonyl)phenyl)-2-thienyl)-N-1,3,4-thiadiazol-2-ylpropanamide | 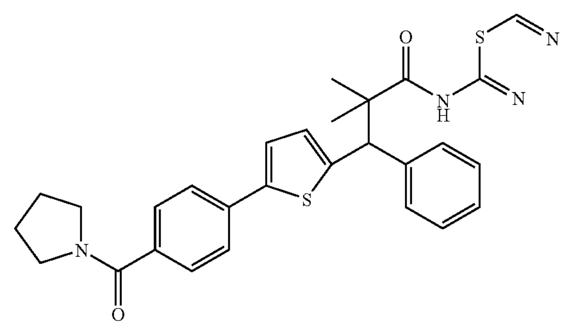 | 517.10 | 3.755 |
| 48 | 2-chloro-4-(5-(2,2-dimethyl-3-oxo-1-phenyl-3-(1,3,4-thiadiazol-2-ylamino)propyl)-2-thienyl)-N,N-diethylbenzamide | 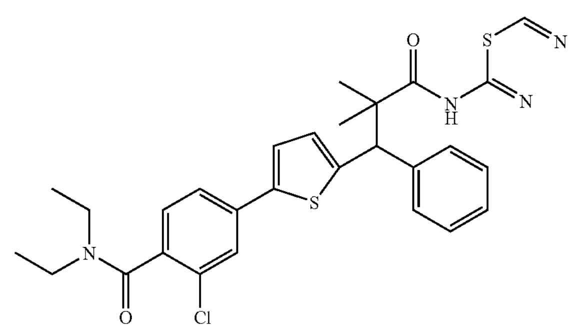 | 553.15 | 3.960 |

-continued

| Example No. | Name | Structure | MS [m/z (M + H)] | HPLC Rt: minute |
|---|---|---|---|---|
| 49 | 4-(5-(2,2-dimethyl-3-oxo-1-phenyl-3-(1,3,4-thiadiazol-2-ylamino)propyl)-2-thienyl)-N,N-diethylbenzamide | 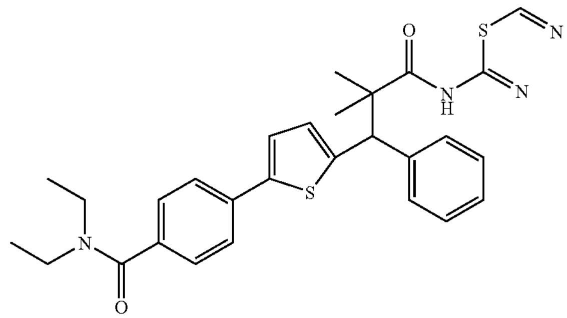 | 519.21 | 3.851 |
| 50 | 4-(5-(2,2-dimethyl-3-oxo-1-phenyl-3-(1,3,4-thiadiazol-2-ylamino)propyl)-2-thienyl)-N-ethyl-N-methylbenzamide | 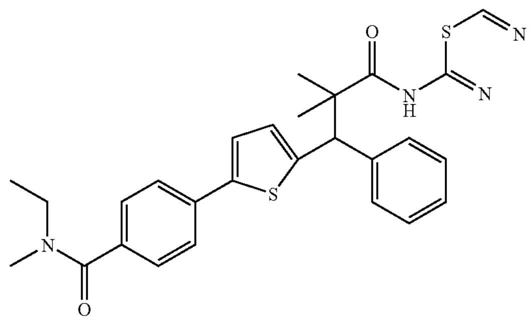 | 505.3 | 3.705 |
| 51 | 4-(5-(2,2-dimethyl-3-oxo-1-phenyl-3-(1,3,4-thiadiazol-2-ylamino)propyl)-2-thienyl)-N,N-dipropylbenzamide | 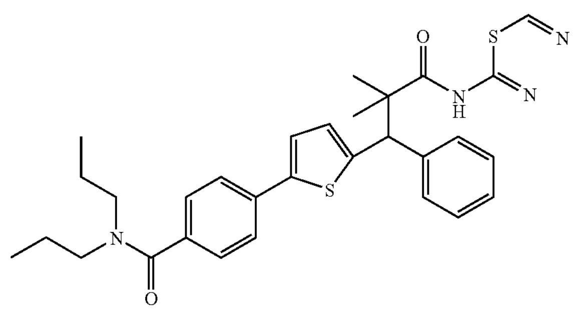 | 547.20 | 4.083 |
| 52 | 3-(5-(3-chloro-4-(4-morpholinylcarbonyl)phenyl)-2-thienyl)-2,2-dimethyl-3-phenyl-N-1,3,4-thiadiazol-2-ylpropanamide | 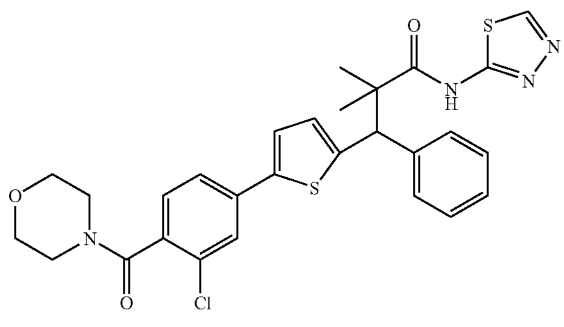 | 567.10 | 3.718 |

| Example No. | Name | Structure | MS [m/z (M + H)] | HPLC Rt: minute |
|---|---|---|---|---|
| 53 | methyl 4-(5-(2,2-dimethyl-3-oxo-1-phenyl-3-(1,3,4-thiadiazol-2-ylamino)propyl)-2-thienyl)-2-fluorobenzoate | 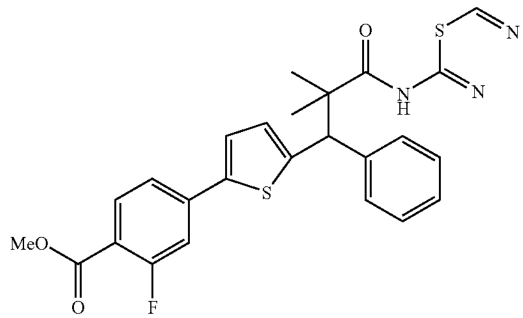 | 496.1 | 4.010 |

Example 54

4-(5-(2,2-Dimethyl-3-oxo-1-phenyl-3-(1,3-thiazol-2-ylamino)propyl)-2-thienyl)-N,N-dimethylbenzamide

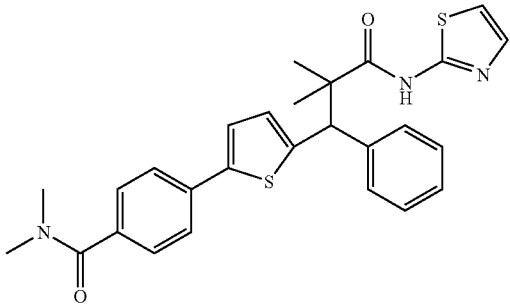

In a similar manner to Example 24—Step 2, the Suzuki coupling reaction of the title compound of Example 4 and 4-(dimethylcarbamoyl)phenylboronic acid afforded the title compound of Example 54. LC/MS (m/z) 490.4 [(M+H)$^+$]; HPLC Rt: 3.605 min.

Example 55

3-(5-(4-((4,4-Difluoro-1-piperidinyl)carbonyl)phenyl)-2-thienyl)-2,2-dimethyl-3-phenyl-N-1,3,4-thiadiazol-2-ylpropanamide

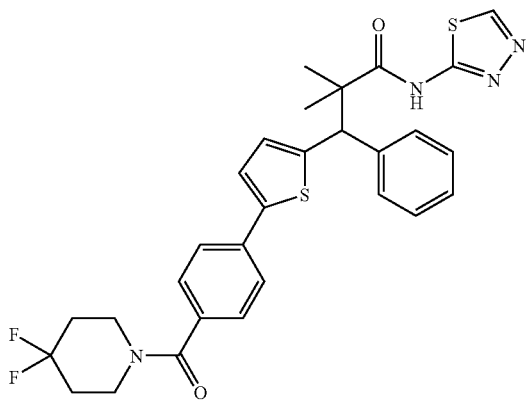

Step 1

A scintillation vial was charged with the title compound of Example 3 (30 mg, 0.071 mmol), 4-(methoxycarbonyl)phenylboronic acid (38 mg, 0.215 mmol), 0.140 mL (0.85 mmol) of 2M $K_2CO_3$, and 1.4 mL of DMF. The solution was degassed with nitrogen for 15 min. To this solution was added tetrakis(triphenyl phosphine)palladium(0) (8.1 mg, 0.007 mmol). The reaction mixture was degassed for additional 5 min, then sealed and heated in a heating block (OptiChem Digital Hotplate Stirrer) at 100° C. for 60 min. The reaction mixture was cooled, filtered, and diluted with ethyl acetate. The organic solution was washed, dried and concentrated. Purification via silica gel column (0-35% EtOAc in hexane) afforded methyl 4-(5-(3-(1,3,4-thiadiazol-2-ylamino)-2,2-dimethyl-3-oxo-1-phenylpropyl)thiophen-2-yl)benzoate as a white solid (18 mg, 53% yield). LC/MS (m/z) 478.29 [(M+H)$^+$]; HPLC Rt: 3.96 min

Step 2

In a similar manner to preparation 1, Step 3, the basic hydrolysis of the product of Step 1 afforded the crude acid. LC/MS (m/z) 462 [(M+H)$^+$]; HPLC Rt: 3.641 min.

Step 3

In a similar manner to Example 1, the amidation reaction of the acid from Step 2 with 3,3-difluoropyrrolidine gave the title compound of Example 55 (4 mg, 19% yield for 2 steps). LC/MS (m/z) 567.28 [(M+H)$^+$]; HPLC Rt: 3.716 min.

Examples 56 and 57

In a manner similar to the chiral separation of Example 13 which gave Examples 20 and 21, the title compound of Example 1 was resolved into its corresponding enantiomers using chiral supercritical fluid chromatography (Chiralpak®-OJ, $CO_2$/IPA: 80%/20%, 100 Bar). Analytical HPLC (Column: Chiralpak®-OJ, $CO_2$/IPA: 80%/20%) Retention times: (S)-enantiomer (Example 56), 8.92 min (ee>99.9%); (R)-enantiomer (Example 57), 10.44 min (ee>99.9%). A sample of Example 57 was crystallized in both neat and solvated forms. Single crystal analyses with anomalous scattering measurements defined the absolute stereochemistry (R) of Example 57.

| Example No. | Name | Structure | MS [m/z (M + H)] | HPLC Rt: minute |
|---|---|---|---|---|
| 56 | (3S)-3-(5-bromo-2-thienyl)-3-(3-fluorophenyl)-2,2-dimethyl-N-1,3,4-thiadiazol-2-ylpropanamide | (S)-Enantiomer | 440, 442 | 3.548 |
| 57 | (3R)-3-(5-bromo-2-thienyl)-3-(3-fluorophenyl)-2,2-dimethyl-N-1,3,4-thiadiazol-2-ylpropanamide | (R)-Enantiomer | 440, 442 | 3.548 |

Alternatively, the title compounds of Examples 56 and 57 can be prepared, in a similar manner to Example 1, via the amidation reactions of the acids of Preparations (7a) and (7b) with 1,3,4-thiadiazol-2-amine respectively.

Examples 58 to 63

In a similar manner to Example 43, Examples 58 to 63 were prepared via the Suzuki coupling reaction of the title compound of Example 56 and the corresponding aryl boronic acids. (All compounds have the S-configuration)

| Example No. | Name | Structure | MS [m/z (M + H)] | HPLC Rt: minute |
|---|---|---|---|---|
| 58 | 4-(5-((1S)-1-(3-fluorophenyl)-2,2-dimethyl-3-oxo-3-(1,3,4-thiadiazol-2-ylamino)propyl)-2-thienyl)-N,N-dimethylbenzamide | (S)-enantiomer | 509.4 | 3.518 |

-continued

| Example No. | Name | Structure | MS [m/z] (M + H)] | HPLC Rt: minute |
|---|---|---|---|---|
| 59 | (3S)-3-(3-fluorophenyl)-2,2-dimethyl-3-(5-(4-(4-morpholinylcarbonyl)phenyl)-2-thienyl)-N-1,3,4-thiadiazol-2-ylpropanamide | (S)-enantiomer | 551.5 | 3.578 |
| 60 | 2-chloro-4-(5-((1S)-1-(3-fluorophenyl)-2,2-dimethyl-3-oxo-3-(1,3,4-thiadiazol-2-ylamino)propyl)-2-thienyl)-N,N-dimethylbenzamide | (S)-enantiomer | 543.5 | 3.73 |
| 61 | (3S)-3-(5-(3-chloro-4-(4-morpholinylcarbonyl)phenyl)-2-thienyl)-3-(3-fluorophenyl)-2,2-dimethyl-N-1,3,4-thiadiazol-2-ylpropanamide | (S)-enantiomer | 585.2 | 3.720 |
| 62 | N-ethyl-4-(5-((1S)-1-(3-fluorophenyl)-2,2-dimethyl-3-oxo-3-(1,3,4-thiadiazol-2-ylamino)propyl)-2-thienyl)-N-methylbenzamide | (S)-enantiomer | 523.5 | 3.696 |

-continued

| Example No. | Name | Structure | MS [m/z (M + H)] | HPLC Rt: minute |
|---|---|---|---|---|
| 63 | 2-fluoro-4-(5-((1S)-1-(3-fluorophenyl)-2,2-dimethyl-3-oxo-3-(1,3,4-thiadiazol-2-ylamino)propyl)-2-thienyl)benzoic acid | 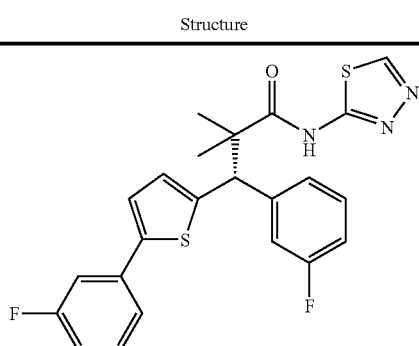<br>(S)-enantiomer | 500.1 | 3.733 |

Example 64

(3R)-3-(3-Fluorophenyl)-2,2-dimethyl-3-(5-(4-(4-morpholinylcarbonyl)phenyl)-2-thienyl)-N-1,3,4-thiadiazol-2-ylpropanamide

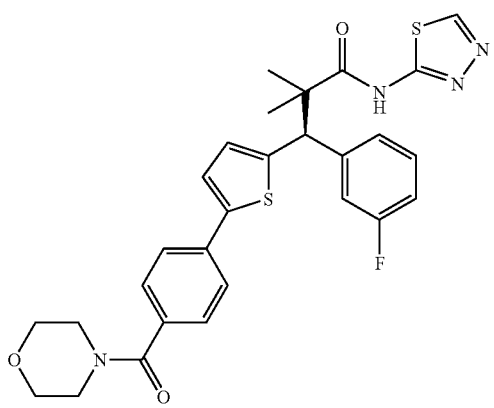

In a similar manner to Example 43, Examples 64 was prepared via the Suzuki coupling reaction. The title compound of Example 57 (200 mg, 0.454 mmol), and 4-(dimethylcarbamoyl)phenylboronic acid (213 mg, 0.908 mmol) in the presence of tetrakis (triphenyl phosphine)palladium(0) (52 mg, 0.045 mmol) in a solution of 2M $K_2CO_3$ (0.91 ml) and DMF (6 ml) afforded the title compound of Example 64 as a white solid (124 mg, 50% yield), after purification by prep HPLC. $^1$H NMR (400 MHz, MeOD) δ ppm 8.99 (1H, s) 7.64 (2H, d, J=8.14 Hz) 7.41 (2H, d, J=8.14 Hz) 7.23-7.36 (3H, m) 7.17-7.22 (1H, m) 7.06 (1H, d, J=4.07 Hz) 6.96-7.03 (1H, m) 4.97 (1H, s) 3.40-3.82 (8H, m) 1.46 (3H, s) 1.39 (3H, s). MS ESI (m/z) 551.3 [(M+H)$^+$]; HPLC Rt: 3.571 min.

Examples 65 to 82

In a similar manner to Example 43, Examples 65-82 were prepared via the Suzuki coupling reaction of the title compound of Example 57 and the corresponding aryl boronic acids. (All compounds have the R-configuration)

| Example No. | Name | Structure | MS [m/z (M + H)] | HPLC Rt: minute |
|---|---|---|---|---|
| 65 | 4-(5-((1R)-1-(3-fluorophenyl)-2,2-dimethyl-3-oxo-3-(1,3,4-thiadiazol-2-ylamino)propyl)-2-thienyl)-N,N-dimethylbenzamide | 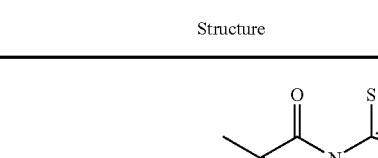<br>(R)-enantiomer | 509.4 | 3.525 |

-continued

| Example No. | Name | Structure | MS [m/z (M + H)] | HPLC Rt: minute |
|---|---|---|---|---|
| 66 | 2-chloro-4-(5-((1R)-1-(3-fluorophenyl)-2,2-dimethyl-3-oxo-3-(1,3,4-thiadiazol-2-ylamino)propyl)-2-thienyl)-N,N-dimethylbenzamide | (R)-enantiomer | 543.5 | 3.725 |
| 67 | (3R)-3-(5-(3-chloro-4-(4-morpholinylcarbonyl)phenyl)-2-thienyl)-3-(3-fluorophenyl)-2,2-dimethyl-N-1,3,4-thiadiazol-2-ylpropanamide | (R)-enantiomer | 585.5 | 3.703 |
| 68 | N-ethyl-4-(5-((1R)-1-(3-fluorophenyl)-2,2-dimethyl-3-oxo-3-(1,3,4-thiadiazol-2-ylamino)propyl)-2-thienyl)-N-methylbenzamide | (R)-enantiomer | 523.6 | 3.691 |
| 69 | N,N-diethyl-4-(5-((1R)-1-(3-fluorophenyl)-2,2-dimethyl-3-oxo-3-(1,3,4-thiadiazol-2-ylamino)propyl)-2-thienyl)benzamide | (R)-enantiomer | 537.3 | 3.821 |

-continued

| Example No. | Name | Structure | MS [m/z (M + H)] | HPLC Rt: minute |
|---|---|---|---|---|
| 70 | 2-chloro-N,N-diethyl-4-(5-((1R)-1-(3-fluorophenyl)-2,2-dimethyl-3-oxo-3-(1,3,4-thiadiazol-2-ylamino)propyl)-2-thienyl)benzamide | (R)-enantiomer | 571.2 | 3.936 |
| 71 | (3R)-3-(3-fluorophenyl)-2,2-dimethyl-3-(5-(4-(1-piperidinylcarbonyl)phenyl)-2-thienyl)-N-1,3,4-thiadiazol-2-ylpropanamide | (R)-enantiomer | 549.3 | 3.906 |
| 72 | 4-(5-((1R)-1-(3-fluorophenyl)-2,2-dimethyl-3-oxo-3-(1,3,4-thiadiazol-2-ylamino)propyl)-2-thienyl)-N,N-dipropylbenzamide | (R)-enantiomer | 565.2 | 4.070 |
| 73 | N-ethyl-4-(5-((1R)-1-(3-fluorophenyl)-2,2-dimethyl-3-oxo-3-(1,3,4-thiadiazol-2-ylamino)propyl)-2-thienyl)benzamide | (R)-enantiomer | 509.2 | 3.621 |

-continued

| Example No. | Name | Structure | MS [m/z (M + H)] | HPLC Rt: minute |
|---|---|---|---|---|
| 74 | 4-(5-((1R)-1-(3-fluorophenyl)-2,2-dimethyl-3-oxo-3-(1,3,4-thiadiazol-2-ylamino)propyl)-2-thienyl)benzamide | (R)-enantiomer | 481.1 | 3.441 |
| 75 | 4-(5-((1R)-1-(3-fluorophenyl)-2,2-dimethyl-3-oxo-3-(1,3,4-thiadiazol-2-ylamino)propyl)-2-thienyl)-N-methylbenzamide | (R)-enantiomer | 495.2 | 3.541 |
| 76 | N-tert-butyl-4-(5-((1R)-1-(3-fluorophenyl)-2,2-dimethyl-3-oxo-3-(1,3,4-thiadiazol-2-ylamino)propyl)-2-thienyl)benzamide | (R)-enantiomer | 537.2 | 3.883 |
| 77 | N-cyclopropyl-4-(5-((1R)-1-(3-fluorophenyl)-2,2-dimethyl-3-oxo-3-(1,3,4-thiadiazol-2-ylamino)propyl)-2-thienyl)benzamide | (R)-enantiomer | 521.2 | 3.666 |

-continued

| Example No. | Name | Structure | MS [m/z (M + H)] | HPLC Rt: minute |
|---|---|---|---|---|
| 78 | 2-fluoro-4-(5-((1R)-1-(3-fluorophenyl)-2,2-dimethyl-3-oxo-3-(1,3,4-thiadiazol-2-ylamino)propyl)-2-thienyl)benzoic acid | (R)-enantiomer | 500.1 | 3.728 |
| 79 | (3R)-3-(5-(4-((3,3-difluoro-1-pyrrolidinyl)carbonyl)phenyl)-2-thienyl)-3-(3-fluorophenyl)-2,2-dimethyl-N-1,3,4-thiadiazol-2-ylpropanamide | (R)-enantiomer | 571 | 3.703 |
| 80 | N-ethyl-2-fluoro-4-(5-((1R)-1-(3-fluorophenyl)-2,2-dimethyl-3-oxo-3-(1,3,4-thiadiazol-2-ylamino)propyl)-2-thienyl)-N-methylbenzamide | (R)-enantiomer | 541.13 | 3.708 |
| 81 | (3R)-3-(5-(4-(1-azetidinylcarbonyl)phenyl)-2-thienyl)-3-(3-fluorophenyl)-2,2-dimethyl-N-1,3,4-thiadiazol-2-ylpropanamide | (R)-enantiomer | 521.16 | 3.635 |

| Example No. | Name | Structure | MS [m/z (M + H)] | HPLC Rt: minute |
|---|---|---|---|---|
| 82 | (3R)-3-(5-(4-(1-azetidinylcarbonyl)-3-fluorophenyl)-2-thienyl)-3-(3-fluorophenyl)-2,2-dimethyl-N-1,3,4-thiadiazol-2-ylpropanamide | (R)-enantiomer | 539.1 | 3.660 |

Example 83

(3R)-3-(5-(3-Fluoro-4-(4-morpholinylcarbonyl)phenyl)-2-thienyl)-3-(3-fluorophenyl)-2,2-dimethyl-N-1,3,4-thiadiazol-2-ylpropanamide

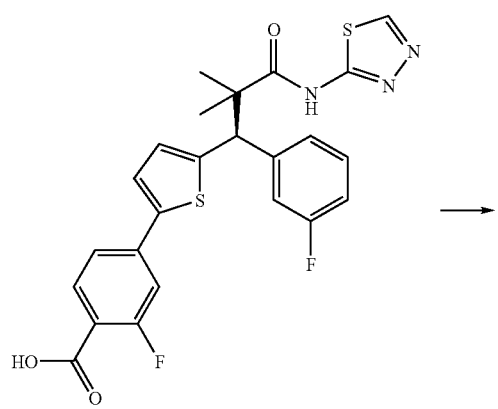

To a solution of the title compound of Example 78 (25 mg, 0.05 mmol) in CH₃CN (1 mL) were added 1-[3-(dimethylamino)propyl]-3-ethylcarbodiimide hydrochloride (EDC) (19 mg, 0.10 mmol) and 1-hydroxy-7-benzotriazole (HOBt) (14 mg, 0.10 mmol). After stirring for 5 minutes, to the solution were added morpholine (0.013 ml, 0.15 mmol) and diisopropylethyl amine (0.031 ml, 0.18 mmol). The reaction was heated at 60° C. for 18 hours. The reaction mixture was filtered, concentrated and purified by prep HPLC to give the title compound of Example 83 as a white solid (14 mg, 49% yield). $^1$H NMR (400 MHz, MeOD) δ ppm 9.00 (1H, s) 7.47 (1H, dd, J=8.06, 1.76 Hz) 7.39-7.44 (1H, m) 7.36 (1H, d, J=8.06 Hz) 7.29-7.34 (2H, m) 7.25-7.29 (1H, m) 7.20 (1H, dd, J=12.34, 2.01 Hz) 7.08 (1H, d, J=3.78 Hz) 7.00 (1H, t, J=7.81 Hz) 4.98 (1H, s) 3.75 (4H, d, J=4.03 Hz) 3.59-3.65 (2H, m) 3.34-3.40 (2H, m) 1.46 (3H, s) 1.39 (3H, s). MS ESI (m/z) 569.3 [(M+H)⁺]; HPLC Rt: 3.606 min.

Examples 84 and 85

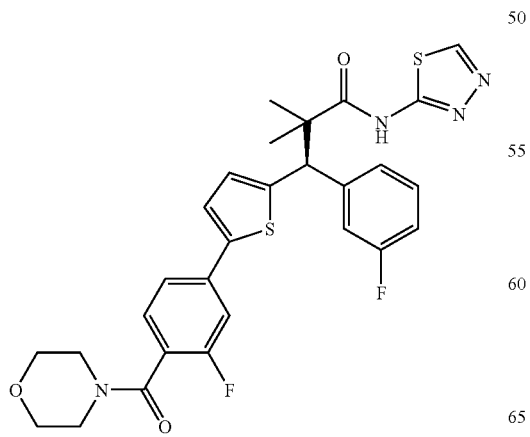

In a similar manner to Example 1, Examples 84 and 85 were prepared via the amidation reactions of the acids of Preparations (6a) and (6b) with 1,3,4-thiadiazol-2-amine respectively. (All compounds are enantiomerically pure. The absolute stereochemistry have not been determined.)

| Example No. | Name | Structure | MS [m/z (M + H)] | HPLC Rt: minute |
|---|---|---|---|---|
| 84 | 3-(5-bromo-2-thienyl)-2,2-dimethyl-3-phenyl-N-1,3,4-thiadiazol-2-ylpropanamide | (chiral) | 422, 424 | 3.80 |
| 85 | 3-(5-bromo-2-thienyl)-2,2-dimethyl-3-phenyl-N-1,3,4-thiadiazol-2-ylpropanamide | (chiral) | 422, 424 | 3.798 |

Examples 86 to 88

In a similar manner to Example 43, Examples 86 to 88 were prepared via the Suzuki coupling reaction of the title compound of Example 84 and the corresponding aryl boronic acids. (All compounds are enantiomerically pure.)

| Example No. | Name | Structure | MS [m/z (M + H)] | HPLC Rt: minute |
|---|---|---|---|---|
| 86 | 2-chloro-4-(5-(2,2-dimethyl-3-oxo-1-phenyl-3-(1,3,4-thiadiazol-2-ylamino)propyl)-2-thienyl)-N,N-dimethylbenzamide | (chiral) | 525.2 | 3.675 |

| Example No. | Name | Structure | MS [m/z] (M + H)] | HPLC Rt: minute |
|---|---|---|---|---|
| 87 | 4-(5-(2,2-dimethyl-3-oxo-1-phenyl-3-(1,3,4-thiadiazol-2-ylamino)propyl)-2-thienyl)-N,N-dimethylbenzamide | (chiral) | 491.2 | 3.54 |
| 88 | 4-(5-(2,2-dimethyl-3-oxo-1-phenyl-3-(1,3,4-thiadiazol-2-ylamino)propyl)-2-thienyl)-N-ethyl-N-methylbenzamide | (chiral) | 505.2 | 3.663 |

Examples 89 to 92

In a similar manner to Example 43, Examples 89 to 92 were prepared via the Suzuki coupling reaction of the title compound of Example 19 and the corresponding aryl boronic acids. (All compounds are racemic.)

| Example No. | Name | Structure | MS [m/z] (M + H)] | HPLC Rt: minute |
|---|---|---|---|---|
| 89 | 3-(3,5-difluorophenyl)-2,2-dimethyl-3-(5-(4-(4-morpholinylcarbonyl)phenyl)-2-thienyl)-N-1,3,4-thiadiazol-2-ylpropanamide | 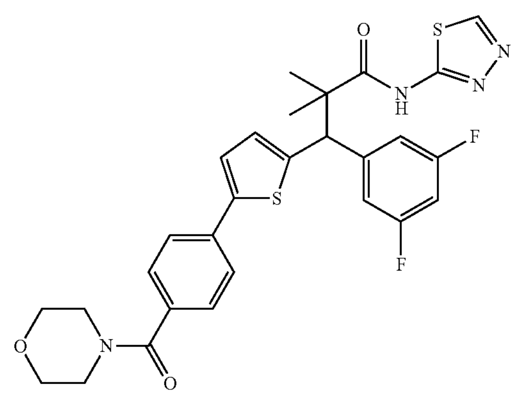 | 569.1 | 3.651 |

| Example No. | Name | Structure | MS [m/z (M + H)] | HPLC Rt: minute |
|---|---|---|---|---|
| 90 | 4-(5-(1-(3,5-difluorophenyl)-2,2-dimethyl-3-oxo-3-(1,3,4-thiadiazol-2-ylamino)propyl)-2-thienyl)-N,N-dimethylbenzamide | 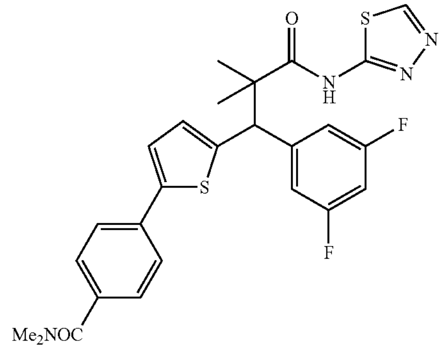 | 527.1 | 3.683 |
| 91 | 2-chloro-4-(5-(1-(3,5-difluorophenyl)-2,2-dimethyl-3-oxo-3-(1,3,4-thiadiazol-2-ylamino)propyl)-2-thienyl)-N,N-dimethylbenzamide | 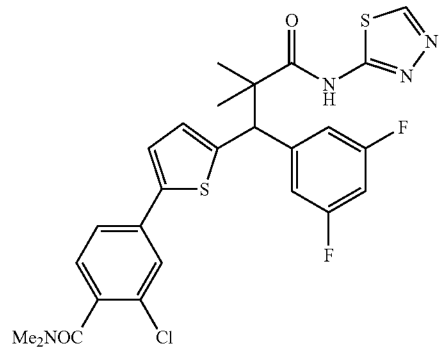 | 561.1 | 3.806 |
| 92 | 4-(5-(1-(3,5-difluorophenyl)-2,2-dimethyl-3-oxo-3-(1,3,4-thiadiazol-2-ylamino)propyl)-2-thienyl)-N-ethyl-N-methylbenzamide | 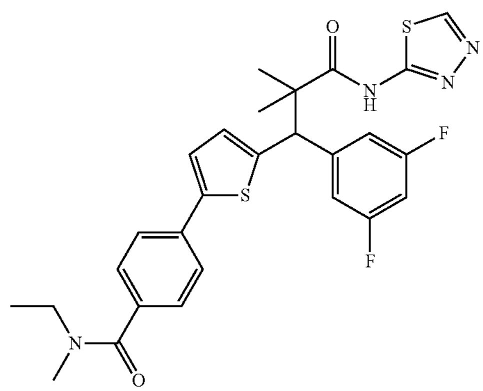 | 541.1 | 3.793 |

Examples 93 to 97

In a similar manner to Example 1, Examples 93 to 97 were prepared via the amidation reactions of 3-(5-bromothiophen-2-yl)-3-(3-fluorophenyl)-2-methylpropanoic acids, the acids of Preparations (8a), (9a), (9b), (9c) and (9d) with 1,3,4-thiadiazol-2-amine, respectively. Examples 94-97 are optically pure and their absolute stereochemistries have been determined, shown in the Table below. Example 93 is a 1:1 diastereomeric mixture.

| Example No. | Name | Structure | MS [m/z (M + H)] | HPLC Rt: minute |
|---|---|---|---|---|
| 93 | 3-(5-bromo-2-thienyl)-3-(3-fluorophenyl)-2-methyl-N-1,3,4-thiadiazol-2-ylpropanamide | 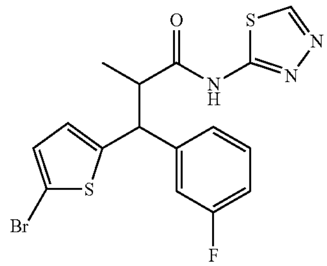 | 426, 428 | 3.650 |
| 94 | (2S,3S)-3-(5-bromo-2-thienyl)-3-(3-fluorophenyl)-2-methyl-N-1,3,4-thiadiazol-2-ylpropanamide | 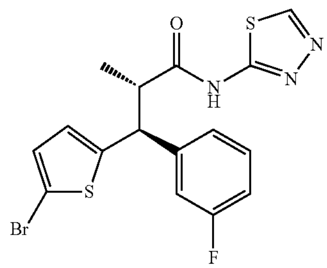 | 425.9, 427.9 | 3.631 |
| 95 | (2S,3R)-3-(5-bromo-2-thienyl)-3-(3-fluorophenyl)-2-methyl-N-1,3,4-thiadiazol-2-ylpropanamide | 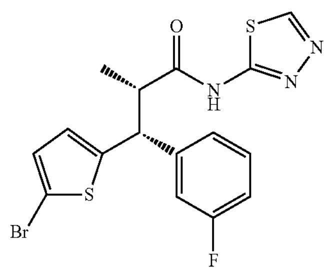 | 425.9, 427.9 | 3.595 |
| 96 | (2R,3S)-3-(5-bromo-2-thienyl)-3-(3-fluorophenyl)-2-methyl-N-1,3,4-thiadiazol-2-ylpropanamide | 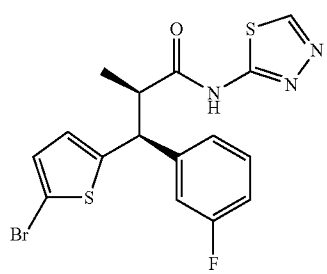 | 425.9, 427.9 | 3.603 |
| 97 | (2R,3R)-3-(5-bromo-2-thienyl)-3-(3-fluorophenyl)-2-methyl-N-1,3,4-thiadiazol-2-ylpropanamide | 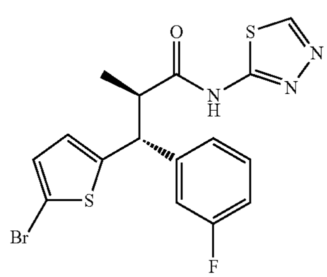 | 426, 427.9 | 3.631 |

Examples 98 and 99

N-ethyl-4-(5-(1-(3-fluorophenyl)-2-methyl-3-oxo-3-(1,3,4-thiadiazol-2-ylamino)propyl)-2-thienyl)-N-methylbenzamide (diastereomers A and B)

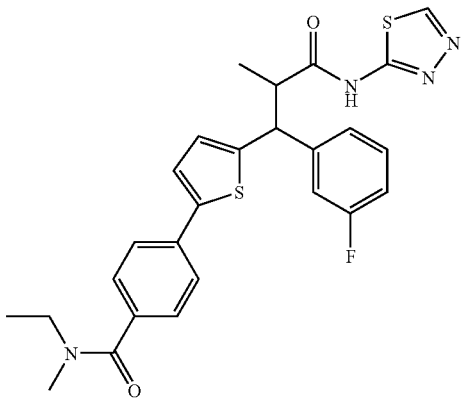

In a similar manner to Example 43, Examples 98 and 99 were prepared via a Suzuki coupling reaction. The title compound of Example 93, 3-(5-bromothiophen-2-yl)-3-(3-fluorophenyl)-2-methyl-N-(1,3,4-thiadiazol-2-yl)propanamide (50 mg, 0.117 mmol), and 4-(dimethylcarbamoyl)phenylboronic acid (49 mg, 0.234 mmol) in the presence of tetrakis(triphenyl phosphine)palladium(0) (14 mg, 0.012 mmol) in a 2M aqueous solution of $K_2CO_3$ (1 ml) and DMF (1 ml) afforded the crude product as a 1:1 diastereomeric mixture. The diastereomer pair were separated by preparative HPLC to give the fast eluting isomer A as the title compound of Example 98 and the slow eluting isomer B as the title compound of Example 99. Example 98 (white solid, 18 mg): $^1$H NMR (400 MHz, MeOD) δ ppm 8.96 (1H, s) 7.67 (2H, d, J=8.31 Hz) 7.40 (2H, t, J=7.30 Hz) 7.34 (1H, d, J=3.78 Hz) 7.19-7.28 (2H, m) 7.15 (1H, d, J=10.07 Hz) 7.10 (1H, d, J=3.78 Hz) 6.82-6.90 (1H, m) 4.49 (1H, d, J=11.33 Hz) 3.48-3.61 (2H, m) 3.32-3.38 (1H, m) 3.03 (3H, d, J=25.68 Hz) 1.32 (3H, d, J=6.80 Hz) 1.12-1.27 (3H, m). MS ESI (m/z) 509.3 [(M+H)$^+$]; HPLC Rt: 3.521 min. Example 99 (white solid, 16 mg): $^1$H NMR (400 MHz, MeOD) δ ppm 8.99 (1H, s) 7.56 (2H, d, J=8.31 Hz) 7.29-7.45 (3H, m) 7.26 (1H, d, J=7.55 Hz) 7.15-7.22 (2H, m) 6.98-7.07 (1H, m) 6.96 (1H, d, J=3.53 Hz) 4.53 (1H, d, J=11.58 Hz) 3.45-3.61 (2H, m) 3.30 (m, 1H) 2.99 (3H, d, J=30.97 Hz) 1.06-1.25 (6H, m). MS ESI (m/z) 509.3 [(M+H)$^+$]; HPLC Rt: 3.566 min.

Examples 100 to 105

In a similar manner to Example 43, the Suzuki coupling reaction of the compound of Example 93 and the corresponding aryl boronic acids afforded the coupling products as diastereomer pairs. Each diastereomer pair were separated by pre HPLC to give the title compounds of Examples 100 to 105. (All compounds are racemic)

| Example No. | Name | Structure | HPLC Rt: minute | MS [m/z (M + H)] |
|---|---|---|---|---|
| 100 | 3-(3-fluorophenyl)-2-methyl-3-(5-(4-(4-morpholinylcarbonyl)phenyl)-2-thienyl)-N-1,3,4-thiadiazol-2-ylpropanamide | Diastereomer 1 | 537.2 | 3.353 |
| 101 | 3-(3-fluorophenyl)-2-methyl-3-(5-(4-(4-morpholinylcarbonyl)phenyl)-2-thienyl)-N-1,3,4-thiadiazol-2-ylpropanamide | Diastereomer 2 | 537.2 | 3.426 |

-continued

| Example No. | Name | Structure | HPLC Rt: minute | MS [m/z (M + H)] |
|---|---|---|---|---|
| 102 | 4-(5-(1-(3-fluorophenyl)-2-methyl-3-oxo-3-(1,3,4-thiadiazol-2-ylamino)propyl)-2-thienyl)-N,N-dimethylbenzamide | 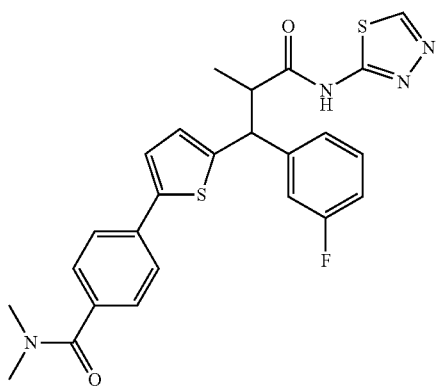<br>Diastereomer 1 | 495.2 | 3.386 |
| 103 | 4-(5-(1-(3-fluorophenyl)-2-methyl-3-oxo-3-(1,3,4-thiadiazol-2-ylamino)propyl)-2-thienyl)-N,N-dimethylbenzamide | 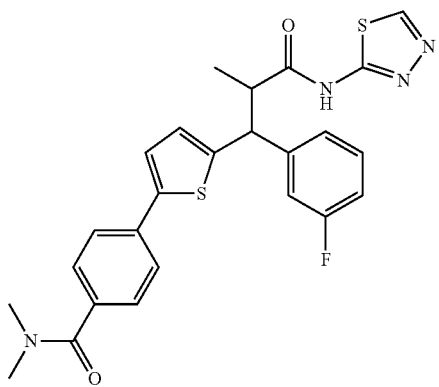<br>Diastereomer 2 | 495.2 | 3.446 |
| 104 | 2-chloro-4-(5-(1-(3-fluorophenyl)-2-methyl-3-oxo-3-(1,3,4-thiadiazol-2-ylamino)propyl)-2-thienyl)-N,N-dimethylbenzamide | 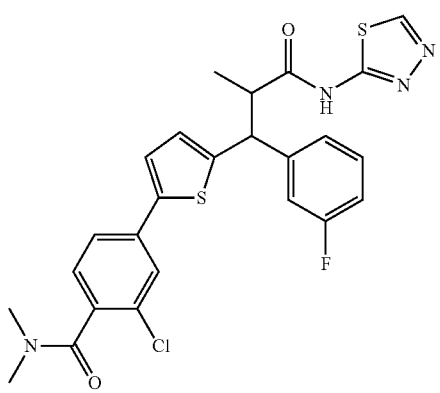<br>Diastereomer 1 | 529.2 | 3.523 |

-continued

| Example No. | Name | Structure | HPLC Rt: minute | MS [m/z (M + H)] |
|---|---|---|---|---|
| 105 | 2-chloro-4-(5-(1-(3-fluorophenyl)-2-methyl-3-oxo-3-(1,3,4-thiadiazol-2-ylamino)propyl)-2-thienyl)-N,N-dimethylbenzamide | Diastereomer 2 | 529.2 | 3.581 |

Examples 106 and 107

The title compound of Example 98 was resolved into its corresponding enantiomers using chiral supercritical fluid chromatography (SFC) with the following conditions.

Chiral-SFS Prep. Conditions: Column: Chiralpak AS-H (3×25 cm, 5 µm); BPR Pressure 100 bars; Temperature: 35° C.; Mobil Phase: CO2/MeOH (70/30); Flow rate: 70 mL/min; UV Detection: 308 nm.

Analytical HPLC conditions: Column: Chiralpak AS (0.46×25 cm, 10 µm) Mobile phase: CO2/MeOH (70/30), Temperature: 35° C., Flowrate: 2 mL/min, Detection: 308 nm). Retention times: (2S,3S)-isomer (Example 106), 13.55 min (ee>99.9%); (2R,3R)-isomer (Example 107), 16.65 min (ee>99.9%).

| Example No. | Name | Structure | MS [m/z (M + H)] | HPLC Rt: minute |
|---|---|---|---|---|
| 106 | N-ethyl-4-(5-((1S,2S)-1-(3-fluorophenyl)-2-methyl-3-oxo-3-(1,3,4-thiadiazol-2-ylamino)propyl)-2-thienyl)-N-methylbenzamide | (2S,3S) | 509.1 | 3.485 |
| 107 | N-ethyl-4-(5-((1R,2R)-1-(3-fluorophenyl)-2-methyl-3-oxo-3-(1,3,4-thiadiazol-2-ylamino)propyl)-2-thienyl)-N-methylbenzamide | (2R,3R) | 509 | 3.488 |

Alternatively, the title compound of Example 107 can be prepared via the Suzuki coupling reaction of Example 97 and 4-(ethyl(methyl)carbamoyl)phenylboronic acid in a similar manner to Example 43.

Examples 108 to 109

In a similar manner to the chiral separation of Example 98 to give Examples 106 and 107, the title compound of Example 100 was resolved into the corresponding enantiomers using chiral supercritical fluid chromatography (SFC). Analytical HPLC (Column: Chiralpak AS, CO2/MeOH 70:30, Flowrate: 2 mL/min, Detection: 220&254 nm) Retention times: (2S, 3S)-enantiomer (Example 108), 23.87 min (ee>99.9%); (2R, 3R)-enantiomer (Example 109), 29.31 min (ee>99.9%).

| Example No. | Name | Structure | MS [m/z (M + H)] | HPLC Rt: minute |
|---|---|---|---|---|
| 108 | (2S,3S)-3-(3-fluorophenyl)-2-methyl-3-(5-(4-(4-morpholinylcarbonyl)phenyl)-2-thienyl)-N-1,3,4-thiadiazol-2-ylpropanamide | (2S,3S) | 537 | 3.318 |
| 109 | (2R,3R)-3-(3-fluorophenyl)-2-methyl-3-(5-(4-(4-morpholinylcarbonyl)phenyl)-2-thienyl)-N-1,3,4-thiadiazol-2-ylpropanamide | (2R,3R) | 537.1 | 3.308 |

Example 110

2-Chloro-4-(5-((1R,2R)-1-(3-fluorophenyl)-2-methyl-3-oxo-3-(1,3,4-thiadiazol-2-ylamino)propyl)-2-thienyl)-N,N-dimethylbenzamide

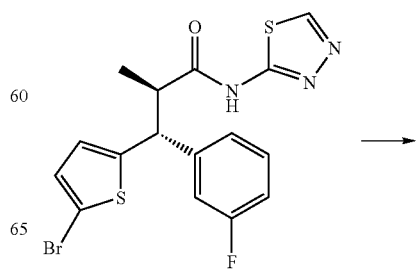

-continued

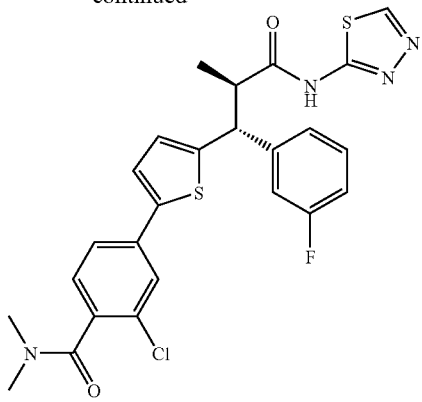

In a similar manner to Example 43, the Suzuki coupling reaction of the title compound of Example 97, (2R,3R)-3-(5-bromothiophen-2-yl)-3-(3-fluorophenyl)-2-methyl-N-(1,3,4-thiadiazol-2-yl)propanamide (240 mg, 0.563 mmol), and 3-chloro-4-(dimethyl-carbamoyl)phenylboronic acid (256 mg, 1.126 mmol) afforded the title compound of Example 110 (147 mg, 0.278 mmol, 49.4% yield). $^1$H NMR (400 MHz, MeOD) δ ppm 8.96 (1H, s) 7.71 (1H, d, J=1.51 Hz) 7.61 (1H, dd, J=7.93, 1.64 Hz) 7.39 (1H, d, J=3.78 Hz) 7.33 (1H, d, J=8.06 Hz) 7.19-7.28 (2H, m) 7.15 (1H, dd, J=10.07, 2.01 Hz) 7.11 (1H, d, J=3.78 Hz) 6.83-6.89 (1H, m) 4.51 (1H, d, J=1.33 Hz) 3.48-3.57 (1H, m) 3.11 (3H, s) 2.91 (3H, s) 1.32 (3H, d, J=6.55 Hz). LC/MS (m/z) 529.11 (M+H)$^{+1}$; HPLC Rt: 3.448 min.

Examples 111 to 122

In a similar manner to Example 43, Examples 111 to 122 were prepared via the Suzuki coupling reaction of the title compound of Example 97, and the corresponding aryl boronic acids. (All compounds have the (2R,3R)-configuration)

| Example No. | Name | Structure | MS [m/z (M + H)] | HPLC Rt: minute |
|---|---|---|---|---|
| 111 | (2R,3R)-3-(5-(3-chloro-4-(4-morpholinylcarbonyl)phenyl)-2-thienyl)-3-(3-fluorophenyl)-2-methyl-N-1,3,4-thiadiazol-2-ylpropanamide | 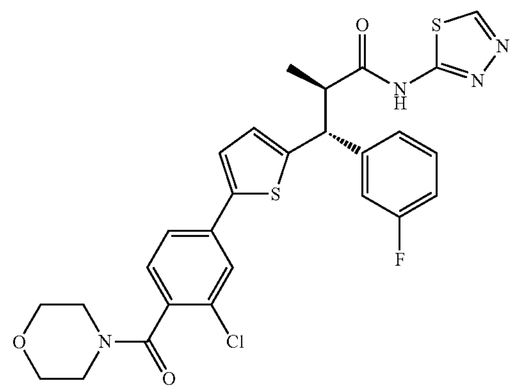 | 571 | 3.448 |
| 112 | 2-fluoro-4-(5-((1R,2R)-1-(3-fluorophenyl)-2-methyl-3-oxo-3-(1,3,4-thiadiazol-2-ylamino)propyl)-2-thienyl)-N,N-dimethylbenzamide | 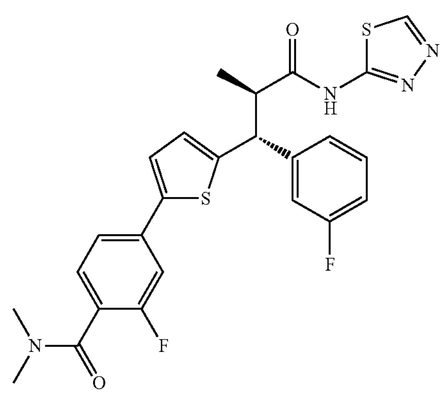 | 513.1 | 3.400 |

| Example No. | Name | Structure | MS [m/z (M + H)] | HPLC Rt: minute |
|---|---|---|---|---|
| 113 | (2R,3R)-3-(3-fluorophenyl)-3-(5-(4-isopropoxyphenyl)-2-thienyl)-2-methyl-N-1,3,4-thiadiazol-2-ylpropanamide | (2R,3R) | 482.1 | 4.065 |
| 114 | (2R,3R)-3-(3-fluorophenyl)-3-(5-(4-isobutylphenyl)-2-thienyl)-2-methyl-N-1,3,4-thiadiazol-2-ylpropanamide | (2R,3R) | 480.1 | 4.370 |
| 115 | (2R,3R)-3-(5-(3-chloro-4-(1-pyrrolidinylcarbonyl)phenyl)-2-thienyl)-3-(3-fluorophenyl)-2-methyl-N-1,3,4-thiadiazol-2-ylpropanamide | (2R,3R) | 555 | 3.646 |

| Example No. | Name | Structure | MS [m/z (M + H)] | HPLC Rt: minute |
|---|---|---|---|---|
| 116 | (2R,3R)-3-(3-fluorophenyl)-3-(5-(3-fluoro-4-(1-pyrrolidinylcarbonyl)phenyl)-2-thienyl)-2-methyl-N-1,3,4-thiadiazol-2-ylpropanamide | 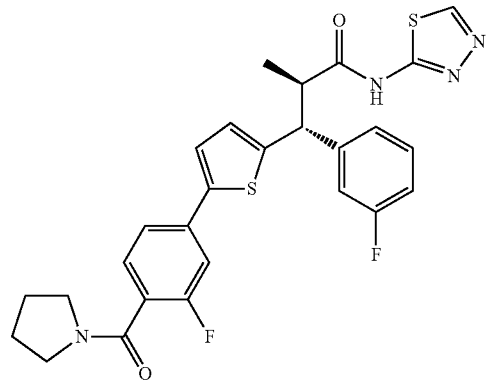 | 539.1 | 3.570 |
| 117 | 4-(5-((1R,2R)-1-(3-fluorophenyl)-2-methyl-3-oxo-3-(1,3,4-thiadiazol-2-ylamino)propyl)-2-thienyl)-N,N-dimethylbenzamide | 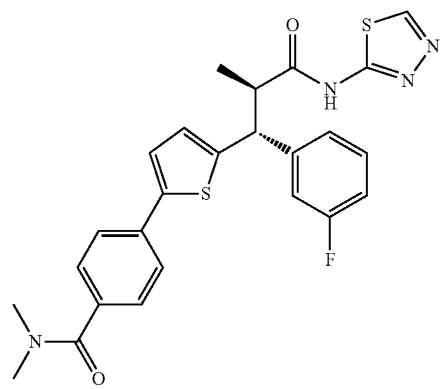 | 495 | 3.350 |
| 118 | (2R,3R)-3-(3-fluorophenyl)-2-methyl-3-(5-(4-(1-pyrrolidinylcarbonyl)phenyl)-2-thienyl)-N-1,3,4-thiadiazol-2-ylpropanamide | 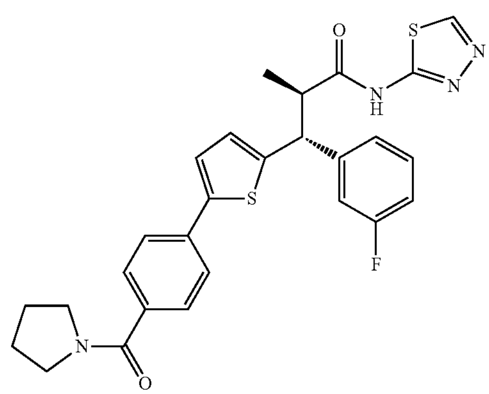 | 521.1 | 3.540 |

| Example No. | Name | Structure | MS [m/z (M + H)] | HPLC Rt: minute |
|---|---|---|---|---|
| 119 | 2-chloro-N-ethyl-4-(5-((1R,2R)-1-(3-fluorophenyl)-2-methyl-3-oxo-3-(1,3,4-thiadiazol-2-ylamino)propyl)-2-thienyl)-N-methylbenzamide | (2R,3R) | 543.1 | 3.635 |
| 120 | N-ethyl-2-fluoro-4-(5-((1R,2R)-1-(3-fluorophenyl)-2-methyl-3-oxo-3-(1,3,4-thiadiazol-2-ylamino)propyl)-2-thienyl)-N-methylbenzamide | (2R,3R) | 527.1 | 3.535 |
| 121 | (2R,3R)-3-(5-(4-((3,3-difluoro-1-pyrrolidinyl)carbonyl)phenyl)-2-thienyl)-3-(3-fluorophenyl)-2-methyl-N-1,3,4-thiadiazol-2-ylpropanamide | (2R,3R) | 557.1 | 3.556 |

-continued

| Example No. | Name | Structure | MS [m/z (M + H)] | HPLC Rt: minute |
|---|---|---|---|---|
| 122 | (2R,3R)-3-(5-(4-(1-azetidinylcarbonyl)-3-fluorophenyl)-2-thienyl)-3-(3-fluorophenyl)-2-methyl-N-1,3,4-thiadiazol-2-ylpropanamide | (2R,3R) | 525.1 | 3.473 |

Examples 123 to 125

In a similar manner to Example 43, Examples 123-125 were prepared via the Suzuki coupling reaction of the title compound of Example 94, (2S,3S)-3-(5-bromothiophen-2-yl)-3-(3-fluorophenyl)-2-methyl-N-(1,3,4-thiadiazol-2-yl)propanamide, and the corresponding aryl boronic acids. (All compounds have the (2S,3S)-configuration.)

| Example No. | Name | Structure | MS [m/z (M + H)] | HPLC Rt: minute |
|---|---|---|---|---|
| 123 | 2-chloro-4-(5-((1S,2S)-1-(3-fluorophenyl)-2-methyl-3-oxo-3-(1,3,4-thiadiazol-2-ylamino)propyl)-2-thienyl)-N,N-dimethylbenzamide | (2S,3S) | 529.1 | 3.488 |
| 124 | (2S,3S)-3-(5-(3-chloro-4-(4-morpholinylcarbonyl)phenyl)-2-thienyl)-3-(3-fluorophenyl)-2-methyl-N-1,3,4-thiadiazol-2-ylpropanamide | (2S,3S) | 571.1 | 3.473 |

-continued

| Example No. | Name | Structure | MS [m/z (M + H)] | HPLC Rt: minute |
|---|---|---|---|---|
| 125 | 4-(5-((1S,2S)-1-(3-fluorophenyl)-2-methyl-3-oxo-3-(1,3,4-thiadiazol-2-ylamino)propyl)-2-thienyl)-N,N-dimethylbenzamide | (2S,3S) | 495 | 3.360 |

Examples 126 to 128

In a similar manner to Example 43, Examples 126 to 128 were prepared via the Suzuki coupling reaction of the title compound of Example 95, (2S,3R)-3-(5-bromothiophen-2-yl)-3-(3-fluorophenyl)-2-methyl-N-(1,3,4-thiadiazol-2-yl)propanamide, and the corresponding aryl boronic acids. (All compounds have the (2S,3R)-configuration.)

| Example No. | Name | Structure | MS [m/z (M + H)] | HPLC Rt: minute |
|---|---|---|---|---|
| 126 | 2-chloro-4-(5-((1R,2S)-1-(3-fluorophenyl)-2-methyl-3-oxo-3-(1,3,4-thiadiazol-2-ylamino)propyl)-2-thienyl)-N,N-dimethylbenzamide | (2S,3R) | 529 | 3.555 |
| 127 | (2S,3R)-3-(5-(3-chloro-4-(4-morpholinylcarbonyl)phenyl)-2-thienyl)-3-(3-fluorophenyl)-2-methyl-N-1,3,4-thiadiazol-2-ylpropanamide | (2S,3R) | 571 | 3.538 |

-continued

| Example No. | Name | Structure | MS [m/z (M + H)] | HPLC Rt: minute |
|---|---|---|---|---|
| 128 | 4-(5-((1R,2S)-1-(3-fluorophenyl)-2-methyl-3-oxo-3-(1,3,4-thiadiazol-2-ylamino)propyl)-2-thienyl)-N,N-dimethylbenzamide | (2S,3R) | 495 | 3.411 |

Examples 129 to 131

In a similar manner to Example 43, Examples 129 to 131 were prepared via the Suzuki coupling reaction of the title compound of Example 96, (2R,3S)-3-(5-bromothiophen-2-yl)-3-(3-fluorophenyl)-2-methyl-N-(1,3,4-thiadiazol-2-yl)propanamide, and the corresponding aryl boronic acids. (All compounds have the (2R,3S)-configuration.)

| Example No. | Name | Structure | MS [m/z (M + H)] | HPLC Rt: minute |
|---|---|---|---|---|
| 129 | 2-chloro-4-(5-((1S,2R)-1-(3-fluorophenyl)-2-methyl-3-oxo-3-(1,3,4-thiadiazol-2-ylamino)propyl)-2-thienyl)-N,N-dimethylbenzamide | (2R,3S) | 529 | 3.548 |
| 130 | (2R,3S)-3-(5-(3-chloro-4-(4-morpholinylcarbonyl)phenyl)-2-thienyl)-3-(3-fluorophenyl)-2-methyl-N-1,3,4-thiadiazol-2-ylpropanamide | (2R,3S) | 571 | 3.543 |

-continued

| Example No. | Name | Structure | MS [m/z (M + H)] | HPLC Rt: minute |
|---|---|---|---|---|
| 131 | 4-(5-((1S,2R)-1-(3-fluorophenyl)-2-methyl-3-oxo-3-(1,3,4-thiadiazol-2-ylamino)propyl)-2-thienyl)-N,N-dimethylbenzamide | (2R,3S) | 495 | 3.421 |

Examples 132 to 136

In a similar manner to Example 1, Examples 132 to 136 were prepared via the amidation reactions of the acids of Preparations (8b), (10a), (10b), (10c) and (10d) with 1,3,4-thiadiazol-2-amine, respectively. Examples 133-136 are optically pure. The absolute stereochemistry of Examples 133 and 138 have been determined, shown in the Table. Example 132 is a 1:1 diastereomeric mixture.

| Example No. | Name | Structure | MS [m/z (M + H)] | HPLC Rt: minute |
|---|---|---|---|---|
| 132 | 3-(5-bromo-2-thienyl)-2-methyl-3-phenyl-N-1,3,4-thiadiazol-2-ylpropanamide | 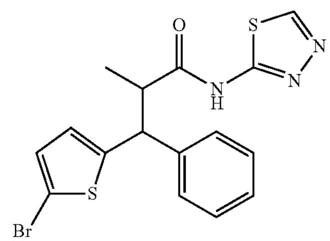 | 408, 410 | 3.596 |
| 133 | (2S,3S)-3-(5-bromo-2-thienyl)-2-methyl-3-phenyl-N-1,3,4-thiadiazol-2-ylpropanamide | (2S,3S) | 407.9, 409.9 | 3.570 |
| 134 | 3-(5-bromo-2-thienyl)-2-methyl-3-phenyl-N-1,3,4-thiadiazol-2-ylpropanamide | (chiral) | 407.9, 409.9 | 3.545 |

| Example No. | Name | Structure | MS [m/z (M + H)] | HPLC Rt: minute |
|---|---|---|---|---|
| 135 | 3-(5-bromo-2-thienyl)-2-methyl-3-phenyl-N-1,3,4-thiadiazol-2-ylpropanamide | (chiral) | 407.9, 409.9 | 3.548 |
| 136 | (2R,3R)-3-(5-bromo-2-thienyl)-2-methyl-3-phenyl-N-1,3,4-thiadiazol-2-ylpropanamide | (2R,3R) | 408, 409.9 | 3.565 |

Example 137 to 140

In a similar manner to Example 43, Examples 137 to 140 were prepared via the Suzuki coupling reaction of the Examples 133, 134, 135 and 136 with 4-(dimethylcarbamoyl)phenylboronic acid. All compounds are optically pure. The absolute stereochemistry of Examples 137 and 140 have been determined, shown in the Table.

| Example No. | Name | Structure | MS [m/z (M + H)] | HPLC Rt: minute |
|---|---|---|---|---|
| 137 | N,N-dimethyl-4-(5-((1S,2S)-2-methyl-3-oxo-1-phenyl-3-(1,3,4-thiadiazol-2-ylamino)propyl)-2-thienyl)benzamide | (2S,3S) | 477.2 | 3.311 |
| 138 | N,N-dimethyl-4-(5-(2-methyl-3-oxo-1-phenyl-3-(1,3,4-thiadiazol-2-ylamino)propyl)-2-thienyl)benzamide | (chiral) | 477.1 | 3.366 |

-continued

| Example No. | Name | Structure | MS [m/z (M + H)] | HPLC Rt: minute |
|---|---|---|---|---|
| 139 | N,N-dimethyl-4-(5-(2-methyl-3-oxo-1-phenyl-3-(1,3,4-thiadiazol-2-ylamino)propyl)-2-thienyl)benzamide | (chiral) | 477.1 | 3.371 |
| 140 | N,N-dimethyl-4-(5-((1R,2R)-2-methyl-3-oxo-1-phenyl-3-(1,3,4-thiadiazol-2-ylamino)propyl)-2-thienyl)benzamide | (2R,3R) | 477.1 | 3.296 |

Example 141

N-Ethyl-4-(5-((1R,2R)-1-(3-fluorophenyl)-2-methyl-3-((5-methyl-1,3,4-thiadiazol-2-yl)amino)-3-oxopropyl)-2-thienyl)-N-methylbenzamide

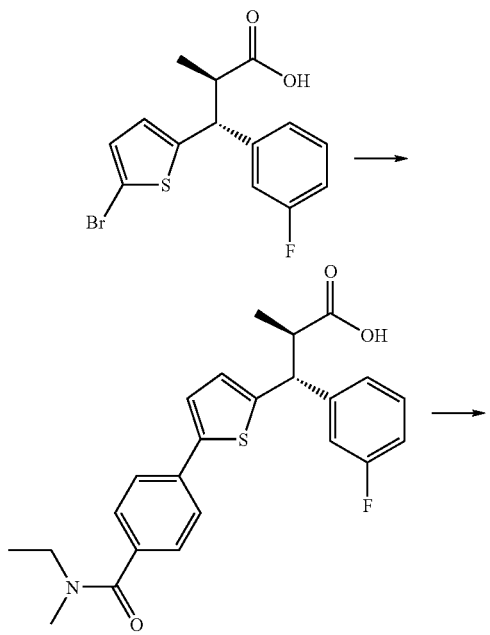

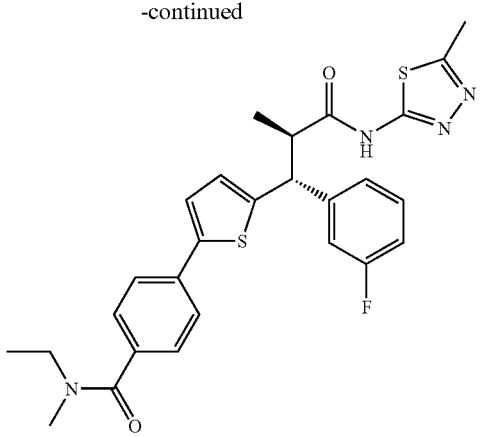

Step 1

A scintillation vial was charged with the title compound of Example 97, (2R,3R)-3-(5-bromothiophen-2-yl)-3-(3-fluorophenyl)-2-methylpropanoic acid (200 mg, 0.583 mmol), 4-(ethyl(methyl)carbamoyl)phenylboronic acid (241 mg, 1.165 mmol) and 2M aqueous solution of $K_2CO_3$ (1.165 mL, 2.331 mmol) in DMF (4 ml). The solution was degassed with nitrogen for 15 min. To this solution was added tetrakis (triphenylphosphine) palladium(0) (67.3 mg, 0.058 mmol). The reaction mixture was degassed for additional 5 min, then sealed and heated in a heating block (OptiChem Digital Hotplate Stirrer) at 100° C. for 20 min. The reaction mixture was taken into 1N NaOH solution and DCM. The aqueous layer was adjusted to pH of 3-4 with concentrated HCl. The acidic aqueous solution was extracted with ethyl acetate three times. The combined organic phases were washed, dried over MgSO4, filtered and concentrated to afford (2R,3R)-3-(5-(4-(ethyl(methyl)carbamoyl)phenyl)thiophen-2-yl)-3-(3-fluorophenyl)-2-methylpropanoic acid as a gum (120 mg). LC/MS (m/z) 426.16 [(M+H)+]; HPLC Rt: 3.475 min.

Step 2

To a solution of the compound from Step 1, (2R,3R)-3-(5-(4-(ethyl(methyl)carbamoyl)phenyl)thiophen-2-yl)-3-(3-fluorophenyl)-2-methylpropanoic acid (30 mg, 0.071 mmol) in acetonitrile (1 mL) were added HOBT (21.59 mg, 0.141 mmol) and EDC (27.0 mg, 0.141 mmol). The reaction was stirred for 5 minutes at room temperature. To this solution was added 5-methyl-1,3,4-thiadiazol-2-amine (24.36 mg, 0.212 mmol) followed by Hunig's Base (0.043 mL, 0.247 mmol). The reaction was stirred at 75° C. for 18 hrs. The reaction was filtered and concentrated in vacuo. The crude product was purified using prep HPLC [C18; Luna 5 microns; 21×100 mm; 20 mL/min; 220 wavelength; gradient 60 to 100% solvent B (water/MeOH/TFA 10:90:0.1) in 12 min. with 3 min holding. Product eluted at Rt=10.379 min.] to afford the title compound of Example 141 as a white solid (14 mg, 37.6% yield). 1H NMR (400 MHz, MeOD) δ ppm 7.67 (2H, d, J=8.56 Hz) 7.41 (2H, t, J=8.06 Hz) 7.34 (1H, d, J=3.53 Hz) 7.17-7.29 (2H, m) 7.11-7.17 (1H, m) 7.09 (1H, d, J=3.78 Hz) 6.82-6.92 (1H, m) 4.47 (1H, d, J=11.33 Hz) 3.52-3.63 (1H, m) 3.44-3.52 (1H, m) 3.34 (1H, d, J=9.06 Hz) 3.03 (3H, d, J=24.93 Hz) 2.60 (3H, s) 1.30 (3H, d, J=6.80 Hz) 1.11-1.26 (3H, m). MS ESI (m/z) 523.2 [(M+H)+]; HPLC Rt: 3.625 min.

Examples 142 and 143

In a similar manner to Example 1, Examples 142-143 were prepared via the amidation reactions of the acid from the Example 141—Step 1 with 5-methylthiazol-2-amine and thiazol-2-amine respectively.

| Example No. | Name | Structure | MS [m/z (M + H)] | HPLC Rt: minute |
|---|---|---|---|---|
| 142 | N-ethyl-4-(5-((1R,2R)-1-(3-fluorophenyl)-2-methyl-3-((5-methyl-1,3-thiazol-2-yl)amino)-3-oxopropyl)-2-thienyl)-N-methylbenzamide | (2R,3R) | 522.2 | 3.760 |
| 143 | N-ethyl-4-(5-((1R,2R)-1-(3-fluorophenyl)-2-methyl-3-oxo-3-(1,3-thiazol-2-ylamino)propyl)-2-thienyl)-N-methylbenzamide | (2R,3R) | 508.2 | 3.610 |

Examples 144 to 151

In a similar manner to Example 43, the Suzuki coupling reaction of the title compound of Example 132 and the corresponding aryl boronic acids afforded the coupling products as diastereomer pairs. Each diastereomer pair were separated by pre HPLC to give the title compounds of Examples 144-151. (All compounds are racemic.)

| Example No. | Name | Structure | MS [m/z] (M + H)] | HPLC Rt: minute |
|---|---|---|---|---|
| 144 | 2-methyl-3-(5-(4-(4-morpholinylcarbonyl)phenyl)-2-thienyl)-3-phenyl-N-1,3,4-thiadiazol-2-ylpropanamide | 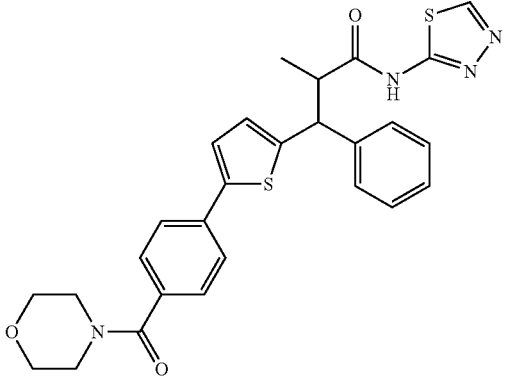<br>Diastereomer 1 | 519.2 | 3.663 |
| 145 | 2-methyl-3-(5-(4-(4-morpholinylcarbonyl)phenyl)-2-thienyl)-3-phenyl-N-1,3,4-thiadiazol-2-ylpropanamide | 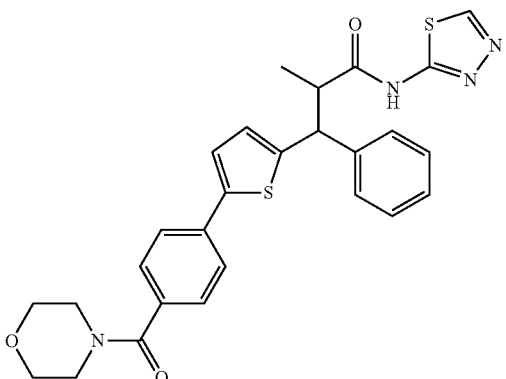<br>Diastereomer 2 | 519.2 | 3.381 |
| 146 | N,N-dimethyl-4-(5-(2-methyl-3-oxo-1-phenyl-3-(1,3,4-thiadiazol-2-ylamino)propyl)-2-thienyl)benzamide | 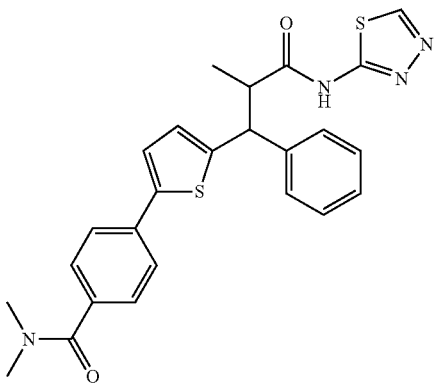<br>Diastereomer 1 | 477.1 | 3.326 |

| Example No. | Name | Structure | MS [m/z] (M + H)] | HPLC Rt: minute |
|---|---|---|---|---|
| 147 | N,N-dimethyl-4-(5-(2-methyl-3-oxo-1-phenyl-3-(1,3,4-thiadiazol-2-ylamino)propyl)-2-thienyl)benzamide | 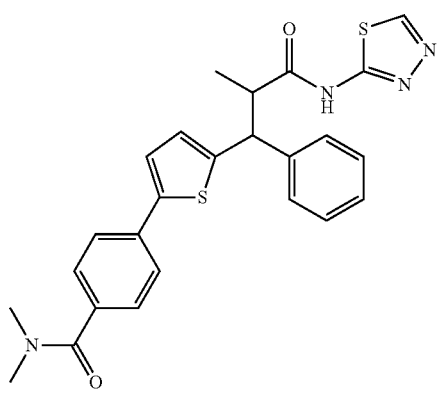<br>Diastereomer 2 | 477.1 | 3.413 |
| 148 | 2-chloro-N,N-dimethyl-4-(5-(2-methyl-3-oxo-1-phenyl-3-(1,3,4-thiadiazol-2-ylamino)propyl)-2-thienyl)benzamide | 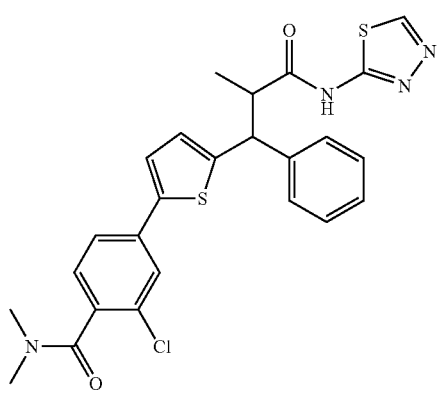<br>Diastereomer 1 | 511 | 3.478 |
| 149 | 2-chloro-N,N-dimethyl-4-(5-(2-methyl-3-oxo-1-phenyl-3-(1,3,4-thiadiazol-2-ylamino)propyl)-2-thienyl)benzamide | 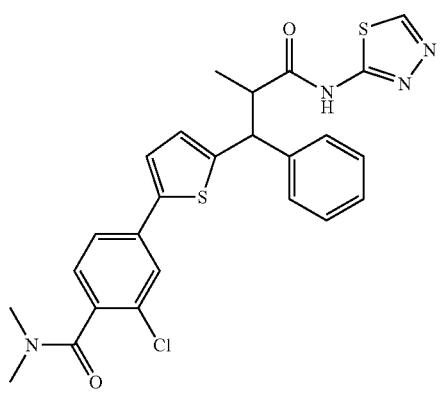<br>Diastereomer 2 | 511 | 3.556 |

| Example No. | Name | Structure | MS [m/z (M + H)] | HPLC Rt: minute |
|---|---|---|---|---|
| 150 | N-ethyl-N-methyl-4-(5-(2-methyl-3-oxo-1-phenyl-3-(1,3,4-thiadiazol-2-ylamino)propyl)-2-thienyl)benzamide | Diastereomer 1 | 491.1 | 3.456 |
| 151 | N-ethyl-N-methyl-4-(5-(2-methyl-3-oxo-1-phenyl-3-(1,3,4-thiadiazol-2-ylamino)propyl)-2-thienyl)benzamide | Diastereomer 2 | 491.1 | 3.528 |

Example 152 to 155

In a similar manner to the chiral separation of Example 98 to give Examples 106 and 107, the title compounds of following examples were resolved into the corresponding enantiomers using chiral supercritical fluid chromatography (SFC).

Example 144 was resolved to Examples 152 and 153. Analytical HPLC (Column: Chiralpak AD, CO2/EtOH 65:35, Flowrate: 2 mL/min, Detection: 305 nm) Retention times: (2S,3S)-enantiomer (Example 152), 14.19 min (ee>99.9%); (2R,3R)-enantiomer (Example 153), 16.17 min (ee>98%).

Example 150 was resolved to Examples 154 and 155. Analytical HPLC (Column: Chiralpak AS, CO2/MeOH 70:30, Flowrate: 2 mL/min, Detection: 300 nm) Retention times: (2S,3S)-enantiomer (Example 154), 14.32 min (ee>99.9%); (2R,3R)-enantiomer (Example 155), 22.07 min (ee>99.9%).

| Example No. | Name | Structure | MS [m/z (M + H)] | HPLC Rt: minute |
|---|---|---|---|---|
| 152 | (2R,3R)-2-methyl-3-(5-(4-(4-morpholinylcarbonyl)phenyl)-2-thienyl)-3-phenyl-N-1,3,4-thiadiazol-2-ylpropanamide | (2S,3S) | 519 | 3.245 |

| Example No. | Name | Structure | MS [m/z] (M + H)] | HPLC Rt: minute |
|---|---|---|---|---|
| 153 | N-ethyl-N-methyl-4-(5-((1S,2S)-2-methyl-3-oxo-1-phenyl-3-(1,3,4-thiadiazol-2-ylamino)propyl)-2-thienyl)benzamide | (2R,3R) | 519.1 | 3.250 |
| 154 | N-ethyl-N-methyl-4-(5-((1R,2R)-2-methyl-3-oxo-1-phenyl-3-(1,3,4-thiadiazol-2-ylamino)propyl)-2-thienyl)benzamide | (2S,3S) | 491.1 | 3.445 |
| 155 | (2S,3S)-2-methyl-3-(5-(4-(4-morpholinylcarbonyl)phenyl)-2-thienyl)-3-phenyl-N-1,3,4-thiadiazol-2-ylpropanamide | (2R,3R) | 491.1 | 3.443 |

Biological Activity Data

The AP-1 activity of Examples 1 to 155 is given where the AP-1 $EC_{50}$ is less than 1 uM. Accompanying AP-1 maximum inhibition values are also given. Where the AP-1 EC50 is greater than 1 uM and/or the maximal inhibition is less than 20%, the glucocorticoid receptor (GR) binding affinity (Ki) is given.

The data presented below were obtained using the assays referred to in the table below and described herein in the ASSAY section supra.

| Example No. | GR (Ki, nM) (GR Binding Assay (I)[a]) | GR (% RBA* @ 10 μM) (GR Binding Assay (II)[b]) | AP-1 $EC_{50}$, nM (Cellular Transrepression Assay) | AP-1 Max % inh (Cellular Transrepression Assay) |
|---|---|---|---|---|
| 1 | | 6.40 | | |
| 2 | | 10.10 | | |
| 3 | 3.66 | | | |

| Example No. | GR (Ki, nM) (GR Binding Assay (I)[a]) | GR (% RBA* @ 10 μM) (GR Binding Assay (II)[b]) | AP-1 EC$_{50}$, nM (Cellular Transrepression Assay) | AP-1 Max % inh (Cellular Transrepression Assay) |
|---|---|---|---|---|
| 4 | 6.97 | | | |
| 5 | | | 18.70 | 89.86 |
| 6 | | 501.50 | | |
| 7 | | 160.70 | | |
| 8 | | | | |
| 9 | 24.55 | 49.70 | | |
| 10 | | | 699.60 | 39.98 |
| 11 | | 7.40 | | |
| 12 | | 6.10 | | |
| 13 | | | 245.20 | 42.20 |
| 14 | | | 62.91 | 46.02 |
| 15 | | 14.70 | | |
| 16 | | 90.40 | | |
| 17 | | 112.20 | | |
| 18 | | 37.20 | | |
| 19 | 2.93 | | | |
| 20 | | 152.00 | | |
| 21 | | | 40.45 | 23.95 |
| 22 | | 477.30 | | |
| 23 | | | 142.20 | 29.42 |
| 24 | | 16.30 | | |
| 25 | | 73.40 | | |
| 26 | | | 316.10 | 41.43 |
| 27 | | 52.80 | | |
| 28 | | 186.70 | | |
| 29 | 7.69 | | | |
| 30 | | | 48.99 | 39.36 |
| 31 | | | 21.53 | 46.75 |
| 32 | | | 73.92 | 43.12 |
| 33 | | | 24.02 | 37.67 |
| 34 | | | | |
| 35 | 5.75 | | | |
| 36 | 1.46 | | | |
| 37 | 53.49 | | | |
| 38 | | | 8.43 | 23.10 |
| 39 | | | 18.81 | 44.23 |
| 40 | | | 5.36 | 37.26 |
| 41 | | | 6.50 | 65.52 |
| 42 | | | 11.63 | 42.89 |
| 43 | | | 10.69 | 38.40 |
| 44 | 0.89 | | | |
| 45 | | | 5.88 | 51.02 |
| 46 | 11.71 | | | |
| 47 | | | 3.71 | 39.94 |
| 48 | 17.35 | | | |
| 49 | 3.58 | | | |
| 50 | | | 13.20 | 39.62 |
| 51 | 79.65 | | | |
| 52 | | | 12.07 | 38.47 |
| 53 | 151.80 | | | |
| 54 | | | 9.45 | 62.42 |
| 55 | 36.76 | | | |
| 56 | 1.21 | | | |
| 57 | 2.39 | | | |
| 58 | 29.24 | | | |
| 59 | 66.95 | | | |
| 60 | 160.50 | | | |
| 61 | 100.60 | | | |
| 62 | 87.59 | | | |
| 63 | 565.20 | | | |
| 64 | | | 3.04 | 53.84 |
| 65 | | | 7.00 | 49.65 |
| 66 | | | 5.16 | 50.37 |
| 67 | | | 12.84 | 51.23 |
| 68 | | | 7.31 | 49.38 |
| 69 | 1.03 | | | |
| 70 | | | 833.30 | 22.97 |
| 71 | 1.51 | | | |
| 72 | 29.84 | | | |
| 73 | 6.13 | | | |
| 74 | 2.24 | | | |
| 75 | 1.52 | | | |
| 76 | 27.03 | | | |
| 77 | 4.19 | | | |
| 78 | 24.47 | | | |
| 79 | | | 30.34 | 42.56 |
| 80 | | | 34.73 | 33.59 |
| 81 | 4.32 | | | |
| 82 | 2.66 | | | |
| 83 | | | 16.65 | 32.70 |
| 84 | 5.06 | | | |
| 85 | 2.74 | | | |
| 86 | | | 53.94 | 36.20 |
| 87 | | | 8.49 | 41.07 |
| 88 | | | 15.70 | 43.56 |
| 89 | | | 2.41 | 36.74 |
| 90 | | | 20.57 | 32.70 |
| 91 | 4.59 | | | |
| 92 | 1.14 | | | |
| 93 | 2.79 | | | |
| 94 | 4.11 | | | |
| 95 | 0.76 | | | |
| 96 | | | 71.09 | 27.36 |
| 97 | 1.96 | | | |
| 98 | | | 15.76 | 55.31 |
| 99 | | | 279.00 | 49.36 |
| 100 | | | 8.80 | 50.60 |
| 101 | | | 575.90 | 51.00 |
| 102 | | | 10.64 | 52.60 |
| 103 | | | 879.30 | 49.86 |
| 104 | | | 38.68 | 49.53 |
| 105 | | | 446.40 | 48.50 |
| 106 | 2.44 | | | |
| 107 | | | 15.88 | 52.51 |
| 108 | 5.39 | | | |
| 109 | | | 8.39 | 57.47 |
| 110 | | | 24.61 | 47.00 |
| 111 | | | 21.21 | 53.26 |
| 112 | | | 18.46 | 53.98 |
| 113 | | | 17.88 | 37.84 |
| 114 | | | 45.45 | 36.56 |
| 115 | | | 31.00 | 39.12 |
| 116 | | | 67.66 | 40.77 |
| 117 | | | 14.37 | 56.55 |
| 118 | | | 61.60 | 55.28 |
| 119 | | | 22.71 | 47.56 |
| 120 | | | 22.92 | 42.90 |
| 121 | | | 66.84 | 28.67 |
| 122 | 1.91 | | | |
| 123 | 7.16 | | | |
| 124 | 7.27 | | | |
| 125 | 5.71 | | | |
| 126 | 220.00 | | | |
| 127 | 148.30 | | | |
| 128 | 277.30 | | | |
| 129 | 157.70 | | | |
| 130 | 160.30 | | | |
| 131 | 235.80 | | | |
| 132 | 3.20 | | | |
| 133 | 4.85 | | | |
| 134 | 1.06 | | | |
| 135 | 1.25 | | | |
| 136 | 1.98 | | | |
| 137 | 4.73 | | | |
| 138 | 360.40 | | | |
| 139 | 258.60 | | | |
| 140 | | | 15.19 | 54.06 |
| 141 | | | 62.20 | 45.96 |
| 142 | 3.20 | | | |
| 143 | | | 16.86 | 63.62 |
| 144 | | | 5.98 | 49.49 |
| 145 | | | 64.61 | 25.24 |
| 146 | | | 14.58 | 59.12 |
| 147 | | | 167.70 | 48.44 |
| 148 | | | 24.62 | 51.50 |
| 149 | | | 216.50 | 54.20 |
| 150 | | | 17.51 | 57.18 |
| 151 | | | 203.30 | 48.08 |

| Example No. | GR (Ki, nM) (GR Binding Assay (I)[a]) | GR (% RBA* @ 10 μM) (GR Binding Assay (II)[b]) | AP-1 EC$_{50}$, nM (Cellular Transrepression Assay) | AP-1 Max % inh (Cellular Transrepression Assay) |
|---|---|---|---|---|
| 152 | 4.85 | | | |
| 153 | | | 11.96 | 63.60 |
| 154 | 2.15 | | | |
| 155 | | | 8.27 | 61.47 |

*% RBA = % Relative Binding Affinity to dexamethasone

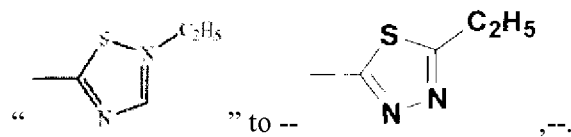

What is claimed is:

1. A compound according to formula (I),

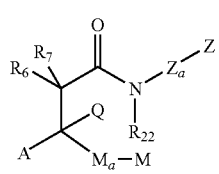

or an enantiomer, diastereomer, tautomer, or a pharmaceutically-acceptable salt, thereof, wherein:
A is thienyl substituted with one to four groups, $R_1$, $R_2$, $R_3$, and/or $R_4$;
M is aryl;
$M_a$ is a linker between C and M and is a bond;
Q is hydrogen;
$Z_a$—Z is

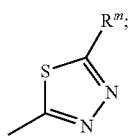

$R^m$ is selected from the group consisting of hydrogen, halogen, alkyl, substituted alkyl, alkenyl, substituted alkenyl, alkynyl, substituted alkynyl, nitro, cyano, $OR_{23}$, $NR_{23}R_{24}$, $C(=O)R_{23}$, $CO_2R_{23}$, $C(=O)NR_{23}R_{24}$, —O—$C(=O)R_{23}$, $NR_{23}C(=O)R_{24}$, $NR_{23}C(=O)OR_{24}$, $NR_{23}C(=S)OR_{24}$, $S(=O)_pR_{25}$, $NR_{23}SO_2R_{25}$, $SO_2NR_{23}R_{24}$, cycloalkyl, heterocyclo, aryl, and heteroaryl;
$R_{23}$ and $R_{24}$ at each occurrence are independently selected from the group consisting of hydrogen, alkyl, substituted alkyl, C(=O)alkyl, CO$_2$(alkyl), SO$_2$alkyl, alkenyl, substituted alkenyl, alkynyl, substituted alkynyl, amino, aryl, heteroaryl, heterocyclo, and cycloalkyl;
$R_{25}$ is selected from the group consisting of alkyl, substituted alkyl, alkenyl, substituted alkenyl, alkynyl, substituted alkynyl, amino, substituted amino, heteroaryl, heterocyclo, cycloalkyl, and aryl;
$R_1$, $R_2$, $R_3$, and $R_4$ at each occurrence are independently selected from the group consisting of hydrogen, halogen, alkyl, substituted alkyl, alkenyl, substituted alkenyl, alkynyl, substituted alkynyl, nitro, cyano, —$OR_{10}$, —$SR_{10}$, —$NR_{10}R_{11}$, —$C(=O)R_{10}$, —$CO_2R_{10}$, —$C(=O)NR_{10}R_{11}$, —O—$C(=O)R_{10}$, —$NR_{10}C(=O)R_{11}$, —$NR_{10}C(=O)OR_{11}$, —$NR_{10}C(S)OR_{11}$, —$S(=O)_pR_{12}$, —$NR_{10}SO_2R_{12}$, —$SO_pNR_{10}R_{11}$, cycloalkyl, heterocyclo, aryl, and heteroaryl;

$R_6$ is selected from alkyl or substituted alkyl;
$R_7$ is selected from hydrogen alkyl, or substituted alkyl;
$R_{10}$ and $R_{11}$ at each occurrence are independently selected from the group consisting of:
hydrogen, alkyl, substituted alkyl, alkenyl, substituted alkenyl, alkynyl, substituted alkynyl, —SO$_p$alkyl, cycloalkyl, aryl, heteroaryl, and heterocyclo;
$R_{12}$ is independently selected from the group consisting of alkyl, substituted alkyl, alkenyl, substituted alkenyl, alkynyl, substituted alkynyl, cycloalkyl, aryl, heteroaryl, and heterocyclo;
$R_{22}$ is hydrogen; and
p is 1 or 2.

2. A compound according to claim 1, or an enantiomer, diastereomer, or a pharmaceutically-acceptable salt thereof, wherein:
Q is hydrogen;
M is aryl, alkylaryl, or haloaryl;
$R_6$ is $C_{1-4}$alkyl; and
$R_7$ is hydrogen, $C_{1-4}$-alkyl, or substituted $C_{1-4}$alkyl.

3. A compound according to claim 1, or an enantiomer, diastereomer, or a pharmaceutically-acceptable salt thereof, wherein:
$Z_a$ is a bond; and
Z is substituted with $R^m$.

4. A compound according to claim 1 having formula (Ia),

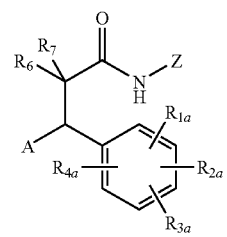

or an enantiomer, diastereomer, or a pharmaceutically-acceptable salt thereof, wherein:
A is thienyl optionally substituted by 1 to 4 groups, $R_1$, $R_2$, $R_3$, and/or $R_4$;
Z is

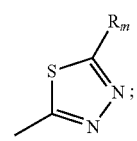

$R^m$ is selected from the group consisting of hydrogen, halogen, cycloalkyl, cyano, haloalkyl, thioalkyl, —$CO_2R_{23}$, —$NR_{23}R_{24}$, —$C(=O)R_{23}$, —$C(O)N(R_{23})(R_{24})$, $OR_{23}$, $C_{1-4}$-alkyl, substituted $C_{1-4}$-alkyl, aryl, heteroaryl and heterocyclo;
$R_1$, $R_2$, $R_3$, $R_4$, $R_{1a}$, $R_{2a}$, $R_{3a}$, and $R_{4a}$ are independently selected from the group consisting of (i) hydrogen, halogen, $C_{1-4}$-alkyl, CN, $C_{2-4}$alkenyl, $C_{2-4}$alkynyl, $SR_{10}$, $SO_2R_{12}$, $OR_{10}$, $SO_pNR_{10}R_{11}$, and $NR_{10}R_{11}$; and/or (ii) $C_{0-3}$alkylene substituted by an optionally substituted group selected from phenyl and a 5- to 7-membered heterocyclo or heteroaryl;

$R_6$ is $C_{1-4}$alkyl;

$R_7$ is hydrogen, $C_{1-4}$alkyl, or $C_{1-4}$substituted alkyl;

$R_{10}$ and $R_{11}$ at each occurrence are independently selected from the group consisting of (i) hydrogen, $C_{1-6}$alkyl, substituted $C_{1-6}$alkyl, and —$SO_2(C_{1-4}$alkyl); and/or (ii) $C_{3-7}$cycloalkyl, heterocyclo, aryl, and heteroaryl, each is group optionally substituted; and/or (iii) $R_{10}$ is taken together with $R_{11}$ and the nitrogen atom to which they are both attached to form a 4- to 6-membered heteroaryl or heterocyclo, each group is optionally substituted;

$R_{12}$ at each occurrence is independently selected from the group consisting of an optionally substituted group selected from $C_{1-6}$alkyl, $C_{3-7}$cycloalkyl, heterocyclo, aryl, and heteroaryl; and $R_{23}$ and $R_{24}$ at each occurrence are independently selected from the group consisting of hydrogen, alkyl, substituted alkyl, C(=O)alkyl, $CO_2$(alkyl), $SO_2$alkyl, alkenyl, substituted alkenyl, alkynyl, substituted alkynyl, amino, aryl, heteroaryl, heterocyclo, and cycloalkyl.

5. A compound according to claim 4, or an enantiomer, diastereomer, or a pharmaceutically-acceptable salt thereof, wherein A is thienyl optionally substituted by one to two groups selected from the group consisting of halogen, alkoxy, morpholinyl, piperidinyl optionally substituted by OH, —NH($CH_2$)$_n$(phenyl optionally substituted by $C_{1-4}$alkyl), pyrrolidinyl, furyl, and phenyl wherein the phenyl is optionally substituted by one to two groups selected from halogen, alkoxy, $C_{1-6}$alkyl, $CO_2R_{10}$ or $C(O)NR_{10}R_{11}$; and n is 0, 1 or 2.

6. A compound according to claim 4, or an enantiomer, diastereomer, or a pharmaceutically-acceptable salt thereof, wherein A is selected from the group consisting of:

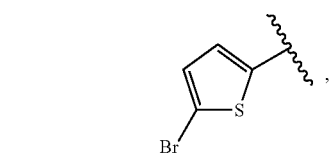,

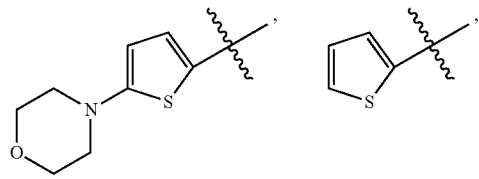,

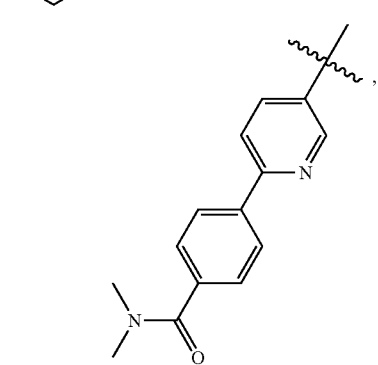,

-continued

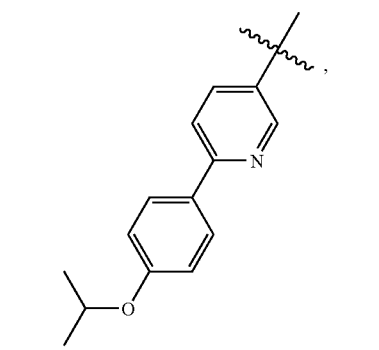,

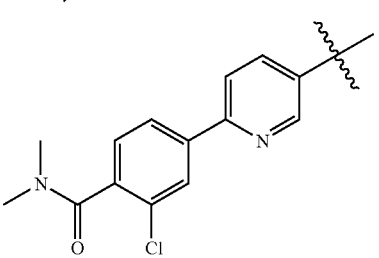,

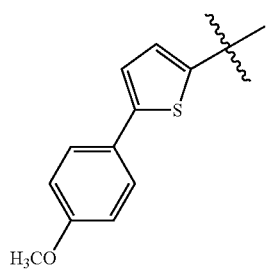,

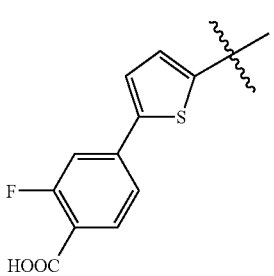,

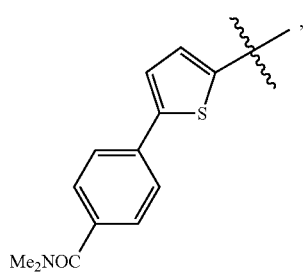,

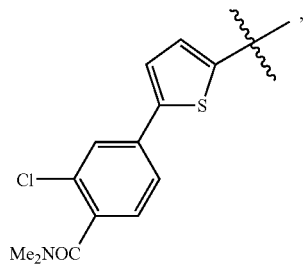,

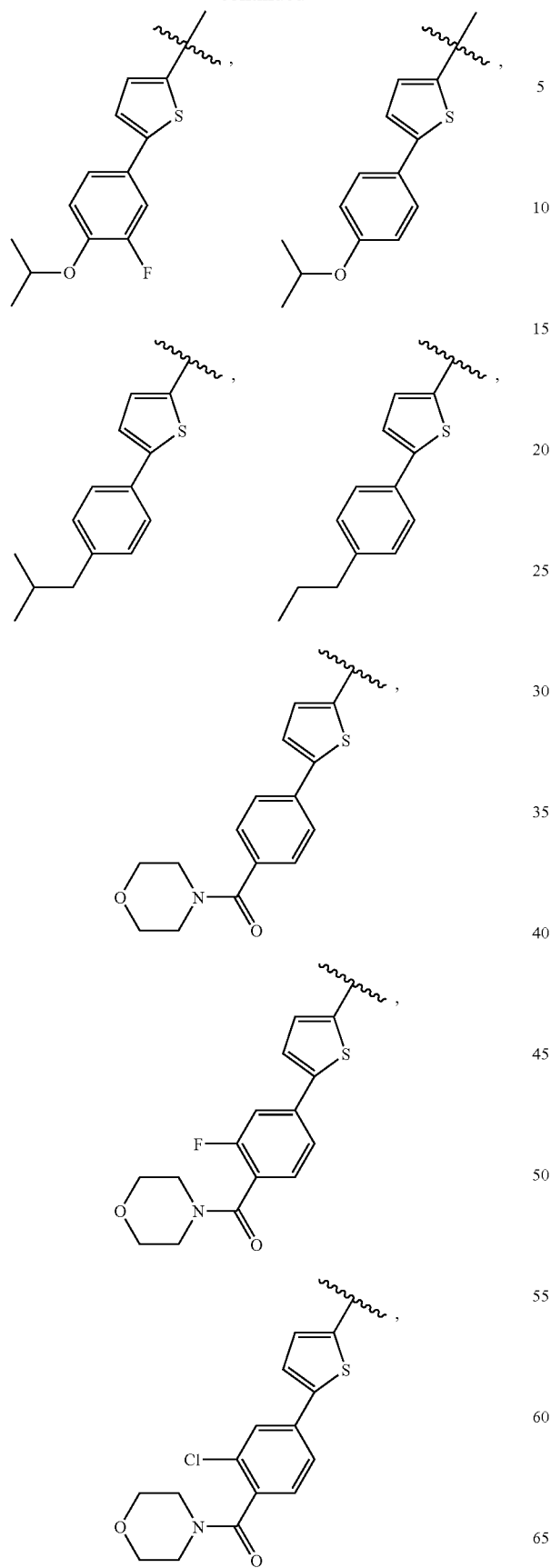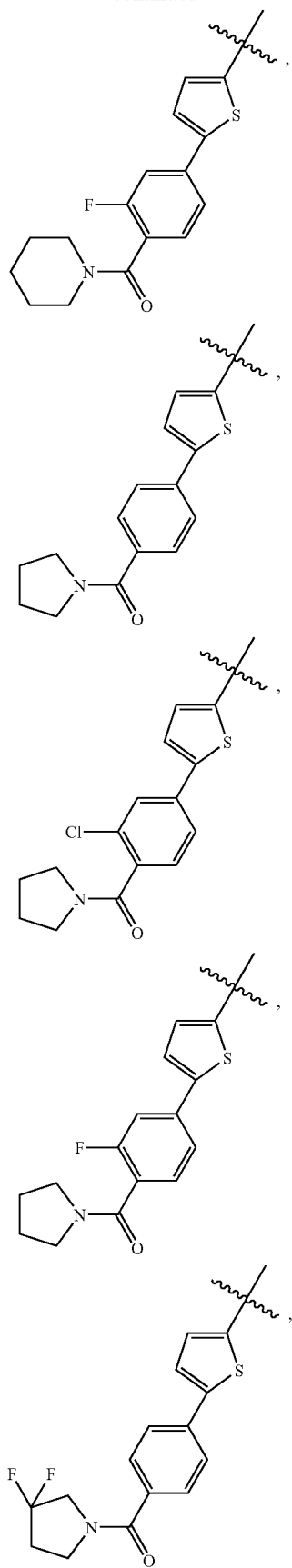

-continued
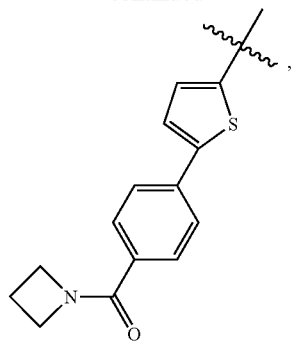
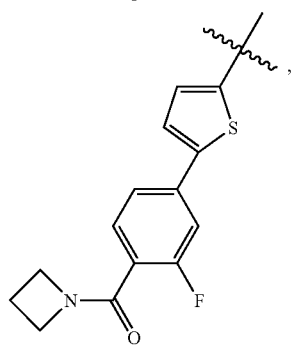
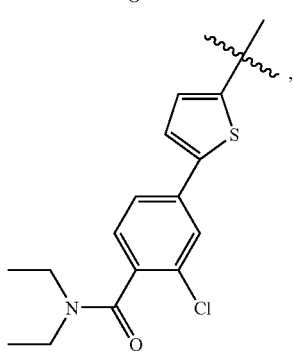
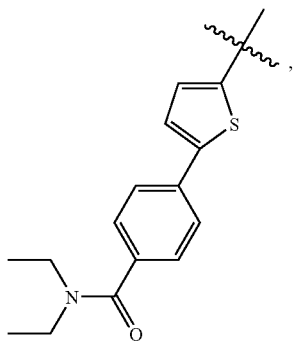
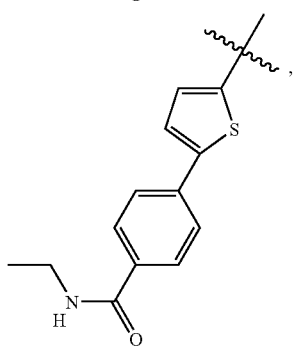
-continued
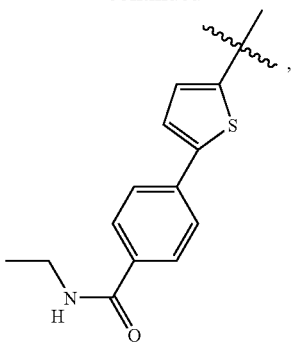
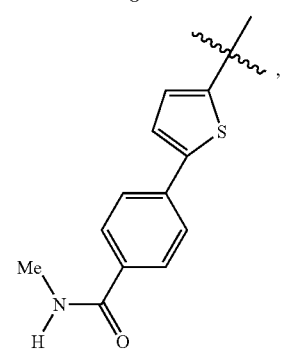
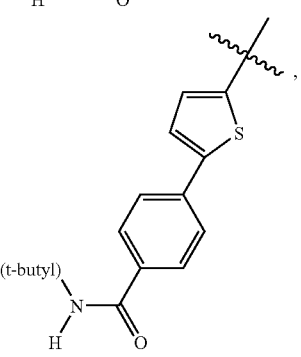
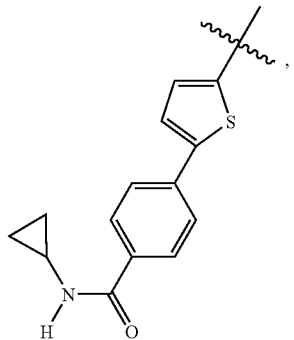
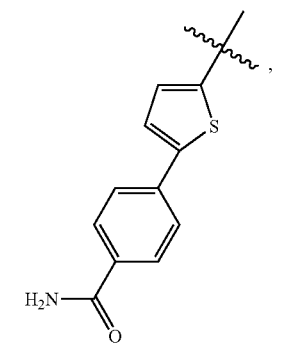

-continued

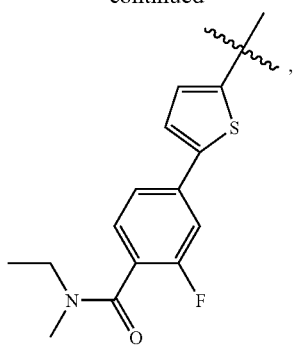,

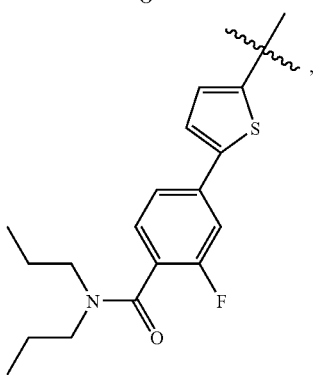,

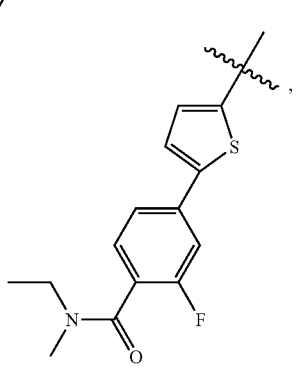,

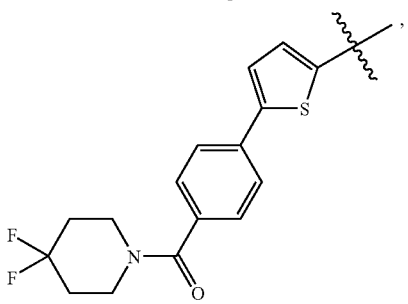 and

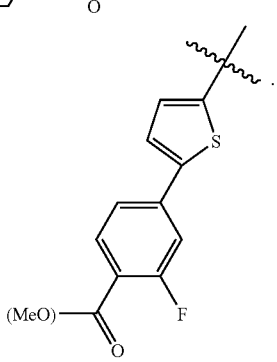.

7. A compound according to claim 4, or an enantiomer, diastereomer, or a pharmaceutically-acceptable salt thereof, wherein $R_{1a}$, $R_{2a}$, $R_{3a}$, and $R_{4a}$ are selected from the group consisting of hydrogen, $C_{1-4}$alkyl, halogen, nitro, cyano, hydroxy, $C_{1-4}$alkoxy, morpholinyl, piperidinyl, piperazinyl, and pyrrolidinyl.

8. A compound according to claim 4, or an enantiomer, diastereomer, or a pharmaceutically-acceptable salt thereof, wherein:
Z is

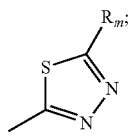;

$R^m$ is hydrogen, $-CO_2R_{23}$, $-C(O)N(R_{23})(R_{24})$, or

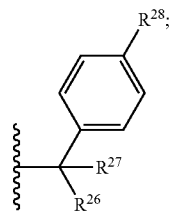;

$R_{23}$ and $R_{24}$ at each occurrence are independently selected from hydrogen and $C_{1-4}$alkyl; or $R_{23}$ and $R_{24}$ together with the nitrogen atom to which they are attached form a 5- to 7-membered heterocyclo;
$R^{26}$ and $R^{27}$ are independently hydrogen, halogen, or hydroxy; or $R^{26}$ and $R^{27}$ combine to form =O; and
$R^{28}$ is selected from the group consisting of $C_{1-4}$alkoxy; halogen, pyrimidinyl, isoxazolyl, pyrazolyl, or pyridinyl, each group optionally substituted by hydrogen, morpholinyl, $C_{1-4}$alkoxy, and $C_{1-4}$alkyl.

9. A compound according to claim 1, or an enantiomer, diastereomer, or a pharmaceutically-acceptable salt thereof, wherein:
$R_6$ is selected from $C_{1-4}$alkyl; and
$R_7$ is selected from hydrogen and $C_{1-4}$alkyl.

10. A method of treating a disease or disorder selected from a metabolic disease and an inflammatory or immune disease comprising administering to a patient in need of treatment, a therapeutically effective amount of a compound according to claim 1.

11. A pharmaceutical composition comprising a compound according to claim 1 and a pharmaceutically acceptable carrier therefor.

12. A pharmaceutical combination comprising a compound as defined in claim 1 and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

13. A compound having the structure

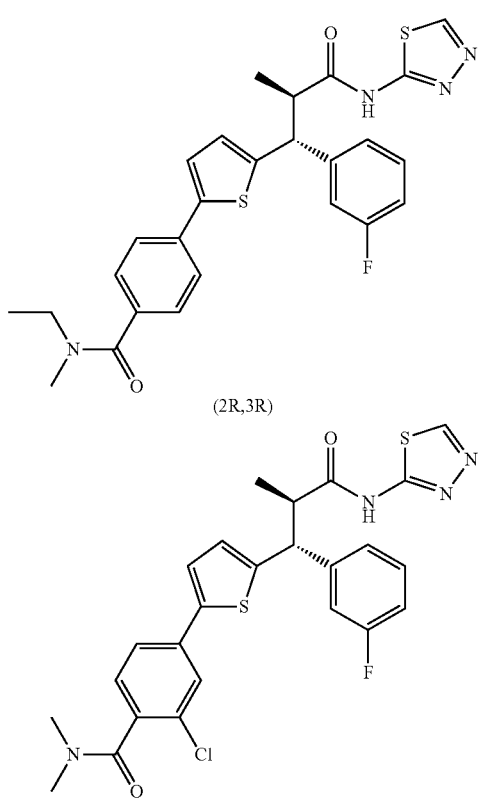

(2R,3R)

or or a pharmaceutically acceptable salt thereof.

14. The compound as defined in claim 4 wherein:

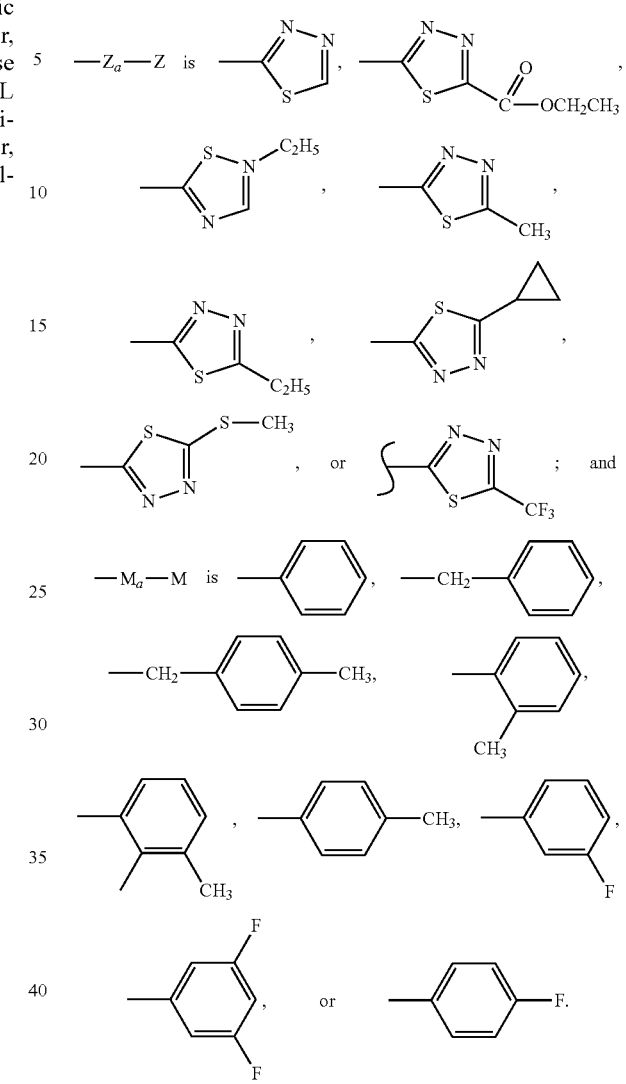

* * * * *

UNITED STATES PATENT AND TRADEMARK OFFICE
CERTIFICATE OF CORRECTION

PATENT NO. : 8,222,247 B2  
APPLICATION NO. : 12/513229  
DATED : July 17, 2012  
INVENTOR(S) : Bingwei Vera Yang et al.

Page 1 of 3

It is certified that error appears in the above-identified patent and that said Letters Patent is hereby corrected as shown below:

On the Title Page:

Item (54), line 2, change "NF-KAPPABETA" to -- NF-κB --.

Item (56), References Cited, under OTHER PUBLICATIONS:

Column 1, Baldwin, Jr., A.S. reference, change "NF-ηB" to -- NF-κB --.

The reference should read:

-- Baldwin, Jr., A.S., "The transcription factor NF-κB and human disease", The Journal of Clinical Investigation, vol. 107, No. 1, pp. 3-6 (2001). --.

Item (57), ABSTRACT:

Column 2, lines 10 and 11 (Abstract), after "provided that (i) A is not tetrazole or (ii) if A is thienyl or furanyl then Z", insert -- is selected from a group other than succinimido or thalimido; --.

Column 2, line 12 (Abstract), after "heteroaryl;" insert -- $M_a$ is a linker between C and M and is selected from a bond and $C_1$-$C_3$alkylene; Q is selected from (i) hydrogen, halogen, nitro, cyano, hydroxy, $C_{1-4}$alkyl, and substituted $C_{1-4}$ alkyl; or (ii) Q is combined with $R_6$ and with the carbon atoms to which they are attached to form a 3- to 6-membered cycloalkyl; or (iii) Q and M are combined with the carbon atom(s) to which they are attached to form a 3- to 7-membered ring containing 1-2 heteroatoms which are independently selected from the group consisting of O, S, $SO_2$, and N which ring may be optionally substituted with 0-2 $R_5$ groups or carbonyl; and --.

Column 2, line 13 (Abstract), change "CF3" to -- $CF_3$ --.

Signed and Sealed this  
Twenty-eighth Day of May, 2013

Teresa Stanek Rea  
*Acting Director of the United States Patent and Trademark Office*

CERTIFICATE OF CORRECTION (continued)
U.S. Pat. No. 8,222,247 B2

Column 2, line 15 (Abstract), after "—$SO_2NR_8R_9$.", insert -- $M_a$, $Z_a$, $R_1$, $R_2$, $R_3$, $R_{5a}$, $R_6$, $R_7$, $R_8$, $R_9$ and $R_{22}$ are as defined herein. --.

In the Specification:

Column 1, line 2, change "NF-KAPPABETA" to -- NF-κB --.

In the Claims:

Claim 2:

Column 164, line 22, change "$C_{1-4}$-alkyl," to -- $C_{1-4}$alkyl, --.

Claim 4:

Column 164, line 59, change "$C_{1-4}$-alkyl, substituted $C_{1-4}$-alkyl," to -- $C_{1-4}$alkyl, substituted $C_{1-4}$alkyl, --.

Column 164, line 63, change "$C_{1-4}$-alkyl," to -- $C_{1-4}$alkyl, --.

Claim 6:

Column 165, lines 54 to 66, delete

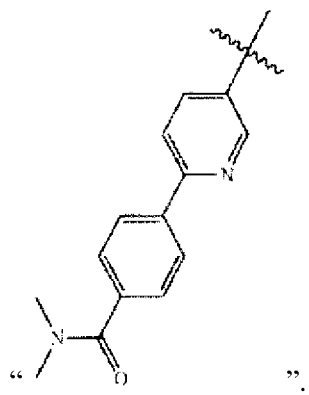

".

CERTIFICATE OF CORRECTION (continued)  
U.S. Pat. No. 8,222,247 B2

Page 3 of 3

In the Claims:

Claim 6 (continued):

Column 166, lines 2 to 24, delete

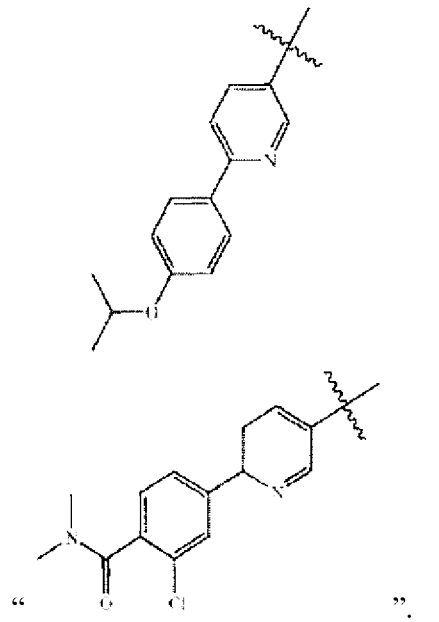

".

Column 171, lines 29 to 41, change

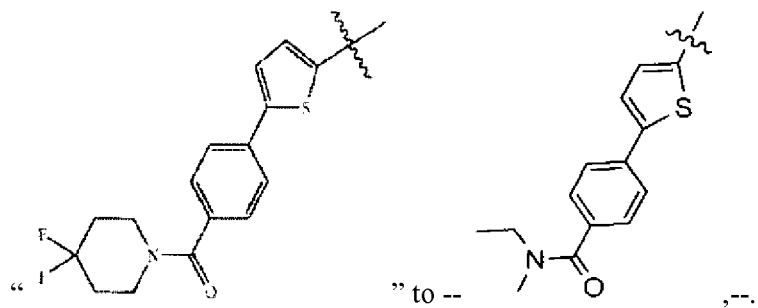

Claim 14:

Column 174, lines 8 to 11, change